(12) United States Patent
Matos

(10) Patent No.: US 9,082,156 B2
(45) Date of Patent: Jul. 14, 2015

(54) EMERGENCY MANAGEMENT SYSTEM

(76) Inventor: Jeffrey A. Matos, New Rochelle, NY (US)

( * ) Notice: Subject to any disclaimer, the term of this patent is extended or adjusted under 35 U.S.C. 154(b) by 1370 days.

(21) Appl. No.: 11/502,484

(22) Filed: Aug. 10, 2006

(65) Prior Publication Data
US 2007/0043585 A1 Feb. 22, 2007

Related U.S. Application Data

(60) Provisional application No. 60/709,078, filed on Aug. 17, 2005.

(51) Int. Cl.
*A61N 1/18* (2006.01)
*A61N 1/37* (2006.01)
*G06Q 50/22* (2012.01)

(52) U.S. Cl.
CPC ........................................ *G06Q 50/22* (2013.01)

(58) Field of Classification Search
USPC ................ 607/2–5, 9, 10, 11, 30, 31, 32, 59; 600/509
See application file for complete search history.

(56) References Cited

U.S. PATENT DOCUMENTS

| | | | | |
|---|---|---|---|---|
| 6,104,949 A | * | 8/2000 | Pitts Crick et al. | 600/547 |
| 2003/0023178 A1 | * | 1/2003 | Bischoff et al. | 600/515 |
| 2003/0130708 A1 | | 7/2003 | Von Arx et al. | |
| 2003/0181950 A1 | * | 9/2003 | Powers et al. | 607/5 |
| 2003/0191402 A1 | * | 10/2003 | Arzbaecher et al. | 600/509 |
| 2003/0233129 A1 | * | 12/2003 | Matos | 607/5 |
| 2004/0049235 A1 | * | 3/2004 | Deno et al. | 607/9 |

* cited by examiner

*Primary Examiner* — Allen Porter, Jr.
(74) *Attorney, Agent, or Firm* — Karl F. Milde, Jr.; Eckert Seamans Cherin & Mellott, LLC

(57) ABSTRACT

The present disclosure relates to systems and methods for:
1) displaying all vital central station (CS) information and controls on a single screen;
2) linking peripheral central stations (pCSs) to a master central station (mCS);
3) operating the system disclosed in U.S. Ser. No. 10/460,458, without medical professionals (MPs) in the mCS or without any mCS;
4) linking a remote controlled defibrillator (RCD™) unit to an arrest sensor;
5) operating an RCD unit in a motor vehicle and linking an RCD unit to a vehicle communications system;
6) linking an RCD unit to a CS through a network of: a) non-vehicle-based stationary units (SUs), b) vehicle-based SUs/vehicle communication systems, or c) non-vehicle-based SUs and vehicle-based SUs/vehicle communication systems;
7) using an RCD unit with a chest compression device;
8) using the network of RCD units and MPs for disaster monitoring; and
9) monitoring and treating hospital patients and motor vehicle passengers.

52 Claims, 57 Drawing Sheets

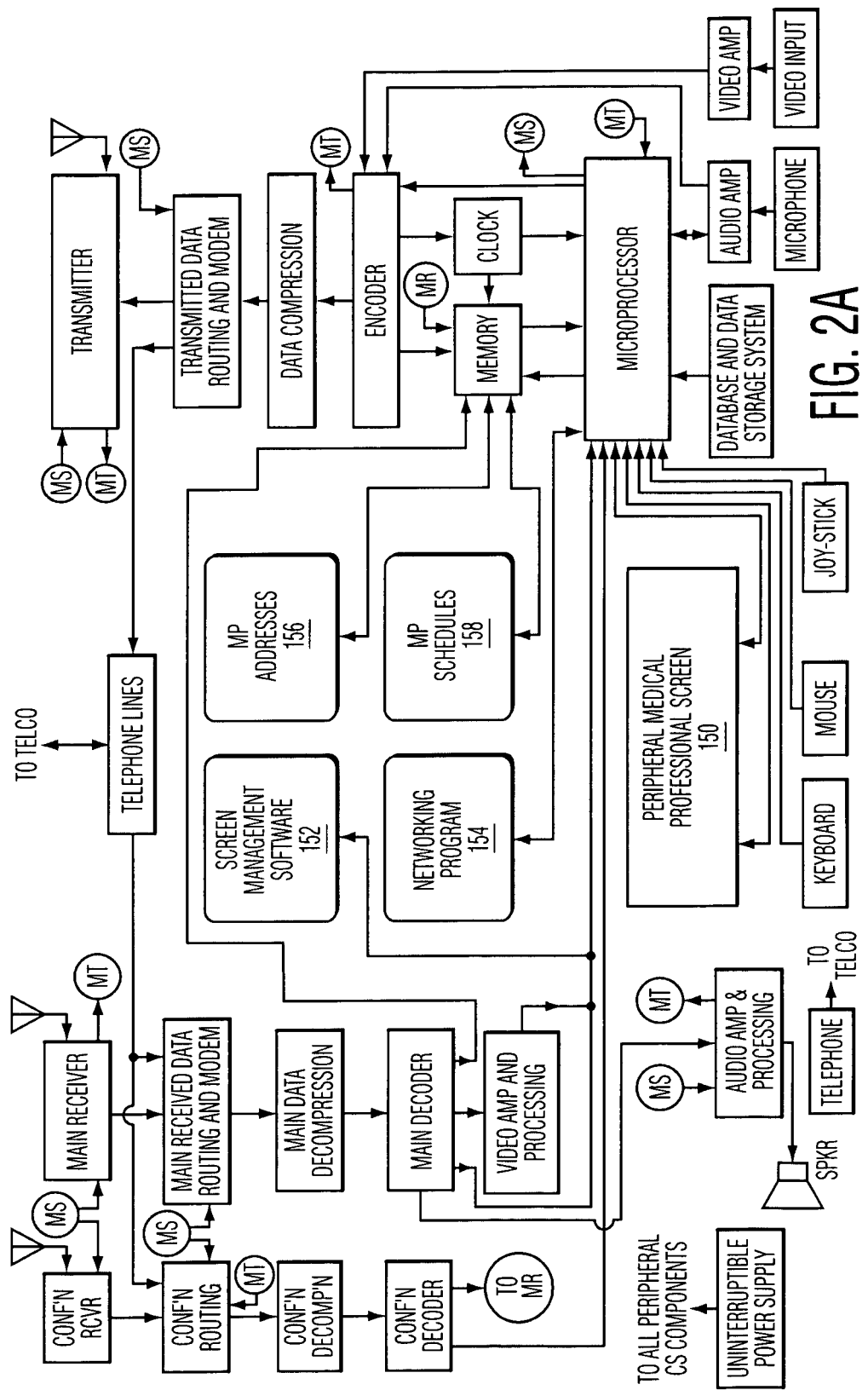

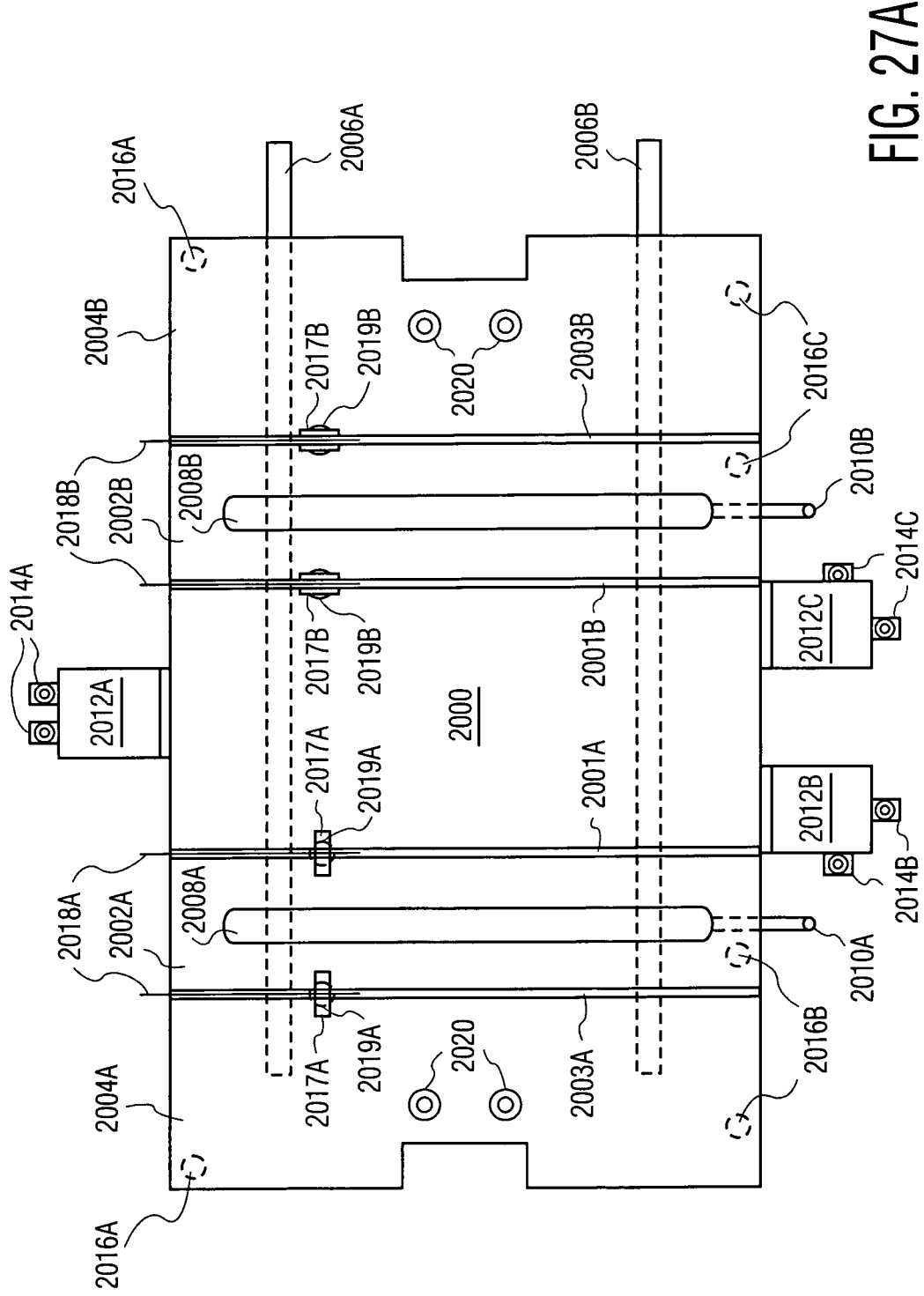

EMERGENCY MANAGEMENT SYSTEM

CROSS-REFERENCE TO RELATED APPLICATION

This present application claims benefit of priority from U.S. Provisional Application Ser. No. 60/709,078, filed Aug. 17, 2005. This application is also related to U.S. patent application Ser. No. 10/460,458, published on Dec. 18, 2003 as U.S. Patent Publication No. US/2003/0233129. This publication is incorporated herein by reference.

BACKGROUND OF THE INVENTION

U.S. patent application Ser. No. 10/460,458 (hereinafter, "10/460,458") discloses a System for Cardiac Resuscitation. Said system allows a remotely located "medical professional" (MP), such as a licensed physician, to resuscitate the victim of a cardiac arrest. In one preferred embodiment of the invention, the MP can view the victim's ECG and make a decision about whether a defibrillation shock is advisable. If the shock is advisable, the MP causes the delivery of the shock. A bystander (referred to in the application as an "enabler" (EN)) functions to:
  a) notify the central station of the event by pressing a button on the remotely located defibrillator (referred to in the application as the "portable unit" (PU));
  b) provide the MP with information, if any is available, about details of the victim's medical history and/or the events immediately preceding the collapse;
  c) move the PU to the victim's side;
  d) remove any portion of the victim's clothing deemed necessary by the MP, under the guidance of the MP;
  e) attach one or more electrode pads to the victim's chest, under the guidance of the MP; and
  f) if necessary, perform chest compression, under the guidance of the MP.

The MP functions include:
  a) analyzing the heart rhythm (or causing it to be analyzed) displayed by the electrocardiogram;
  b) thereafter deciding on whether defibrillation, pacing, or neither is called for;
  c) if defibrillation is called for, deciding on the details of the shock and its administration;
  d) if pacing is called for deciding on the details of the pacing and its administration;
  e) deciding if CPR is called for; and, if it is, deciding on when it should be administered, instructing the EN in its administration, and monitoring the performance of the EN and the response of the victim;
  f) contacting the "911" emergency team nearest to the victim;
  g) accessing any available victim medical records; including those containing victim "advanced directives," i.e. a statement of the procedures and methods allowed by the victim in the event of a medical emergency;
  h) accessing any necessary databases, including victim implanted devices, and pharmacologic information;
  i) participating in a decision to terminate therapy in the case of a futile effort;
  j) advising emergency medical personnel when they arrive on-scene; and
  k) maintaining the emergency equipment at both the CS end and the RCD unit end.

Abbreviations and Nomenclature:
  In the text hereinbelow and in the accompanying figures:
  RCD™ is a trademark of Jeffrey A. Matos for a "remotely controlled defibrillator unit". An RCD unit which includes the portable unit (PU) described in U.S. Ser. No. 10/460,458 and may also include the stationary unit (SU) described in U.S. Ser. No. 10/460,458 which cooperates with the PU. For brevity this RCD unit will be sometimes called simply "RCD", but it will be remembered that "RCD" stands for "RCD™ unit"
  mCS refers to master central station;
  pCS refers to peripheral central station;
  mMP refers to master medical professional, a medical professional located in the master central station; and
  pMP refers to peripheral medical professional, a medical professional located in the peripheral central station.
  NA refers to network administrator, a person who may a) serve to match an emergency call from an RCD to an MP, and/or b) may perform various non-matchmaking tasks including scheduling, software and hardware management and system monitoring.
  the plural version of any of the aforementioned defined terms is formed by simply adding a lower case 's' Thus "peripheral central stations" is indicated by "pCSs."

Not infrequently, pMP and pCS are used nearly interchangeably in the text which follows. Although, as indicated above, they have distinct definitions, the statement that information flows from RCD unit to pCS is intended to mean the same as stating that information flows from this unit to pMP.

"RCD unit" in the current application may refer to the same device(s) as either the PU or the PU-SU combination in U.S. Ser. No. 10/460,458.

The word "computer" is, at times, used interchangeably with pCS, and, when used as such is intended to indicate any adequately equipped computational device (including laptop computers, desktops, palm-sized devices, trio-type devices or cellular "telephone"). "Adequately equipped" implies having adequate user interface features, and containing and having the capability of running appropriate networking software.

The male gender has been selected to refer to all personnel, such as MPs, enablers, etc., with the understanding that such selection is arbitrary and in no way indicates a preference or implies a difference in ability to perform tasks as compound to the female gender.

The terms "911" or "9-1-1" and emergency medical teams are generally used interchangeably.

SUMMARY OF THE INVENTION

The present invention concerns improvements to the system and method disclosed in the aforementioned published U.S. patent application No. 10/460,458.

1) A system and method for displaying all vital central station information and controls on a single screen, e.g. a laptop, "trio," or "palm-pilot," or even a smaller screen such as that of a cellular phone; Alternatively, the information may be displayed on the visor of a helmet or a windshield or other "heads-up" display.

2) System and method for linking pCSs to the mCS.

3) A system and method for operating the system disclosed in U.S. Ser. No. 10/460,458, without MPs in the mCS. The mCS contains one or more network administrators, who do not make and/or execute medical decisions.

4) A system and method for operating the system disclosed in U.S. Ser. No. 10/460,458 without any mCS.

5) A method for automatic call allocation using the systems and methods indicated above.

6) Systems and methods of linking an RCD unit to an arrest sensor.

7) A system and method of maintaining an RCD unit in a motor vehicle.

8) A system and method of linking an RCD unit to a vehicle communications system.

9) A system and method of linking an RCD unit to a CS through a network of either: a) non-vehicle-based SUs, b) vehicle-based SUs/vehicle communication systems, or c) non-vehicle-based SUs and vehicle-based SUs/vehicle communication systems.

10) System and method of using RCD with a chest compression device.

11) System and method for using the network of RCD units and MPs for disaster monitoring and management.

12) Method of monitoring and treating hospital patients, "rehab" (rehabilitation center/program) patients, out-of-hospital emergency patients, patients with non-cardiac implanted devices and impaired drivers using RCD units, modified RCD units and MPs.

For a full understanding of the present invention, reference should now be made to the following detailed description of the preferred embodiments of the invention as illustrated in the accompanying drawings.

BRIEF DESCRIPTION OF DRAWINGS

FIG. 2A shows a block diagram of the Peripheral Central Station.
FIG. 19I shows a Camera for sensing victim fall and/or change in cardiac and/or respiratory status and devices for processing this information.
FIG. 27A shows a Rectangular CPR Box, unfolded.

DESCRIPTION OF THE PREFERRED EMBODIMENTS

Figure 1A:
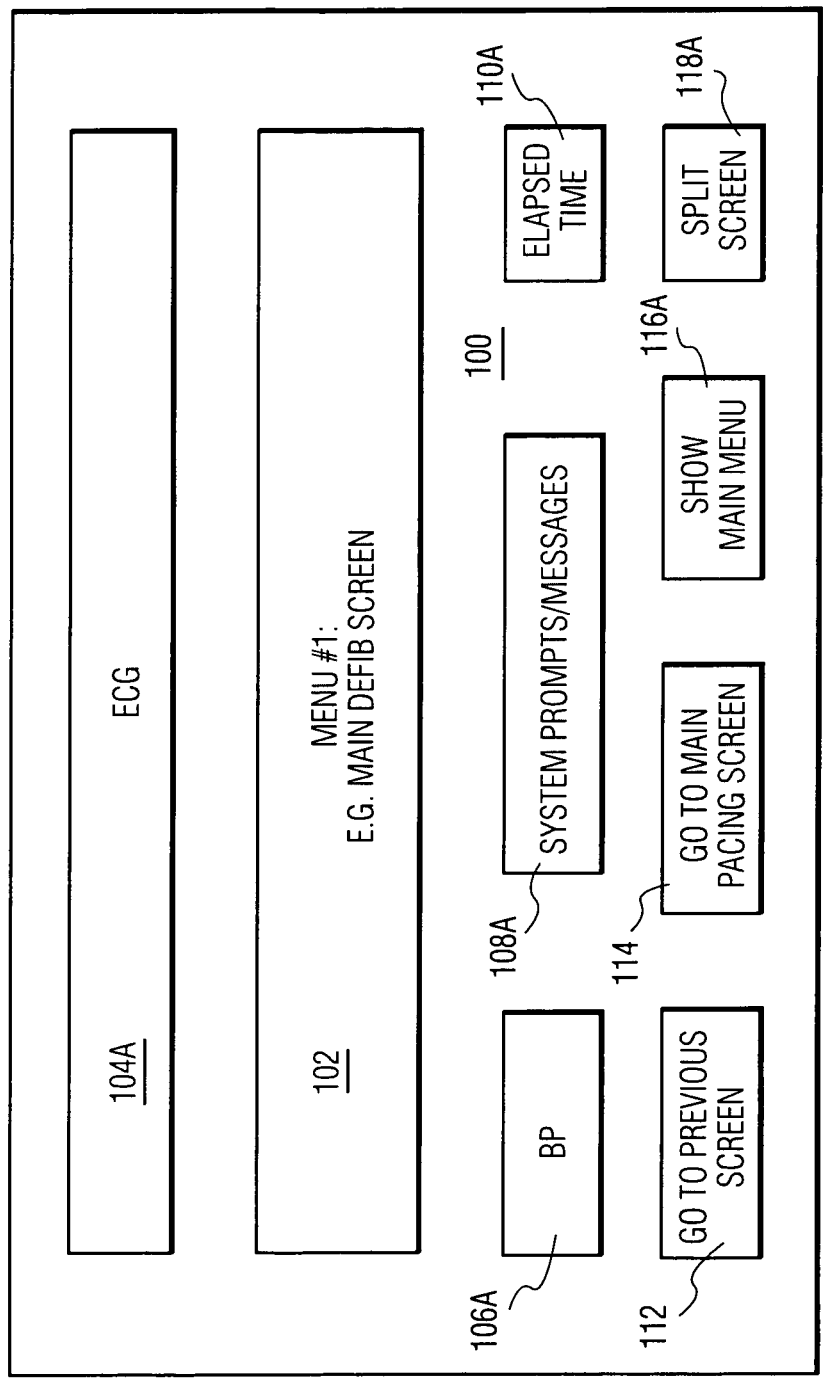
FIG. 1A shows a pMP display Screen with a Single Menu.

The preferred embodiments of the present invention will now be described with reference to FIGS. 1-37 of the drawings. Identical elements in the various figures are designated with the same reference numerals.

Overview of Inventions (FIGS. 1-18)

The advantages of "decentralizing" the central stations are:
1) Big cost savings. No need to have a large collection of 24/7 people all in one place. Less overhead (the building, etc), or, in the case of no central station, much less overhead.
2) Ability to bring people on-line during busy times. They would be paid an "on call" lesser salary when not actually working. Another potentially big cost savings.
3) The ability to use and/or partner with an existing call center which may or may not have medical sophistication but could be usable in terms of its hardware and for a screening and/or routing functions (see below).

Two ways of presenting an overview of the structure of a system which decentralizes central station function are in terms of a) functionality and b) connectivity.

The "functionality" approach considers a number of formats, each with a progressively more limited role for the master central station (mCS):
 a) The mCS handles all calls. This is discussed in U.S. Ser. No. 10/460,458;
 b) The mCS handles some calls, and when it's capacity is exceeded, peripheral central stations (pCSs) are commanded to be available for service. This is discussed in Approach 1, below;
 c) The pCSs are part of the call handling approach, even when the mCS is not "saturated" with volume. This is discussed in Approach 2, below;
 d) The mCS handles no arrest management, but has a number of support functions including the screening of calls, assignment of calls to pCSs, etc. (See list of 5-6 functions under "Approach 2," below.). This is discussed in Approach 2, below;
 e) The mCS handles nothing but call routing/matchmaking: i.e. making sure that each incoming call is assigned to an available pMP. This is discussed in Approach 2, below;
 f) There is no mCS. The system of RCDs and pMPs handles routing, staffing etc. This is presented in Approach 3, below.

The connectivity approach considers the nature of the connections among each of a) the RCDs, b) the pCSs, and c) the mCS [if any]. Connections are considered in terms of a) the components which are connected, and b) the medium over/through which the connection takes place.

The broad connectivity formats are:
 a) All RCD-pCS communication passes through the mCS;
 b) The RCD initially contacts the mCS. The mCS then assigns an available pCS. The RCD then contacts and communicates directly with the assigned pCS (or the assigned pCS contacts and communicates directly with the RCD).
 c) There is no mCS. The RCD finds an on-duty pCS.

Connections may be made using:
 a) one or more public telephone companies;
 b) radiofrequency/wireless technology;
 c) the internet;
 d) a private communications network;
 e) combinations of the above.

Approach (1): Peripheral Central Stations are Only for Overflow

The Master Central Station (mCS) handles arrests and Peripheral Central Stations (pCSs) may be brought on line for either overflow cases which the mCS is not adequately staffed to handle, or in the event that there is an equipment failure involving the mCS.

Approach (1): Shown in FIGS. 3A and 3B. All portions of any call from a RCD to a pCS go through the master central station. This is shown in FIG. 57 of U.S. Ser. No. 10/460,458, and is discussed in the associated detailed description paragraphs 2382-2390 of U.S. Ser. No. 10/460,458 and claims 173-178 of U.S. Ser. No. 10/460,458.

Approach (1B): Shown in FIGS. 4, 5A and 5B. The call initially goes to the mCS. Next the mCS provides the RCD with an address (either internet, cell phone number or private communications network) for a pCS, and/or provides the pCS with the RCD address. This is followed by a communications link between RCD and pCS which does not "go through" the mCS.

Approach (2): Peripheral CSs are Not Just for Overflow

Shown in the same figures as Approaches (1A) and (1B). Peripheral CSs (pCSs) are not just for overflow during busy times or equipment failures at the mCS (Approach (1) uses the peripheral CSs only for overflow and equipment failure). Most or all of the arrest management would be handled by solo medical professionals, "sMPs" using desktops, laptops, palm devices or even cell phones. (All sMPs are peripheral MPs, i.e. pMPs.) There would be a Master Central Station whose functions include one or more of:

(a) screening calls (i.e. non-arrests do not get passed on to pCSs);
(b) the assignment of a particular call to a particular CS;
(c) staffing: making sure that at all times, the number of on-duty, and on-call MPs was sufficient;
(d) calling the local 9-1-1; and
(e) RCD maintenance (both live and on-line).

As indicated above, a sixth (optional) function of the mCS would be do some of the work of actually managing cardiac arrests (with the majority handled by sMPs in pCSs.

The ultimately "stripped-down" version of the Central Station is one in which the CS only performs a routing function [(b), above]. There would be no call screening, and calling 9-1-1 would be handled by the sMP. RCD maintenance could be outsourced and/or a separate stand-alone center.

Approach (3): No Central Station.

Figure 6A:
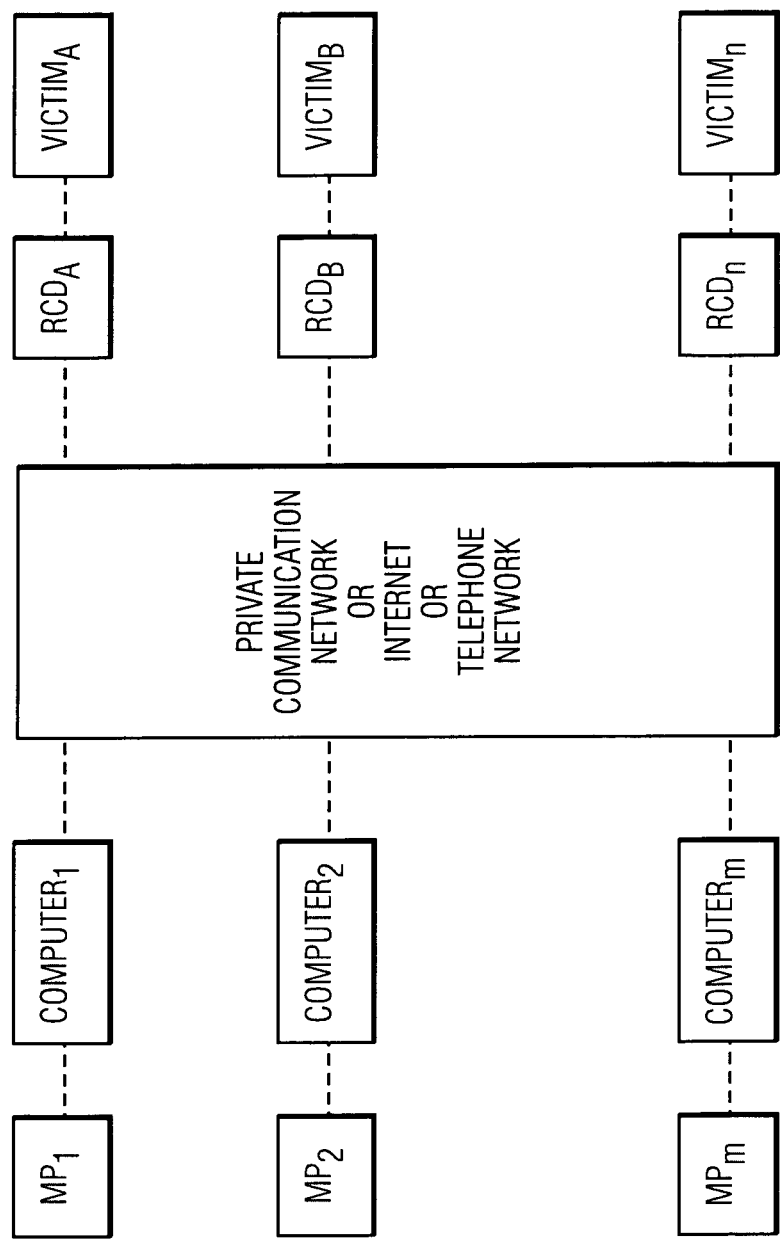
FIG. 6A shows a block diagram of a third type of system architecture. No master central station and no network administrator. Signals are transmitted via a private communications network, the internet or a telephone network.
Figure 6B:
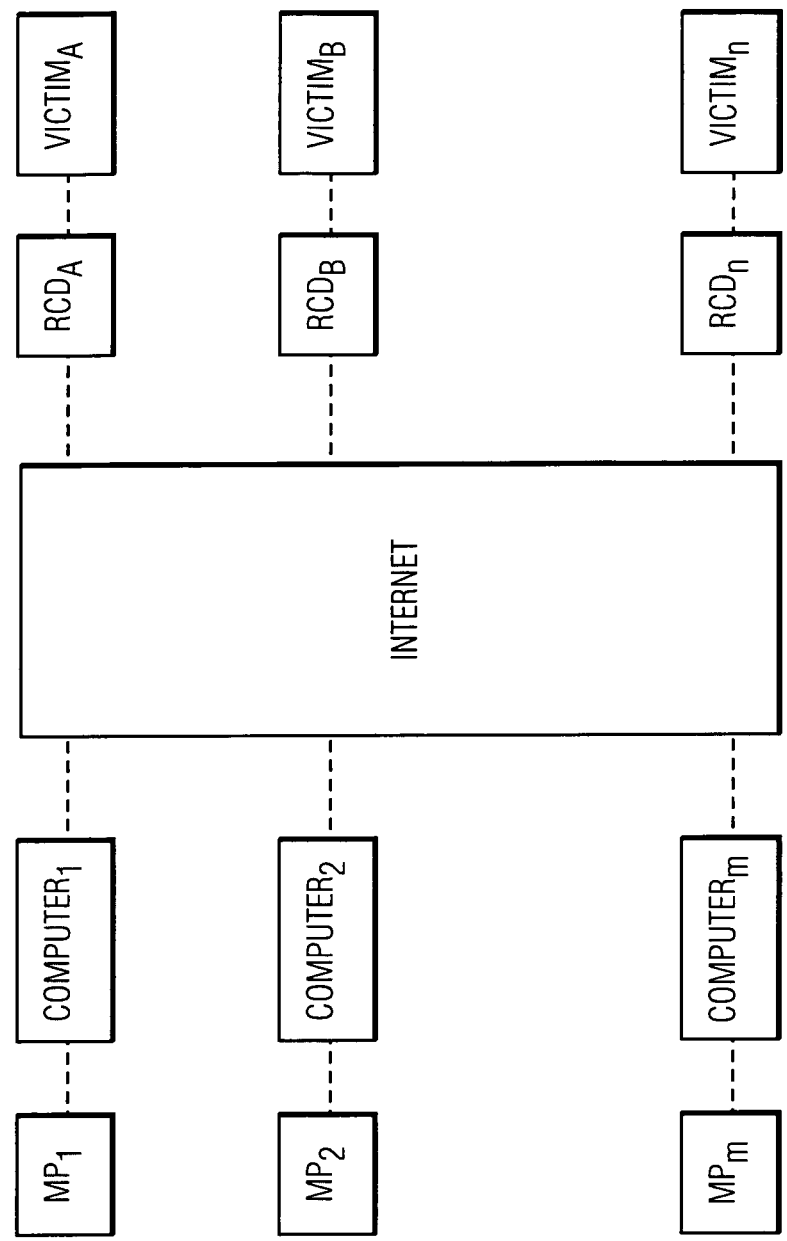
FIG. 6B shows a block diagram of the third system architecture III with internet links.
Figure 6C:
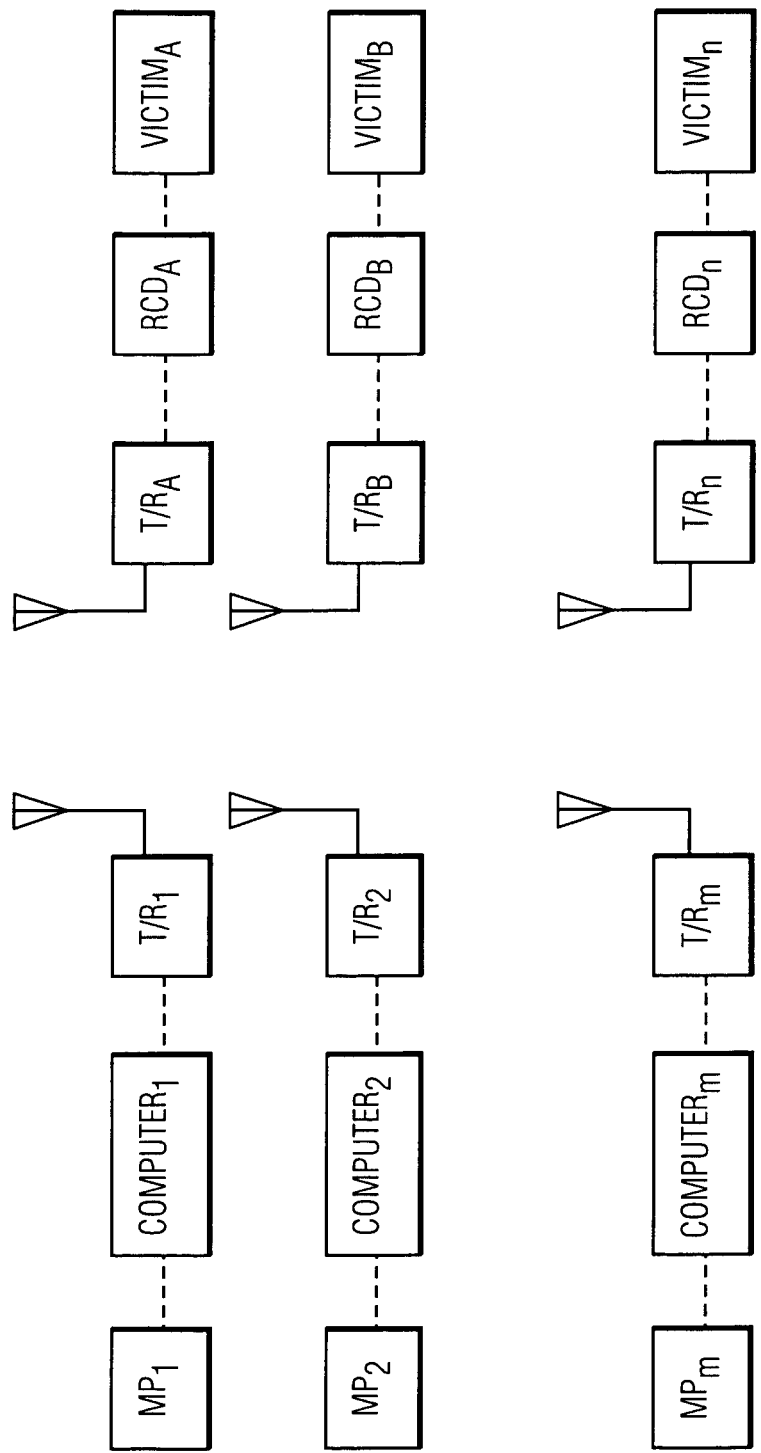
FIG. 6C shows a block diagram of the third system architecture with RF links.

Shown in FIGS. 6A, 6B and 6C. There are many ways in which a RCD with a user needing assistance could find an available pCS:

Each RCD could have the address of each peripheral CS. In the event of an arrest, the RCD would start going through its list of potential pCSs looking for an on-duty/not occupied pCS. This could occur very quickly. In another variation each RCD could have the address and "on call" schedule of each pMP, thereby limiting the number of contact attempts.

Alternatively, the RCD could simultaneously try to contact many pCSs, but once a single successful RCD-pCS handshake occurs, the simultaneous requests to other pCSs would be cancelled. Each CS could have the equivalent of an "off duty" indicator and a "busy" indicator.

Alternatively, the RCD could contact a network of pCSs, whose sMPs' schedules are such that one or more sMPs is always available to take a call. (The pCSs within a network would not necessarily be geographically near each other). The purpose of the networks is to guarantee the availability of a free MP. Each pCS would have routing/searching capability: Algorithms are loaded onto each pCS which let it hunt among, say 10 or 100 other pCSs so that if it is unavailable to take a call, it searches these 10 or 100 for an available call-taker. If the number of free MPs on the network falls below a certain number, a) "on-call"/reserve MPs, i.e. MPs who are off-duty, but are available to come on-duty immediately, when requested (who may be on the same or on another network) are contacted (e.g. by telephone, beeper, on-screen message, etc.) and asked/commanded to come on-line; or b) calls are routed to another network of pMPs. Activating these reserve MPs may be triggered by a) a low population of free MPs on a particular network, and/or b) a low population of free MPs on the entire system (i.e. all networks combined). The approach using reserve MPs could also be used in conjunction with the "stripped down" version of Approach (2), above.

Alternatively, each pMP who is both "on duty" and not busy could send a frequently updated status signal to either every RCD, or a subset of the RCDs, so that if the RCD user requests assistance, the RCD has an updated list of available pMPs.

There could be a system administrator whose functions would include:

a) updating each RCD's list of pCSs/pMPs, as new pMPs are hired; and
b) making sure that enough pMPs are on duty/available at any one time, given the varying call volume.)

Alternatively, these two functions could occur without an administrator:

a) [updating function] Each newly available pCS/pMP could make his status known to some or all of the RCDs, without an administrator.
b) [assuring that there are enough pMPs] In the event that all or nearly all of the capacity of a sub-network of pMPs is used, the system could contact "on call" pMPs, i.e. pMPs who are not actually on-duty, but are available to come on-duty during high system usage periods. No on-duty MP would, for example, be allowed to switch his status from on-duty to off-duty unless there were at least, say, four (or 20) other free pMPs. This embodiment could also be used in conjunction with the "stripped down" version of Approach (2), above.

As in the case (immediately above) of the "stripped down" CS, there would be no call screening, calling 9-1-1 would be handled by the sMP, and RCD maintenance could be outsourced and/or performed by a separate stand-alone center.

Detailed Description of Inventions 1-5 (FIGS. 1-18)

Figure 1B:
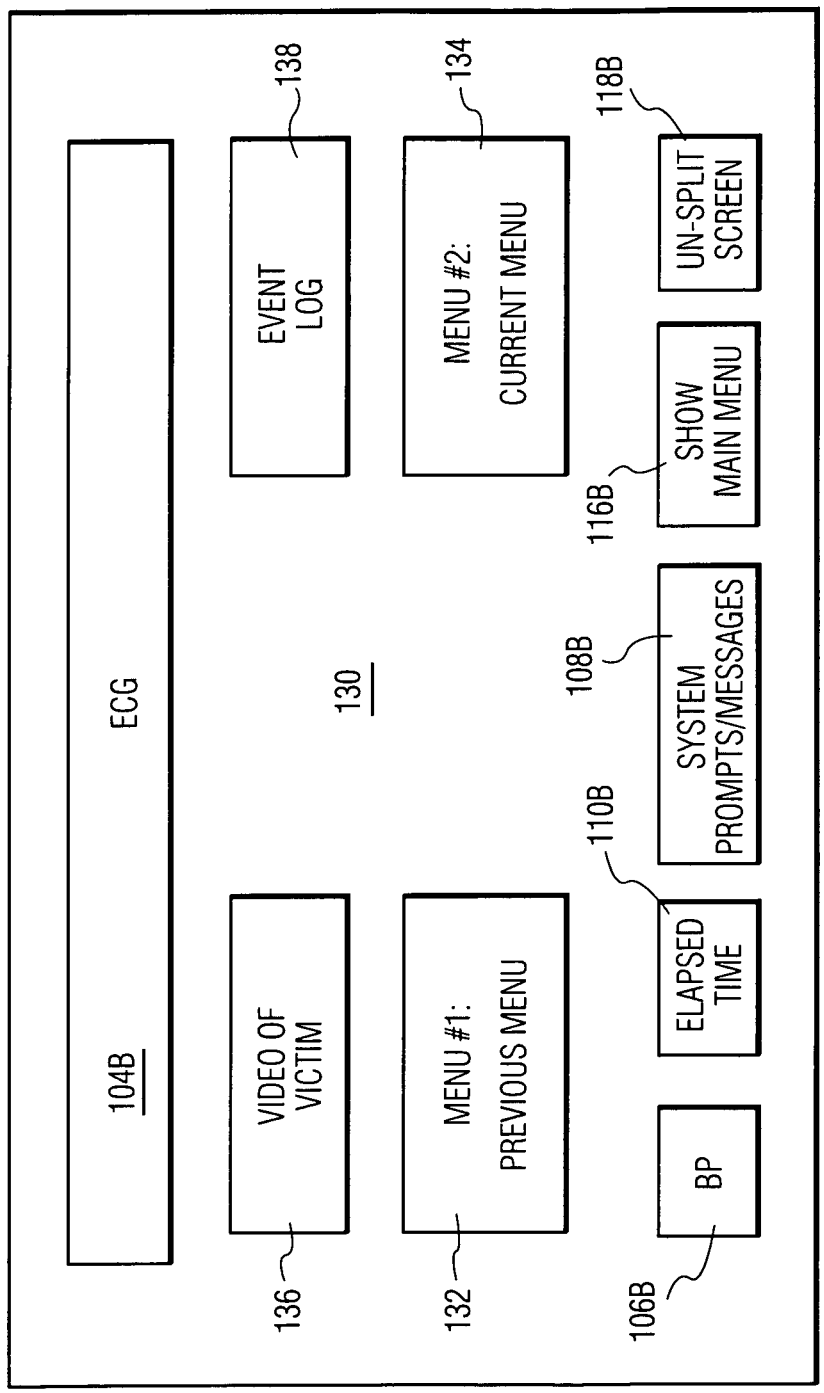
FIG. 1B shows a pMP display Screen with Four Views.

FIGS. 1A and 1B show possible screens that would allow a medical professional to monitor and/or control an actual or potential cardiac emergency, medical emergency, other emergency. These screens are set up to allow the MP to work from a single screen, rather than from a bank of screens. (Control using a bank of screens is shown in FIG. 3 of U.S. Ser. No. 10/460,458.)

Figure 33:
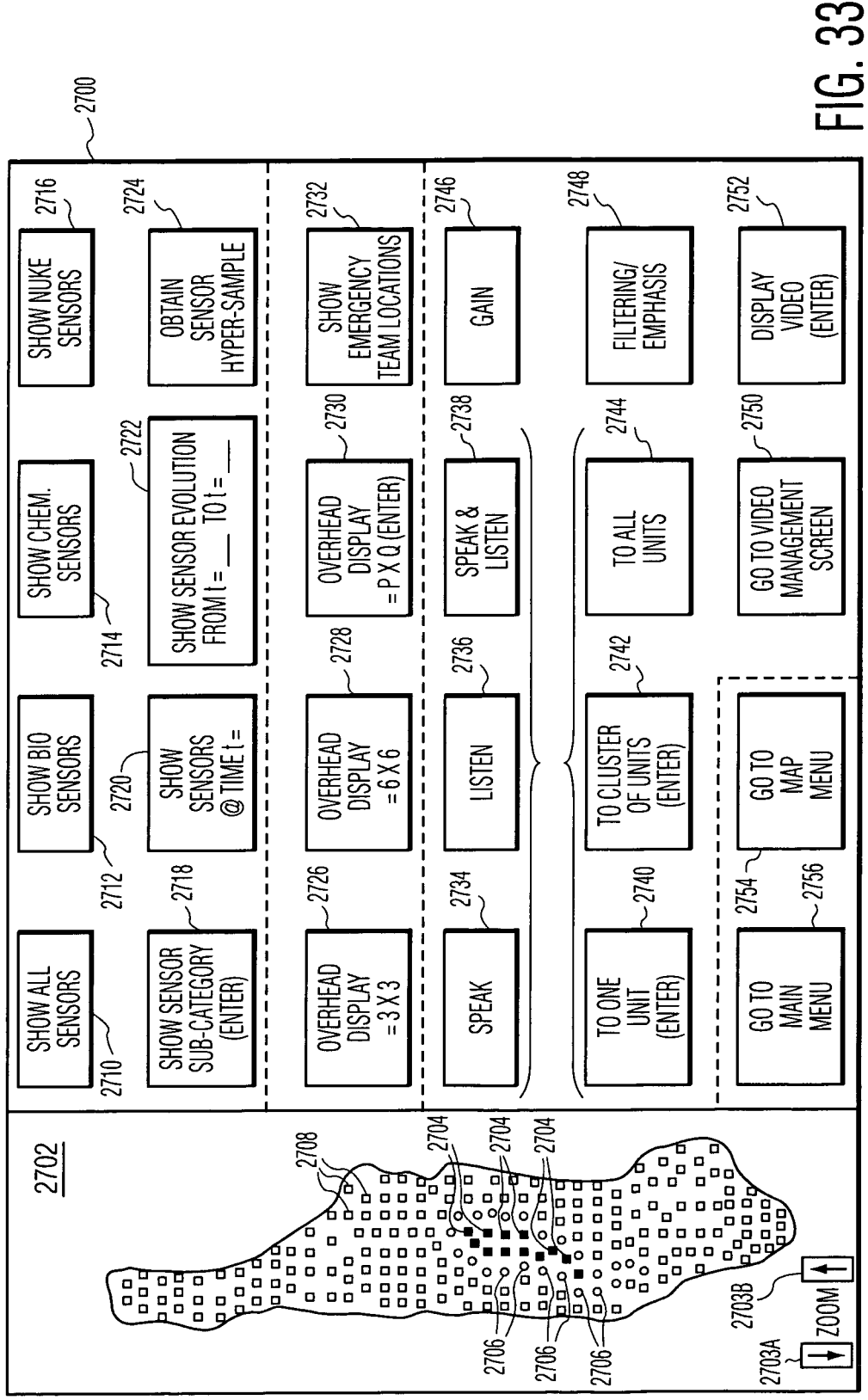
FIG. 33 shows a Disaster monitoring screen.

Referring to FIG. 1A, 100 is a screen which shows the display of a single menu 102, the Main Defibrillation Menu (shown in FIG. 33 of Ser. No. 10/460,458), which allows the MP to select defibrillation shock parameters. These may be selected using any one of a number of technologies as are known in the art including but not limited to point and click, a "touch" methodology, or "hot keys."

Various items which may be displayed on the screen include:

a) a streaming ECG 104A;
b) the victim's blood pressure 106A;
c) system prompts and messages 108A (e.g. management suggestions, changes in communication status, location and time-to-arrival of emergency medical personnel, etc.); and
d) elapsed time 110A since the start of the emergency.

On-screen navigational options for the MP include:

a) 112, going back to the previously displayed screen;
b) 114, going to the main pacing screen;
c) 116A, Showing (e.g. superimposed on a portion of 102 and/or 104) or going to the main menu (shown in FIG. 43 of U.S. Ser. No. 10/460,458); and
d) 118A, splitting the screen.

The screen split may be such that two menus are simultaneously displayed (in any possible geometric arrangement, e.g. side by side, or one above the other), or such that three or more menus are simultaneously displayed (in any possible geometric arrangement).

FIG. 1B shows an example of a possible MP screen 130 which is split to show four images including two menus and two informational panels. In this format, the right lower panel 134 displays the menu under current use by the MP, and the left lower panel 132 displays the menu previously used. When the MP selects a new menu, the contents of the panel 134 move to panel 132, and the new menu is displayed on the lower right on panel 134.

FIG. 2A, showing a peripheral "central station," is adapted from FIG. 49 of U.S. Ser. No. 10/460,458. Operation of the non-numbered elements is as described in U.S. Ser. No. 10/460,458. However, the central station unit which a peripheral MP uses, differs from a master central station in that all of the information is displayed on a single non-touch-sensitive screen 150. Multiple screens may be merged (as discussed in reference to FIG. 1B) using screen management software 152.

Because the screen in a preferred embodiment is non-touch-sensitive, the MP must input his choices via either a mouse, or keyboard selection. Other possible inputs include speech (using voice recognition software as is known in the art), and a touch sensitive screen. It is also possible that a pCS could include more than one screen. Embodiments of the system without multiple simultaneous MP screens (i.e. screens as shown in FIGS. 25-43 of U.S. Ser. No. 10/460,458) merged onto a single pCS screen (i.e. the current application FIG. 1A format, not the current application FIG. 1B format) are possible.

As discussed below, the pCS may be part of a network of pCSs, in which case a networking program 154 (described below) will allow it to navigate properly. If the RCD is part of a network which is non-centralized, i.e. either has no administrator, or has an administrator who is not responsible for assigning individual calls, the RCD will contain the addresses 156 and schedules 158 of other pMPs. These will be updated from time to time (as described below). The addresses may be internet addresses, radio frequencies, or telephone numbers.

Figure 2B:
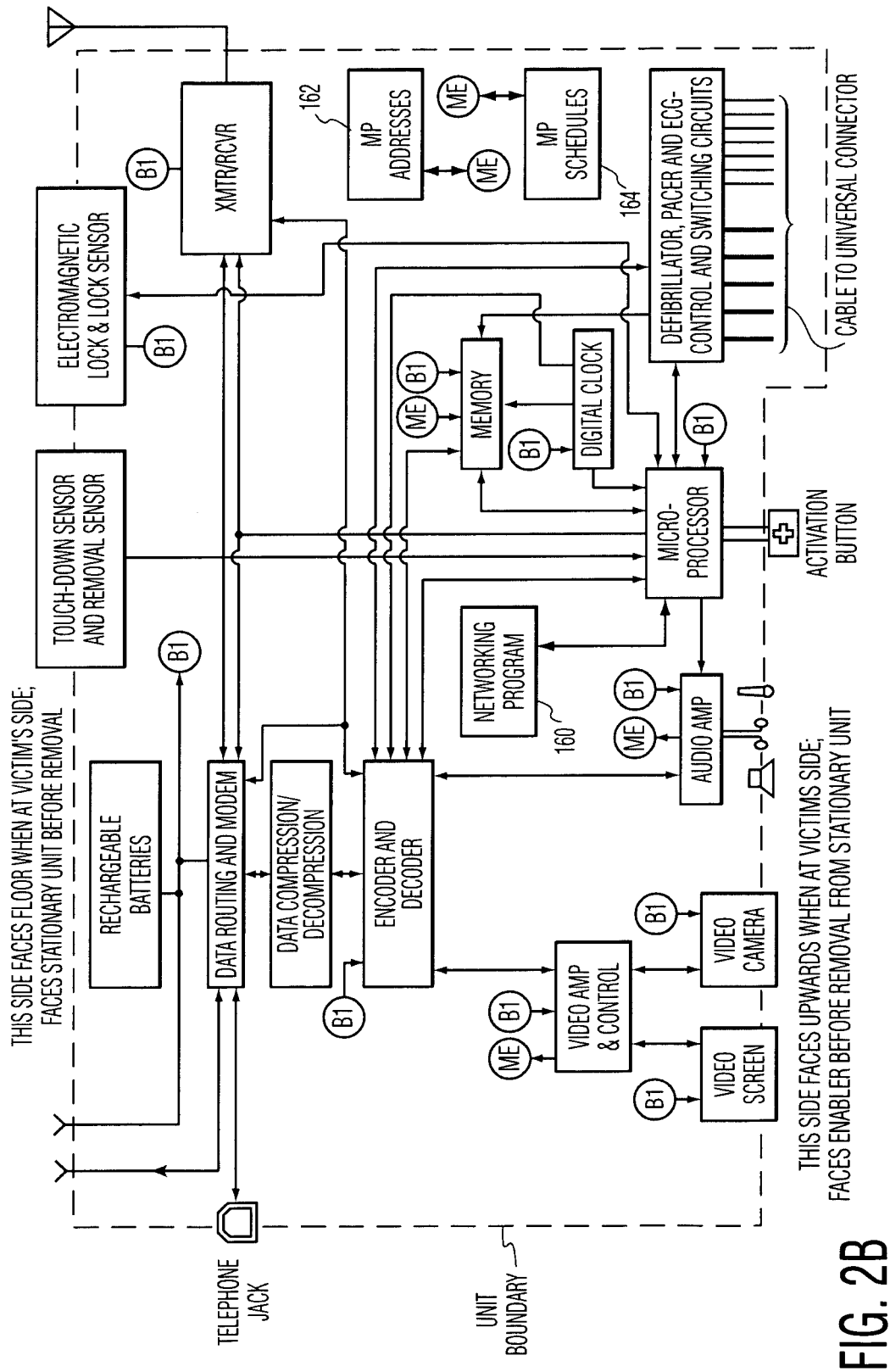
FIG. 2B shows a block diagram of the RCD unit.

FIG. 2B, showing a RCD, is adapted from FIG. 46 of U.S. Ser. No. 10/460,458. Operation of the non-numbered elements is as described in U.S. Ser. No. 10/460,458.

As discussed below, the RCD may communicate directly with a network of pCSs (i.e. without an intervening "traffic directing device" [TDD] or "traffic directing person" [TDP]), in which case a networking program 160 will allow the RCD to navigate the system properly. If the RCD communicates with such a non-centralized network (which either has no administrator, or has an administrator who is not responsible for assigning individual calls), the RCD will contain the addresses 162 and schedules 164 of pMPs. These will be updated from time to time (as described below). The addresses may be internet addresses, radio frequencies, or telephone numbers.

Figure 3A:
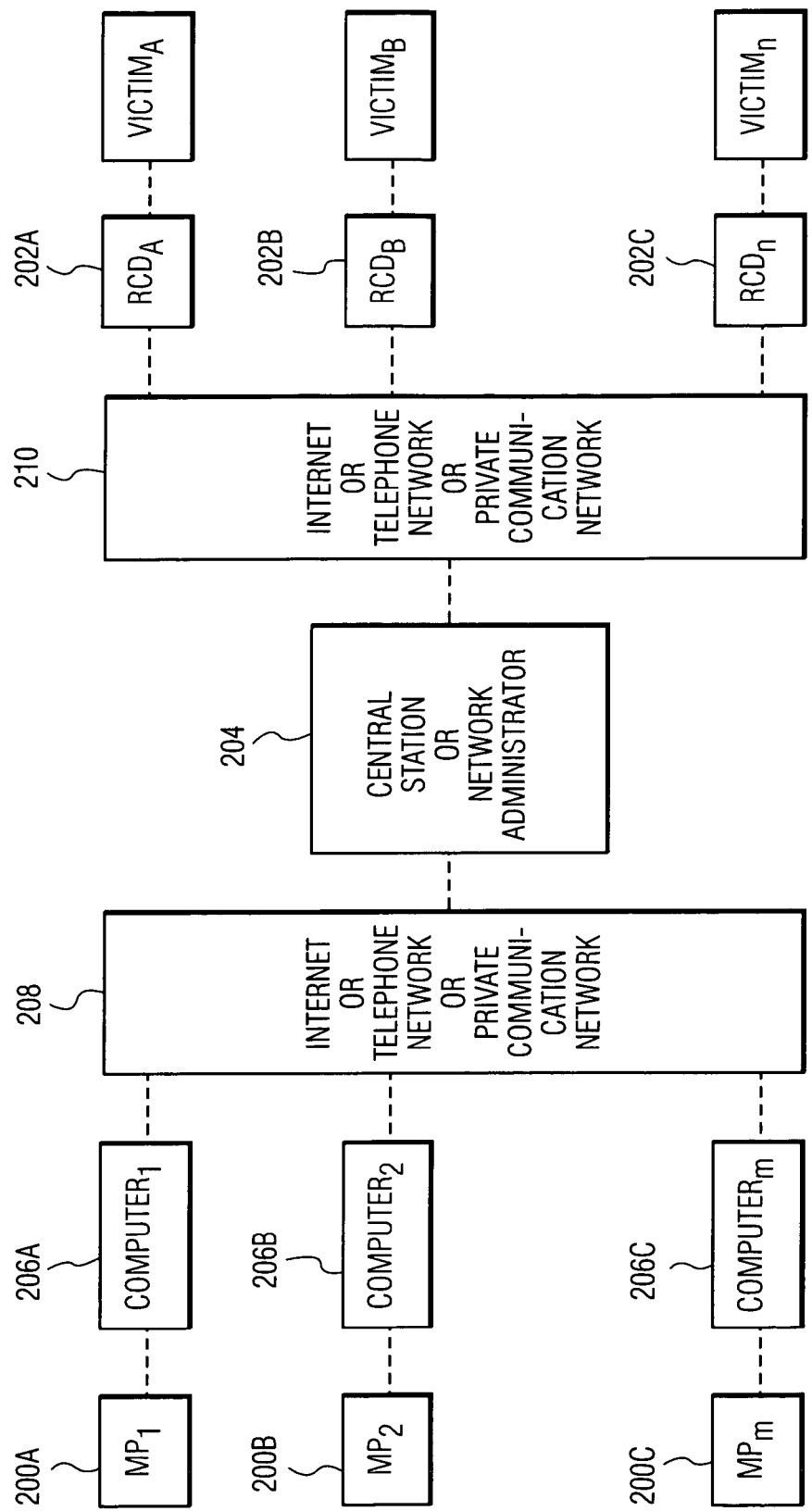
FIG. 3A shows a block diagram of the system of architecture with Victims linked to pMPs through mCS.

FIG. 3A shows system architecture type I, in which all communication between MPs 200A-C and RCDs 202A-C is via a central focus 204 whose functional capacity may range from
a) the type of full-function central station described in U.S. Ser. No. 10/460,458 (in which case the pCSs may either i) handle overflow cases not able to be handled by the mCS, or ii) handle a portion of the mCS incoming calls, even in a non-overflow situation); to
b) a central station which handles the overflow which cannot be handled by the pCSs; to
c) a station without any MPs, but which has a TDD or TDP which assigns incoming calls to pMPs. Hereinbelow, the TDP is at times referred to as a "Network Administrator," [NA], but this latter term is at times used to describe a person who has system maintenance responsibilities which do not include call assignment.

The MPs 200A-C are linked via their respective computers 206A-C to 204 via a communications network 208 which may be either
a) the internet;
b) a telephone system;
c) a private communications network; or
d) a hybrid system which has elements of at least two of a)-c).

204 is linked to RCDs 202A-C via a communications network 210 which may be either
a) the internet;
b) a telephone system;
c) a private communications network; or
d) a hybrid system which has elements of at least two of a)-c).

208 may or may not be the same type of medium as 210.

Figure 3B:
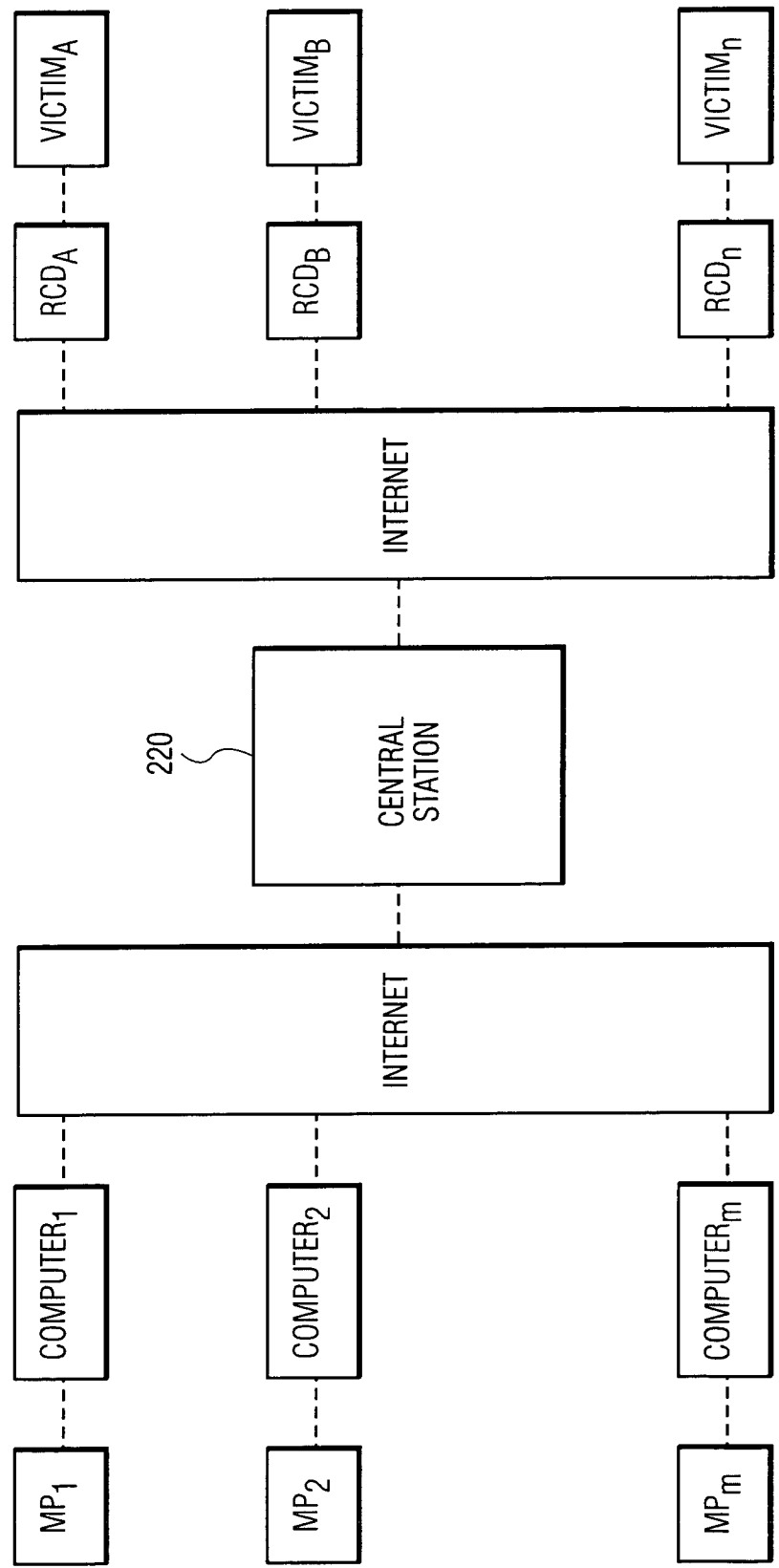
FIG. 3B shows a block diagram of a system of architecture I with internet linkages.

As an example, FIG. 3B shows an embodiment in which a central station 220 is linked to MPs and RCDs via the internet.

Figure 4:
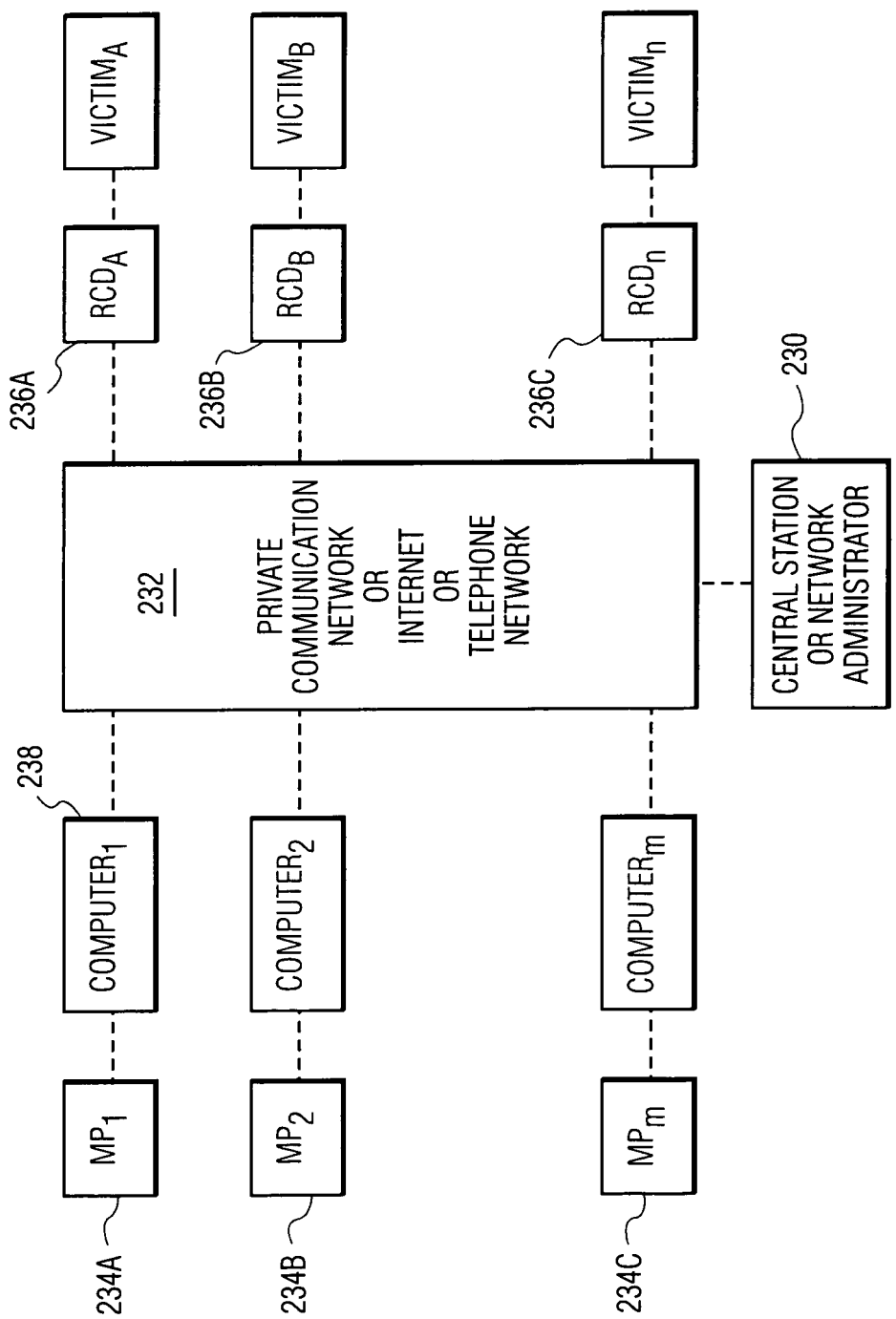
FIG. 4 shows a block diagram of the architecture with Victims linked to pMPs without going through mCS.

FIG. 4 shows a system in which CS/NA 230 is linked to a communications network, but in which information flow between MPs 234A-C and RCDs 236A-C may or may not pass through or involve 230. Three modes of operation are possible:
a) A RCD contacts 230, needing to be assigned to a MP. 230 gives the RCD the address (internet, phone number, or frequency) of a pMP, after which the RCD uses that address to communicate directly (between the RCD and the pMP), via 232;
b) A RCD contacts 230, needing to be assigned to a MP. 230 "connects" the RCD to the appropriate pMP, but for the duration of the call, all communication passes through 230; or
c) A RCD directly communicates with a pMP's computer 238, via 232.

Figure 5A:
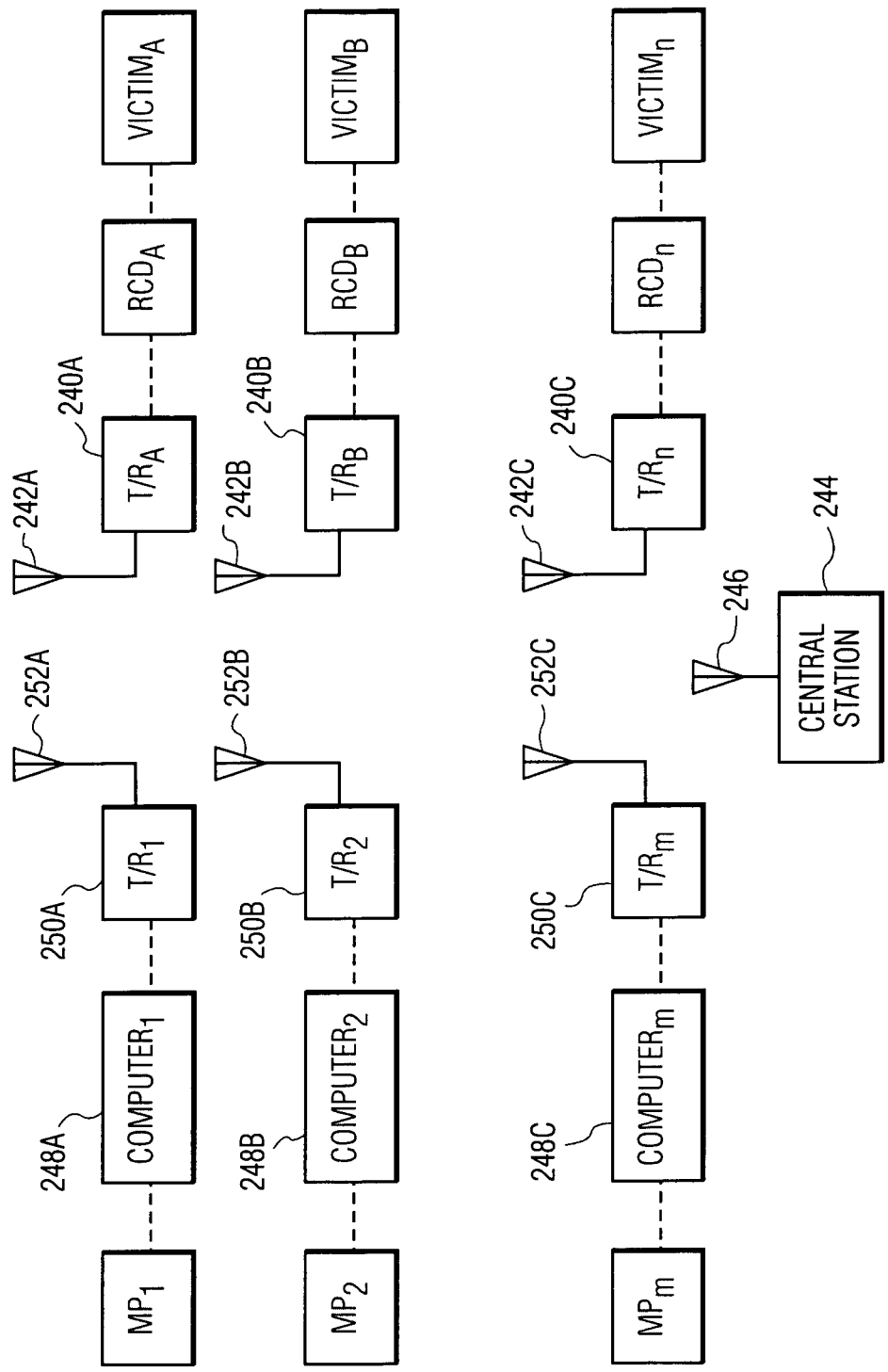
FIG. 5A shows a block diagram of the system architecture with RF links. Either all $T/R_m \leftarrow \rightarrow T/R_n$ signals go through the mCS (architecture I) or some $T/R_m \leftarrow \rightarrow T/R_n$ signals go directly from $T/R_m$ to $T/R_n$ (architecture II).

FIG. 5A shows a system in which all communication is via radiofrequency (RF) transmission/reception. Each RCD is linked to a transmitting and receiving [T/R] device 240A-C, which communicates via its respective antenna 242A-C. As was the case discussed in conjunction with FIG. 4, hereinabove, the aforementioned T/R device-antenna combinations may either:
a) communicate with CS 244 via antenna 246 (the first two modes of operation described in the previous paragraph); or
b) communicate with MP computers 248A-C via T/R devices 250A-C, via antennae 252A-C.

Figure 5B:
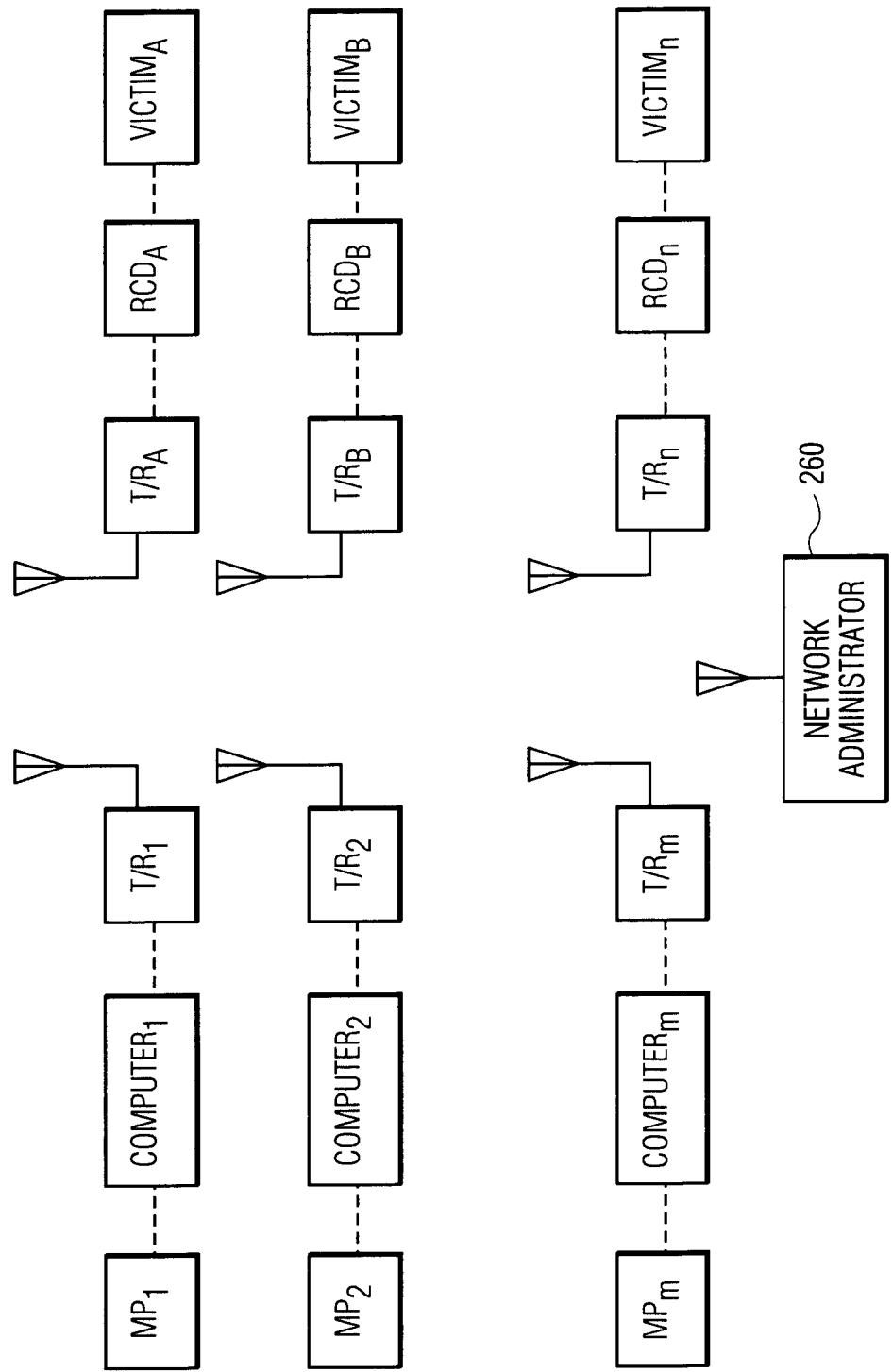
FIG. 5B shows a block diagram of the system architecture with RF links. Either all $T/R_m \leftarrow \rightarrow T/R_n$ signals go through the network administrator (architecture I) or some $T/R_m \leftarrow \rightarrow T/R_n$ signals go directly from $T/R_m$ to $T/R_n$ (architecture II).

FIG. 5B shows a system which is similar in architecture to that of FIG. 5A except for the substitution of NA 260 for CS 244 (of FIG. 5A). NA function may or may not include call assignment.

FIG. 6A shows a class of systems in which there is no central station or network administrator. The methods by which a RCD "finds" the appropriate MP is discussed below. The geometrical distribution within the figure, in which there is one RCD on the right side of the figure for each MP and associated computer on the left, is not intended to indicate a 1:1 relationship between RCDs and MPs.

FIG. 6B shows a specific example in which MP computers (i.e. the pCSs) and RCDs are linked via the internet.

FIG. 6C shows another specific example in which communication occurs via T/R devices and associated antennae at each end.

Figure 7A:
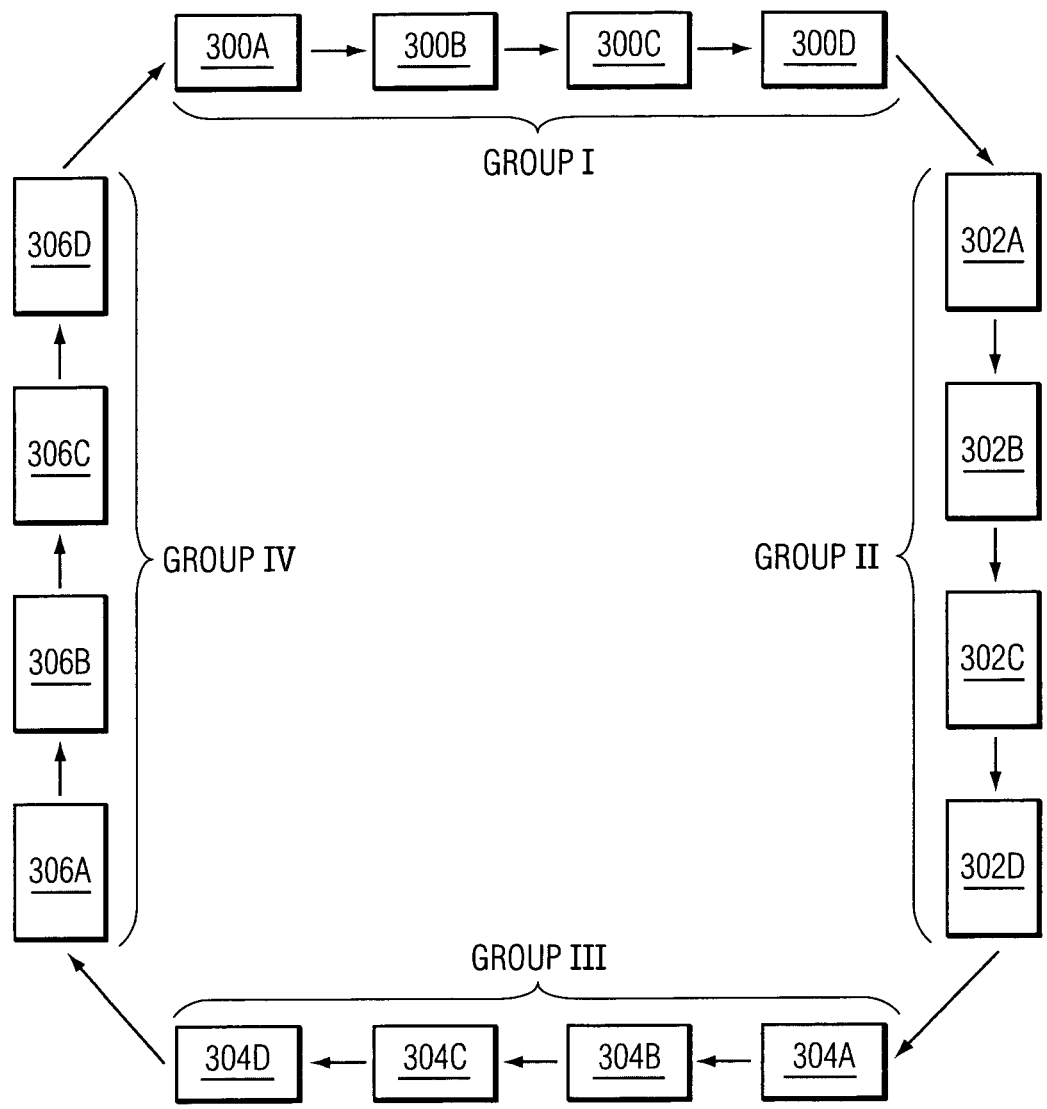
FIG. 7A shows a block diagram of the Network of peripheral Medical Professionals.

FIG. 7A shows a network of peripheral MPs using peripheral CSs. In the figure, each pCS (300A-D, 302A-D, 304A-D, 306A-D) is linked to two neighbors (e.g. 300D is linked to 300C and 302A) as shown. The links are indicated by arrows in the FIG. and may be the internet, a telephone system or radiofrequency. Although a ring-shaped network is shown in the figure, other network topologies (e.g. star, hybrid) are also possible. The network is shown consisting of four groups of four MPs, which is more robust than networks with smaller numbers of groups in terms of scheduling and ability to handle call volume fluctuations. However, other numbers of groups (larger or smaller), other groups sizes (larger or smaller), and non-uniform group size is possible (i.e. groups with different numbers of member pCSs). A possible pMP set of schedules is shown below in Table 1:

TABLE 1

POSSIBLE MP SCHEDULES
NETWORK CONSISTING OF FOUR GROUPS
30 MINUTE OVERLAP

| GROUP I | GROUP II |
|---|---|
| M 8 a - M 7 p | M 6:30 p - T 5:30 a |
| W 2 a - W 1 p | W 12:30 p - W 11:30 p |
| R 8 p - F 7 a | F 6:30 a - F 5:30 p |
| SA 2 p - SU 1 a | SU 12:30 a - SU 11:30 a |

| GROUP III | GROUP IV |
|---|---|
| M 8 a - M 7 p | M 6:30 p - T 5:30 a |
| W 2 a - W 1 p | W 12:30 p - W 11:30 p |
| R 8 p - F 7 a | F 6:30 a - F 5:30 p |
| SA 2 p - SU 1 a | SU 12:30 a - SU 11:30 a |

NOTES:
1) Each MP works a 44 hour week, consisting of four 11 hour shifts.
2) After having had two shifts off, the MP is in the "first reserves," (level 1B reserves [explained hereinbelow]).
3) After having had one shift off, the MP is in the "second reserves," (level 2A reserves [explained hereinbelow]).
4) During the shift which follows the one in which the MP worked, the MP is in the "third reserves," (level 2B reserves [explained hereinbelow]).

Other features of network architecture are:
a) The ring structure is maintained at all times. This means that either i) all computers on the ring are always operative (even if unattended) to pass information between it and it's neighbors, or, ii) if a computer is removed or turned off, the network simultaneously is "repaired" by having the two neighbors of the turning-off-computer, link with each other.
b) One of the members of the network may be designated as the "key" member, i.e. the one which interfaces with all out-of-network entities. It is the member which first receives all incoming calls (from the internet or another communications medium), and it is the member which links to other networks, if any. Alternatively, two or more (or all) other members of the ring may receive incoming calls (For example, some RCDs may have the address of 300A as their primary call target, while other RCDs may have 300B as the primary address.), and two or more (or all) other members of the ring (not necessarily the same as the two or more receiving incoming calls) may link to other networks.
c) If there is a particular network member selected as the key network member, that designation may change from time to time.

Figure 7B:
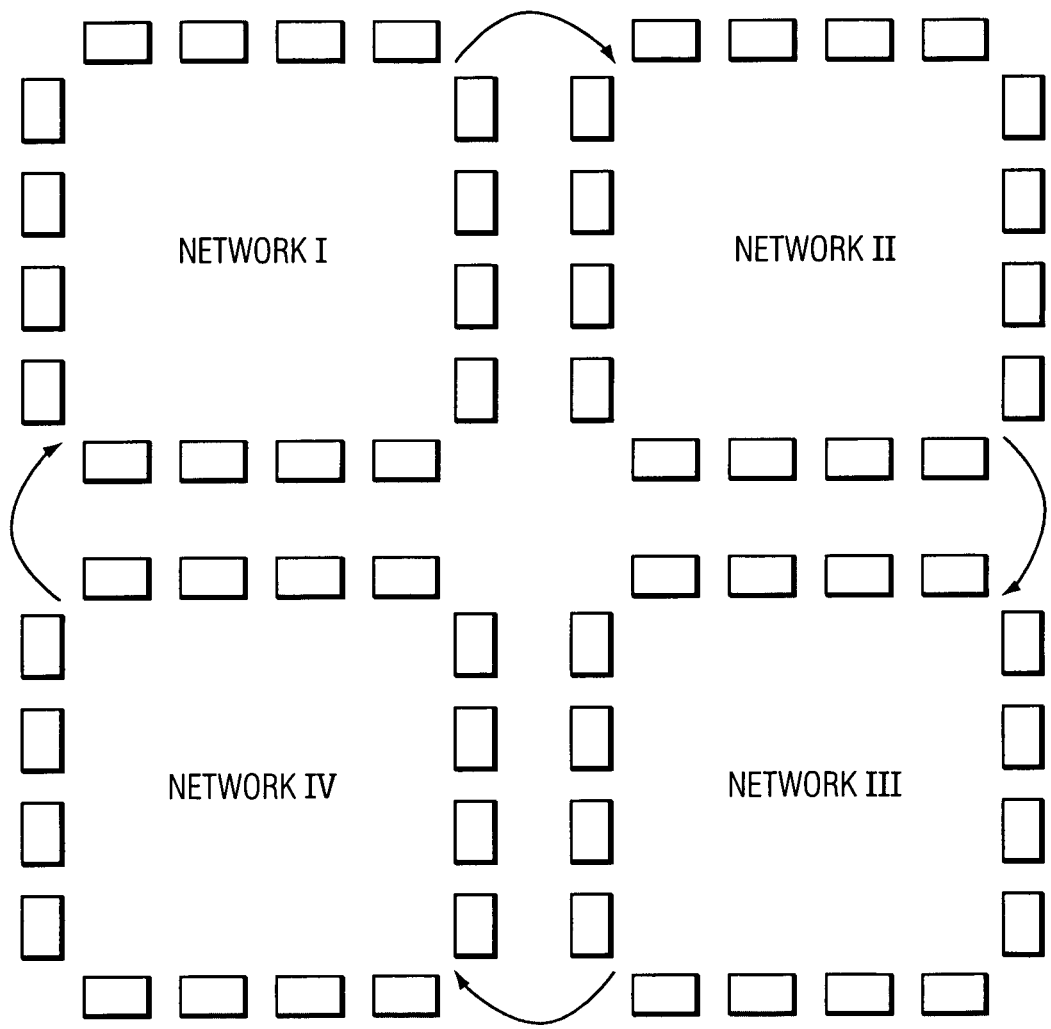
FIG. 7B shows a block diagram of the Network of networks of peripheral Medical Professionals.
Figure 8:
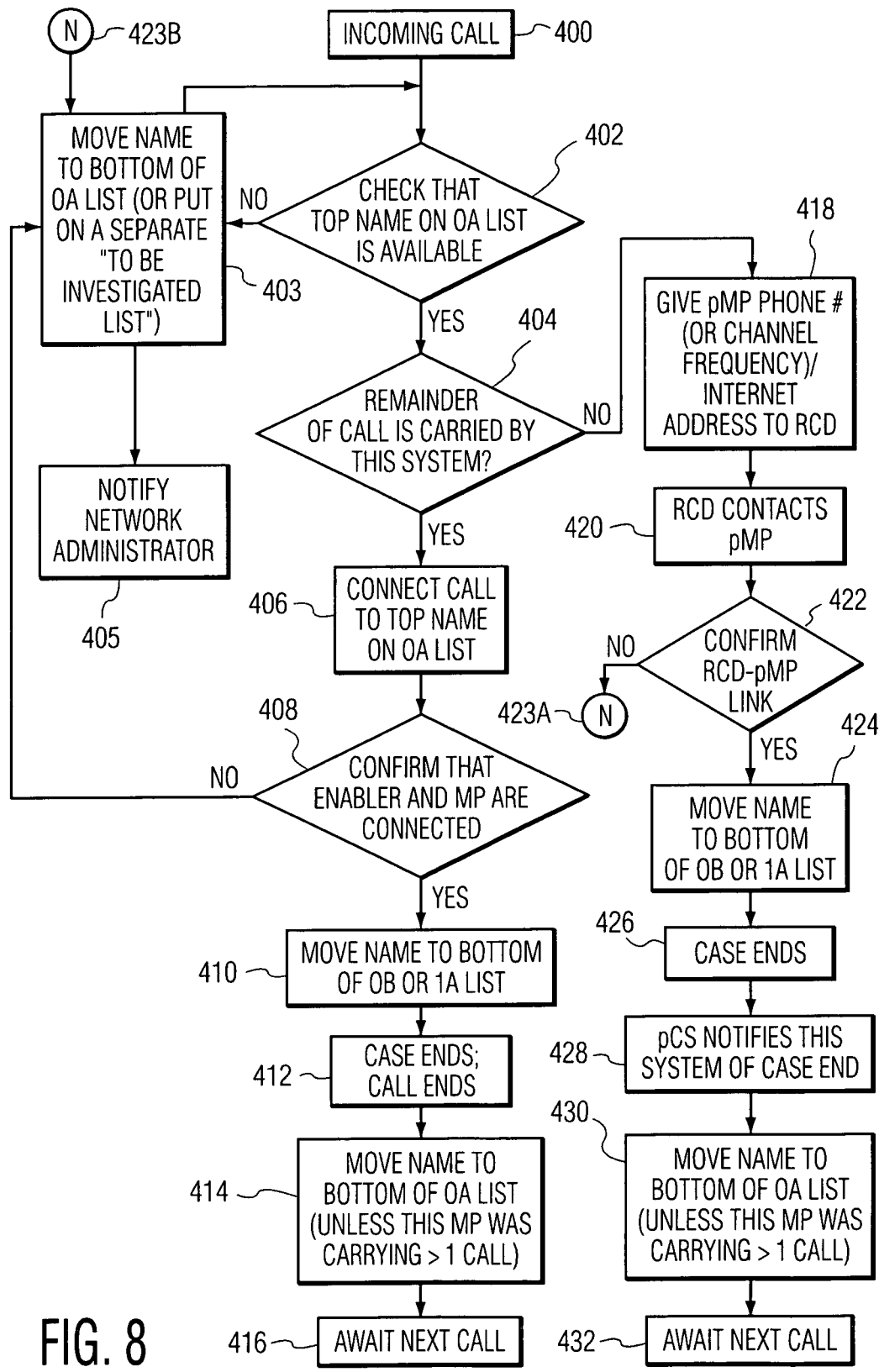
FIG. 8 shows a block diagram of the Incoming call processing by centralized MP assignment system.

FIG. 7B shows a network of networks of peripheral MPs. It consists of four networks, each similar to the one described in FIG. 7A. The four networks are linked in a ring shaped topology. Other networks of networks of pCSs are possible:
 a) with the number of networks greater than or less than four;
 b) with member networks not all having the same number of pCSs;
 c) which are not linked in a ring topology; and
 d) some or all of whose member networks may not themselves be linked in a ring topology.

FIGS. 8-10C are flow diagrams which show one way in which call management occurs in a system with centralized MP assignment, i.e. in which a TDD or a TDP performs the "matchmaking" function of assigning incoming calls to pMPs (or to a combination of central station-based MPs and pMPs). Although the TDD or TDP could be based in a mCS (e.g. 244 in FIG. 5A, 260 in FIG. 5B, 230 in FIG. 4, 204 in FIG. 3A), a TDD could also be based in a one of the pCSs; Similarly, one the pMPs could function as a TDP.

Referring to FIG. 8-18, lists of addresses/names of pMPs are maintained which indicate the MP's availability to take an incoming call. One such system is described in Table 2, below:

TABLE 2

| Name of List | MP Status |
|---|---|
| 0A | On duty, not currently handling a call |
| 0B | On duty, currently handling a call and unable to handle another simultaneous call |
| 1A | On duty, currently handling a call, and able to handle another simultaneous call |
| 1B | Off duty, but reachable, and able to take a call, if requested, within 15 minutes of the request |
| 2A | Off duty, but reachable, and able to take a call, if requested, within 60 minutes of the request |
| 2B | Off duty, but reachable, and able to take a call, if requested, within 4 hours of the request |
| 3A | Off duty, but reachable, and able to take a call, if requested, within 24 hours of the request |
| 3B | Off duty, perhaps not reachable; not able to take a call within 24 hours of the request |

Referring again to FIG. 8, after incoming call receipt 400, the TDD or TDP checks, at block 402 that the MP listed at the top of the OA list is indeed available to take a RCD call. If no, block 403, that name is moved to the bottom of the OA list, the NA is notified 405, and the name which was previously second from the top of the OA list (and which is now at the top of the list) is checked 402 for availability. The loop 402 to 403 to 402 . . . continues until a MP on the OA list is contacted. (As the bottom of the OA list is approached, various alerts [see below] will be triggered [before the bottom of the list is reached], which lead to events which allow for replenishing the OA list, and, if necessary, calling local 9-1-1 [See below, in conjunction with FIGS. 10A-C.].)

If the next portion of the call is to pass through the mCS, block 404 leads to 406, at which the mCS connects the incoming call to a selected pCS. After this, there is attempted confirmation that the enabler [EN] at the arrest scene and the pMP are in communication, block 408. If not, the MP name is moved to the bottom of the OA list, block 403, the NA is notified, and the name which has moved to the top of the OA list is checked for availability at 402. If there is confirmation of EN-MP connection at 408, the name of the connected pMP is moved, at block 410, to the bottom of either the OB list (indicating that no further calls can be taken by this MP until his current cases finishes), or to the bottom of the 1A list (which would be the case if this MP were capable of handling more than one case at a time, and his capacity was not 'saturated' by this call).

When the case ends, 412, the MP's name is moved, block 414, to the bottom of the OA list, (unless this MP was handling more than one case, in which instance he remains on the 1A list,) and the MP awaits the next call 416.

If the system is formatted to give to the RCD corresponding to an incoming call the address/phone number/frequency of the assigned pMP, so that the RCD may then directly contact that pMP, then block 404 leads to 418. The RCD contacts the pMP at 420, and, in a preferred embodiment of the invention, sends a confirmation signal to the mCS indicating the establishment of a RCD-pCS link. If the confirmation signal is not received, block 422 leads to 404 via N423A and N423B, leading to 402, and the selection of another pMP. If the confirmation is received, block 422 leads to 424, and the address/name of the pMP selected for this case is moved, 424, to the bottom of either the 0B or 1A list (where the list-selecting decision process is analogous to that discussed in conjunction with 410). When the case ends 426, the pCS sends a notification signal, block 428, to the mCS. On receipt of the notification, 430, the pMP name is moved to the bottom of the 0A list, (unless this MP was handling more than one case, in which instance he remains on the 1A list,) and the MP awaits the next call 432.

Figure 9:
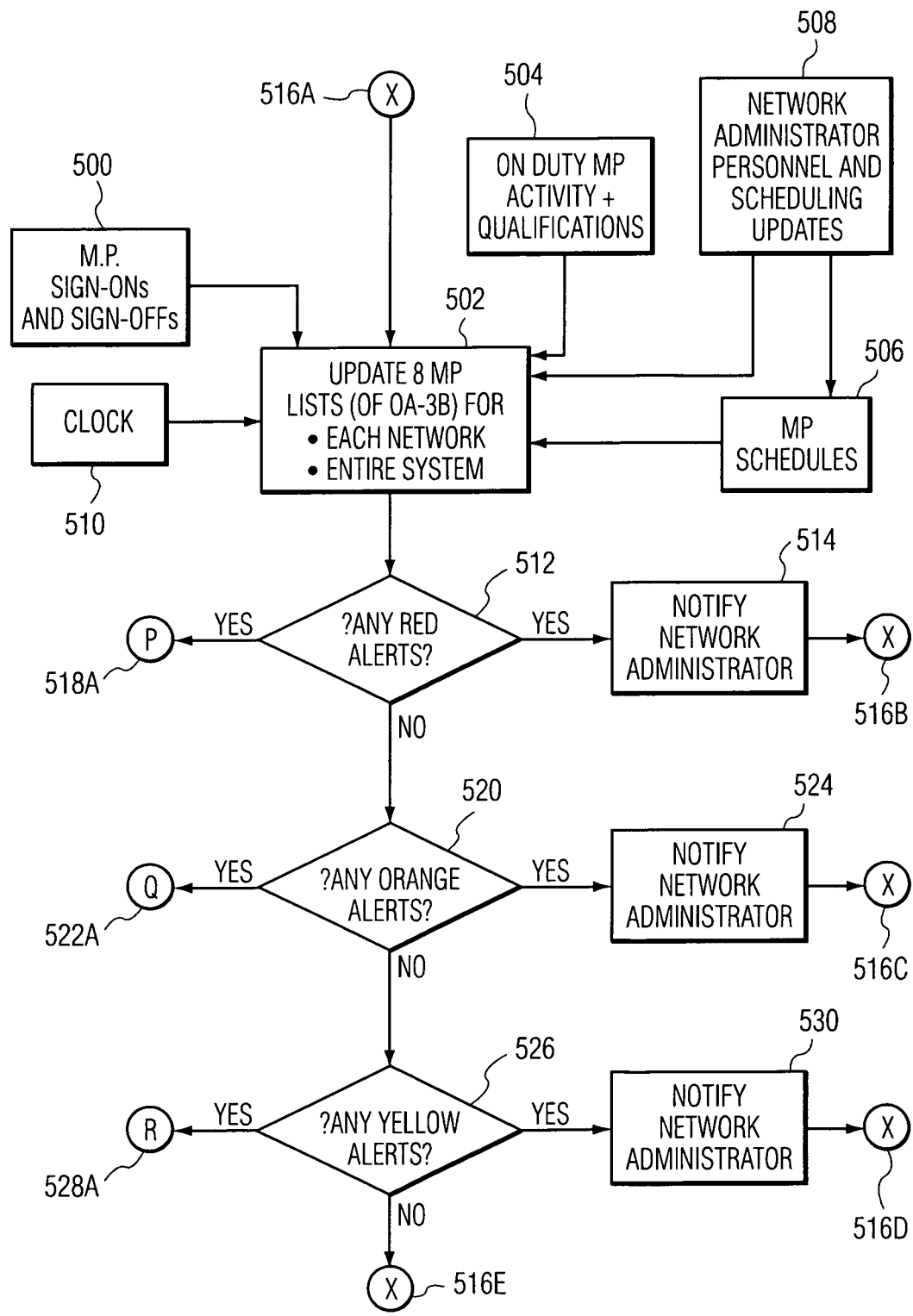
FIG. 9 shows a List updating and alert generation by centralized MP assignment system

FIG. 9 shows list management and the generating of actionable alerts, as list populations fall below critical levels. The point of the alerts is to allow the TDD or TDP to take increasingly aggressive action to re-populate the list, as the number of available MPs falls, and to thereby maintain a robust system which has an adequate supply of MPs despite fluctuations in supply (MP availability) and demand (the number and length of incoming calls).

MP signs-ons at the beginning of a shift, and sign-offs at the end, 500, update the 0A list at block 502. The content of lists 0B and 1A is determined from MP qualifications and moment-to-moment caseload variations 504, and is inputted to 502. The content of lists 1B, 2A, 2B, 3A and 3B is determined by clock time 510; and by MP schedules 506, drawn up by network administrator personnel, and updated when necessary, block 508. The NA may also, under conditions of heavy demand for MPs, allow more experienced MPs the opportunity to handle a larger case-loads (see discussion below). The arrow from 508 to 502 indicates the NA's ability to change the definition of list 1A membership; For example, during a period of heavy case load, the NA would cause the system to allow an experienced MP to remain on the 1A list until he was handling three simultaneous cases—as opposed to the usual two. (At the point of handling three cases, the MP would be taken off the 1A list and moved to the 0B list.)

When the number of names on a particular list, either within a network or throughout the system falls below a critical value, an alert is generated. In the text which follows, the number of such alerts is set at three: the mildest need for personnel is called a "yellow alert;" the most severe need is referred to as a "red alert;" and an intermediate level of need is referred to as an "orange alert." Embodiments of the invention with a larger or smaller number of types of alerts is possible. Table 3, below, shows an example of such a system of alerts and their corresponding thresholds. Numerous other formats are possible in which different need-levels trigger each of the alerts.

TABLE 3

EXAMPLE OF SYSTEM ALERTS

| CONDITION | ALERT: RED | ALERT: ORANGE | ALERT: YELLOW |
|---|---|---|---|
| Total 0A for any network | 0 | 1 | 2 |
| Total 0A for full system | <30 | 31-40 | 41-50 |
| Total 0A + 1A for any network | 1 | 2 | 3 |
| Total 0A + 1A for full system | <50 | 51-60 | 61-70 |
| Total 0A + 1A + 1B for any network | 1-2 | 3-4 | 5-6 |
| Total 0A + 1A + 1B for full system | <80 | 81-100 | 101-120 |
| Total 1B for any network | — | 1 | 2 |
| Total 1B for full system | — | <120 | 121-150 |
| Total 1B + 2A for any network | — | 1-3 | 4-5 |
| Total 1B + 2A for full system | — | <200 | 201-250 |
| Total 2A for any network | — | — | 1-2 |
| Total 2A for full system | — | — | <200 |

As indicated in Table 3, there are three different system conditions which trigger a red alert, and three conditions for any network on the system (see below). There are five system and network conditions for an orange alert, and six for a yellow alert. If red alert conditions are met, block 512, a) a series of remedial actions P518A to P518B (FIG. 10A) is performed; and b) the NA is notified, 514, leading to a repeat of list updating via X516B and X516A, with the expectation that as more MPs sign on in response to the red alert remedial actions, the condition will be remedied.

If there is no red alert condition, block 512 leads to 520 and the assessment of whether an orange alert exists. If orange alert conditions are met, a) a series of remedial actions Q522A to Q522B (FIG. 10B) is performed; and b) the NA is notified, 524, leading to a repeat of list updating via X516C and X516A, with the expectation that as more MPs sign on in response to the red alert remedial actions, the condition will be remedied.

If there is no orange alert condition, block 520 leads to 526 and the assessment of whether a yellow alert exists. If yellow alert conditions are met, a) a series of remedial actions R528A to R528B (FIG. 10C) is performed; and b) the NA is notified, 530, leading to a repeat of list updating via X516D and X516A, with the expectation that as more MPs sign on in response to the red alert remedial actions, the condition will be remedied. If no yellow alert exists, the updating process repeats via X516E to X516A.

Figure 10A:
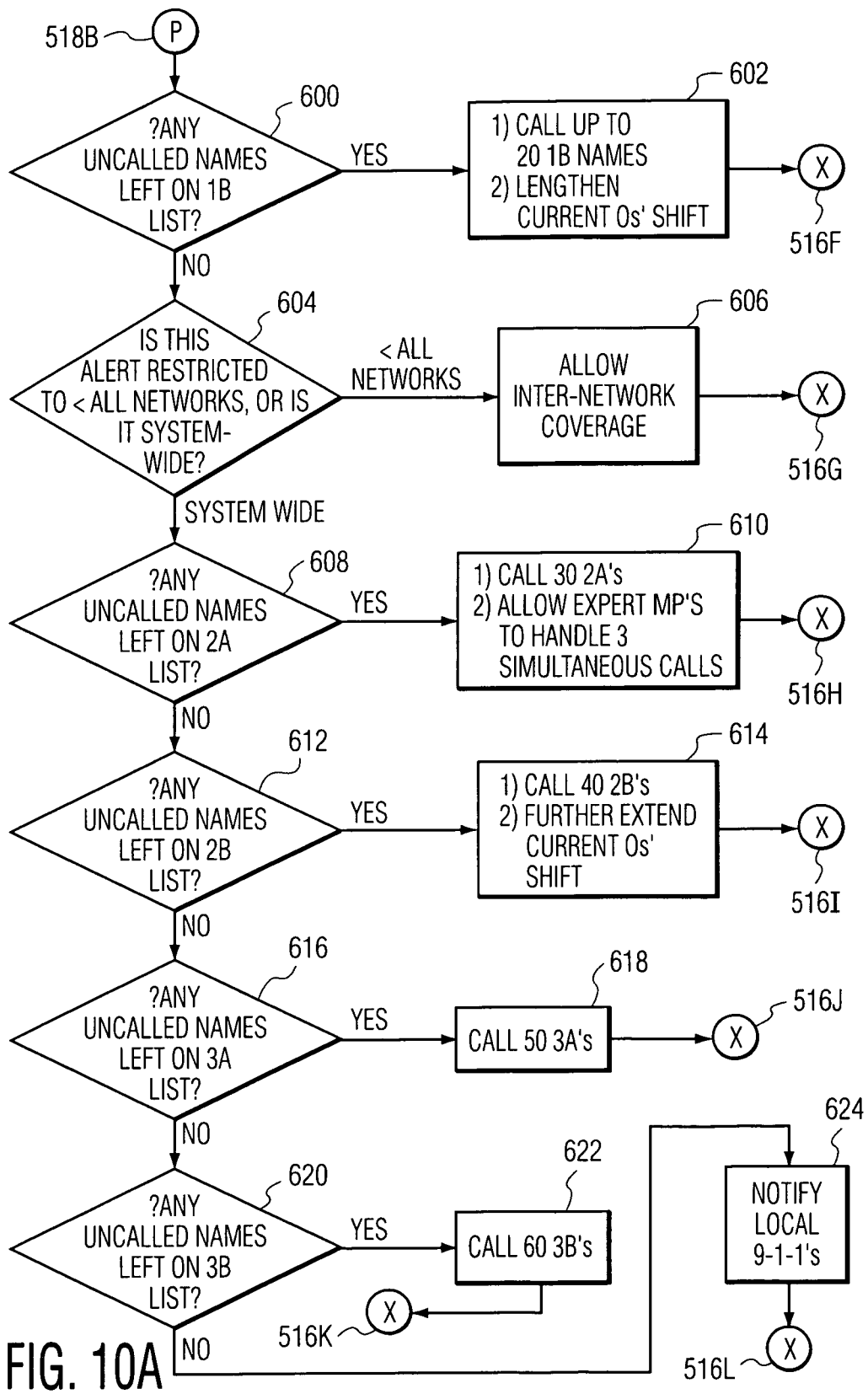
FIG. 10A shows a Red alert processing by centralized MP assignment system.
Figure 10B:
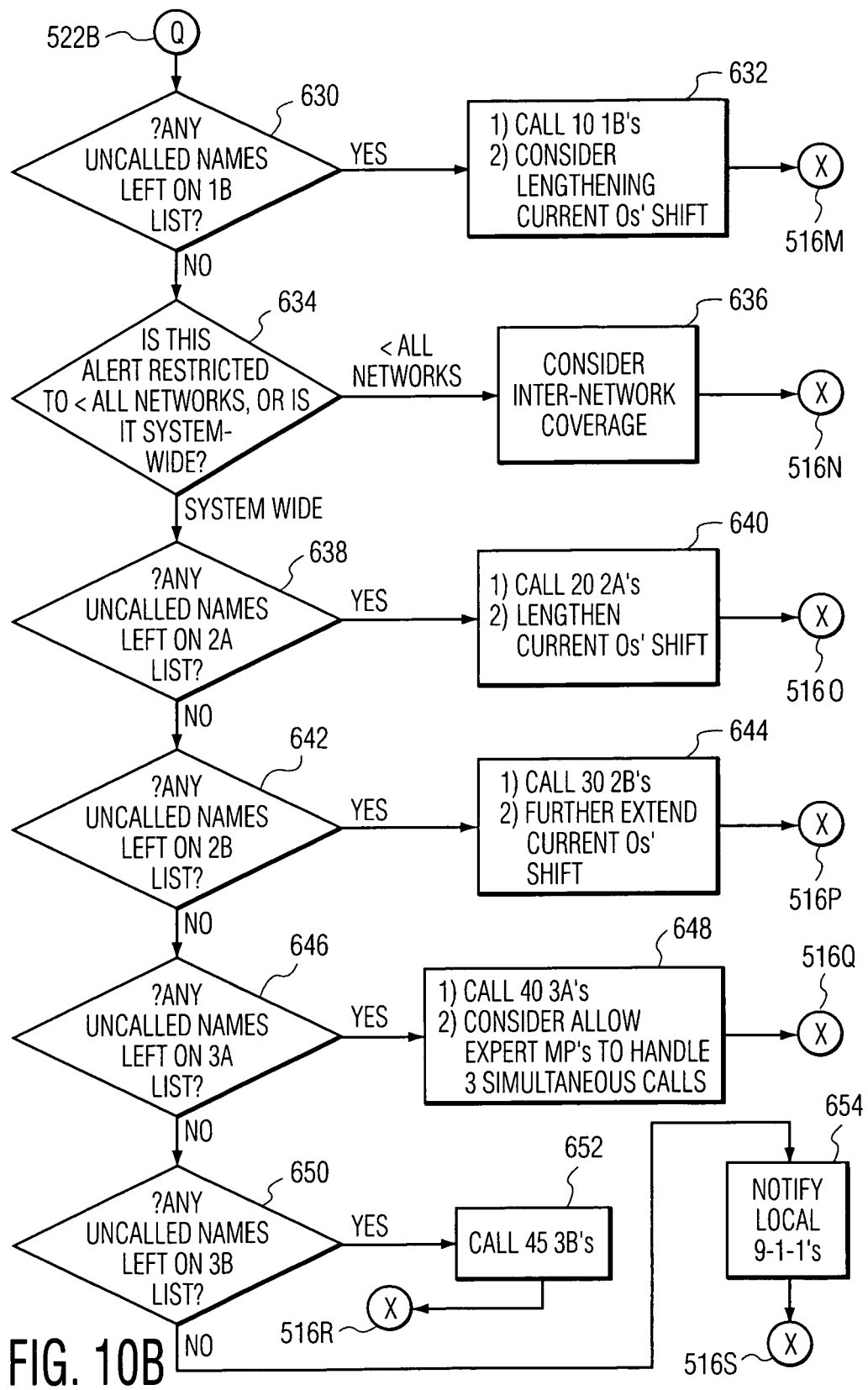
FIG. 10B shows an Orange alert processing by centralized MP assignment system.
Figure 10C:
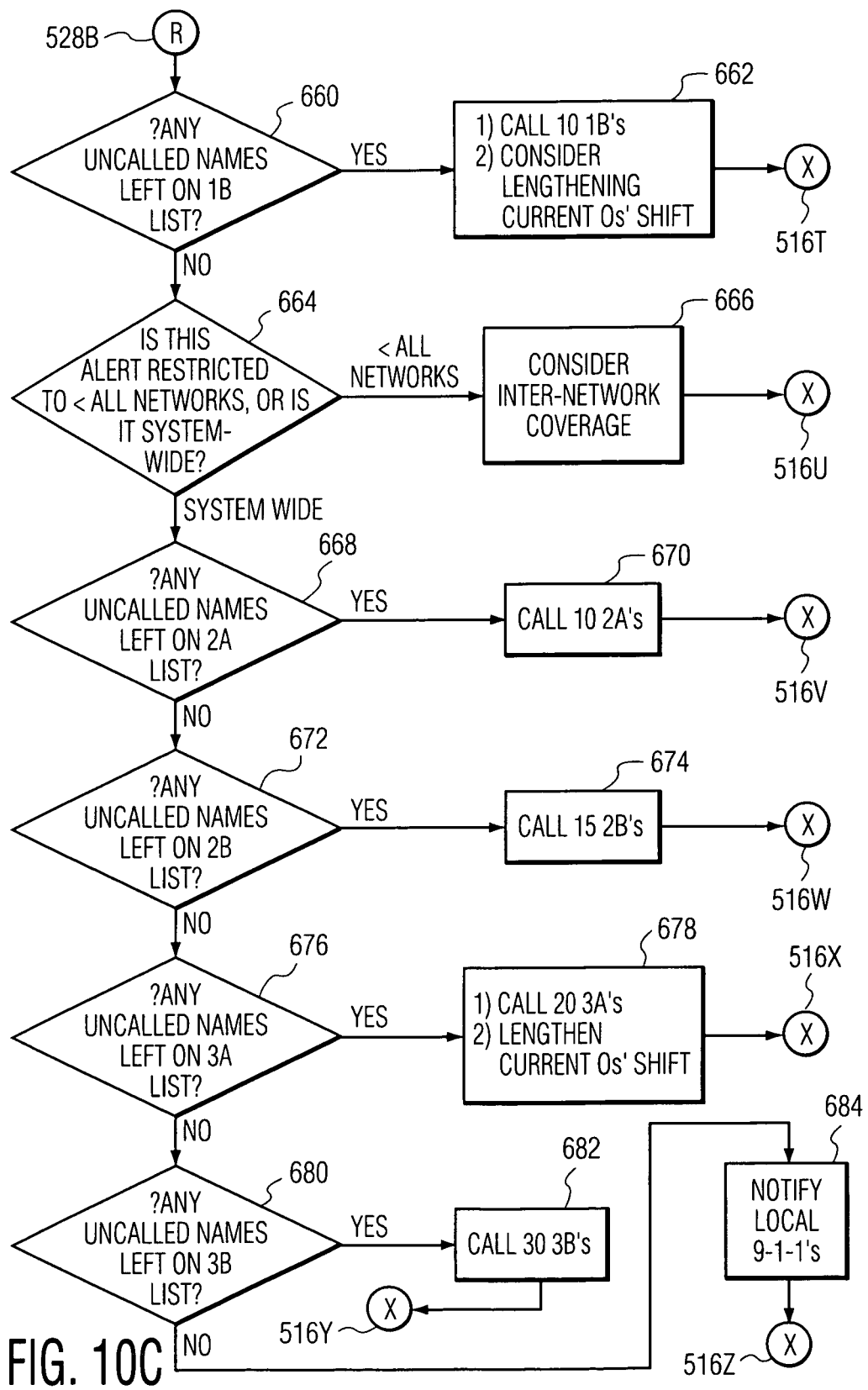
FIG. 10C shows a Yellow alert processing by centralized MP assignment system.

FIGS. 10A-C show an example of a set of algorithms which result in remedial action in the event of either a red, orange or yellow alert, occurring in a centralized MP assignment system. The goal is to always maintain the ability to respond to an emergency. One step "removed" from this is the goal of always having a suitable number of on-duty/"ready-to-take-a-call" MPs; Their number needs to be large enough so that if a sudden fluctuation in demand occurred, there would still be an adequate number of MPs available to take a call. Four ways to facilitate adequate numbers of available MPs—besides simply having a substantially larger number than is ordinarily needed—are:

a) having one or more tiers of reserves, who agree to make themselves available on short notice. In a society where medical professionals may have other functions which leave them not far from a computer screen for much of their working (and non-working) day, having a pool of reserve MPs who can make themselves available in 15 or 60 minutes allows for smoothing out of demand fluctuations by rapidly mobilizing extra reserve capacity. This makes sense economically, since the MP wages paid during a reserve period—when the MP could be working at another job or enjoying personal time, with a low expectation of actually having to handle a call—would be expected to be considerably less than if the MP had to be paid as a full-time person. Fifteen or 60 minutes are obviously arbitrary selections, and embodiments that use different "activation times" are possible, as are embodiments that have different numbers of tiers of reserves and different thresholds for calling up the reserves.

b) having the ability to request that an MP lengthen his tour-of-duty, at the request of a network administrator (or a system prompt, see below). This creates extra capacity at the end of MP shifts. The more that shifts are staggered (i.e. vary from MP to MP), the greater the capacity augmentation by shift extension. For example, if all MPs on the "day shift" worked from 9:00 a.m. to 5:00 p.m., shift extension would only create extra capacity at around 5:00 p.m.—and around 1:00 a.m. and around 9:00 a.m.—if all shifts are 8 hours in duration. On the other hand, if some MPs start work at 10:00 a.m., some at 11:00 a.m. and some at noon, the extra capacity afforded by shift extension is also more widely distributed over the course of the day.

c) having some MPs who can handle two or more cases simultaneously. The ability to do so will depend on i) the individual MP's level of experience and ability; and ii) the complexity and demands of the particular case(s) that he is currently handling. Thus newer MPs might be "certified" to handle only one case at a time, while more experienced ones might be allowed to deal with two, or even three cases at a time. The individual MPs capacity would be part of a scheduling program; Thus a shift manned by four MPs, each of whom can handle two cases has twice the capacity as one in which each MP can handle only a single case at a time. Finally, some cases— or parts of them—are particularly demanding. During such moments, even the MP who is certified for multiple simultaneous cases might choose to handle only that single case. Thus, in a preferred embodiment of the system, the multi-case-certified MP must be allowed to transiently not accept a second (or third) case. He thus must have the ability to remove himself from the 1A list and place himself on the 0B list. When the intensively attention-demanding period ends (even though the case may still be going on), that MP would preferably have the ability to take himself off of the 0B list and to put himself back on the 1A list;

d) having the ability to shift calls from one network to another. Given the nature of statistical fluctuations, the smaller the network, the greater the likelihood of a relatively large fluctuation in either supply or demand. A shift on which there are two working MPs serving, say 10,000 RCDs could be transiently overwhelmed if there were four simultaneous calls (if the ordinary call volume was one to two simultaneous calls), even though the four-call situation might occur only twice per year. However, the chance that such a fluctuation would occur simultaneously in two different networks (each with similar numbers of MPs and RCDs) is very small. Thus, in the aforementioned example, if the fourth call to the first network could be diverted to the second network (which would be, at the time, likely to be handling one or two calls), the problem would be solved. The solution would be far more economical than having four MPs working at all times on each network, knowing that all four might be simultaneously needed for only one hour per year.

The discussion of the red/orange/yellow alert management algorithm which follows makes reference to Table 3 (and acknowledges the arbitrariness of the numerical values selected for projected staffing needs). It also dovetails with the Detailed Discussion of the Network Administrator Screens referred to hereinbelow in conjunction with FIGS. 11 and 12.

If the criteria (an example of which is shown in Table 3) for a red alert are met, P518B in FIG. 10A leads to block 600, and a check for as-yet uncalled names on the 1B (15 minute reserve) list. If such names are listed, block 602, up to 20 are called, and requested to come on duty. In addition, on-duty MPs who are about to finish a tour-of-duty are requested to extend their shift. Block 602 leads to block X516F to X516A of FIG. 9 and thence to 502 and a re-updating of all lists. The expectation is that some 1B MPs have now signed on, at which point they are no longer listed on the 1B list, but instead, on the 0A list (until they receive a call). Calling these 1B (or any reserve MPs) may be via telephone, pager, email, multimodality device, or any other alerting device.

Referring again to the sample red alert remediation algorithm of FIG. 10A, if there are no further 1B names, 600 leads to 604. If the alert is not system-wide, 604 leads to 606 which allows for the shifting of calls from one network to another (See Level Two Network Administrator Screen, FIG. 12, and discussion below.); This leads to X516G to X516A.

If the problem is system-wide, 604 leads to 608, an assessment of whether there any uncalled names on the 2A list (one hour reserves). If yes, a) Up to 30 such MPs are called; and b) An additional option is allowing expert MPs to handle a larger case load, e.g. up to three simultaneous cases. This option would be exercised by having the NA change the criteria for moving certain MPs from the 1A list to the 0B list. These two actions lead to X516H to X516A.

If the 2A list is depleted of call-able names, 608 leads to 612, an assessment of whether there any uncalled names on the 2B list (one hour reserves). If yes, a) Up to 40 such MPs are called; and b) An additional option is to further extend the tour-of-duty of any level 0 (on duty) MPs. These two actions lead to X516I to X516A.

If the 2B list is depleted of call-able names, 612 leads to 616, an assessment of whether there any uncalled names on the 3A list (24 hour reserves). If yes up to 50 such MPs are called. This action leads to X516J to X516A.

If the 3A list is depleted of call-able names, 616 leads to 620, an assessment of whether there any uncalled names on the 3B list (vacationing MPs). If yes up to 60 such MPs are called. This action leads to X516K to X516A.

If the 3B list is depleted of call-able names, 620 leads to 624, and 9-1-1 facilities in regions of greatest network overcapacity are notified. This action leads to X516L to X516A.

Numerous variations on the algorithm are possible. 9-1-1 notification may be advisable at some earlier point in the algorithm than when the level 3B reserves are exhausted. State licensing requirements might prevent inter-network coverage if physician overseers (who might be supervising a group of MPs) in one state must oversee cases in a state in which they are not licensed to practice medicine. Increasing the number of cases that an MP may handle may be desirable at each step along the way, if reserves are not easily "called up."

If the criteria for an orange alert are met, Q522B in FIG. 10B leads to block 630, and a check for as-yet uncalled names on the 1B (15 minute reserve) list. If such names are listed, block 632, up to 10 are called, and requested to come on duty. Optionally, on-duty MPs who may be about to finish a tourof-duty may also be requested to extend their shift. Block 632 leads to block X516M to X516A of FIG. 9 and thence to 502 and a re-updating of all lists.

If there are no further 1B names, 630 leads to 634. If the alert is not system-wide, 634 leads to 636 which allows for the possibility of shifting of calls from one network to another. This leads to X516N to X516A.

If the problem is system-wide, 634 leads to 638, an assessment of whether there any uncalled names on the 2A list (one hour reserves). If yes, a) Up to 20 such MPs are called; and b) the shift length of on-duty MPs is increased. These two actions lead to X516O to X516A.

If the 2A list is depleted of call-able names, 638 leads to 642, an assessment of whether there any uncalled names on the 2B list (one hour reserves). If yes, a) Up to 30 such MPs are called; and b) There is an additional extension of the tour-of-duty of any level 0 (on duty) MPs. These two actions lead to X516P to X516A.

If the 2B list is depleted of call-able names, 642 leads to 646, an assessment of whether there any uncalled names on the 3A list (24 hour reserves). If yes up to 40 such MPs are called. Consideration is also given to allowing expert MPs to handle up to three simultaneous cases. These actions leads to X516Q to X516A.

If the 3A list is depleted of call-able names, 646 leads to 650, an assessment of whether there any uncalled names on the 3B list (vacationing MPs). If yes up to 45 such MPs are called. This action leads to X516R to X516A.

If the 3B list is depleted of call-able names, 650 leads to 654, and 9-1-1 facilities in regions of greatest network overcapacity are notified. This action leads to X516S to X516A.

If the criteria for a yellow alert are met, R528B in FIG. 10C leads to block 660, and a check for as-yet uncalled names on the 1B list. If such names are listed, block 662, up to 5 are called, and requested to come on duty. Optionally, on-duty MPs who may be about to finish a tour-of-duty may also be requested to extend their shift. Block 662 leads to block X516T to X516A of FIG. 9 and thence to 502 and a re-updating of all lists.

If there are no further 1B names, 660 leads to 664. If the alert is not system-wide, 664 leads to 666 which allows for the possibility of shifting of calls from one network to another. This leads to X516U to X516A.

If the problem is system-wide, 664 leads to 668, an assessment of whether there any uncalled names on the 2A list. If yes, up to 10 such MPs are called. This action leads to X516V to X516A.

If the 2A list is depleted of call-able names, 668 leads to 672, an assessment of whether there any uncalled names on the 2B list. If yes up to 15 such MPs are called. This action leads to X516W to X516A.

If the 2B list is depleted of call-able names, 672 leads to 676, an assessment of whether there any uncalled names on the 3A list. If yes up to 20 such MPs are called. In addition, shifts are lengthened. These actions leads to X516X to X516A.

If the 3A list is depleted of call-able names, 676 leads to 680, an assessment of whether there any uncalled names on the 3B list. If yes up to 30 such MPs are called. This action leads to X516Y to X516A.

If the 3B list is depleted of call-able names, 680 leads to 684, and 9-1-1 facilities in regions of greatest network overcapacity are notified. This action leads to X516Z to X516A. Network Administrator (NA) responsibilities may be viewed as divisible into three tiers of involvement:
  a) maximal involvement: The NA is involved in assigning an MP to each incoming emergency case. The Master Triage Screen shown in FIG. 42 of U.S. Ser. No. 10/460,458 and discussed therein illustrates this situation.
  b) intermediate involvement: The NA monitors network and system staffing on a moment to moment basis. Though he is not involved in the assignment of individual RCD calls, he deals with the aforementioned red, orange and yellow alerts. The NA performs such tasks from a Network Administrator Level Two Screen, such as that shown in FIG. 12, discussed below. The NA station may be a multi-screen arrangement similar to FIG. 37 herein, or a single screen on a desktop, a laptop or a smaller computer.
  c) minimal involvement: The NA is involved in the broader aspects of MP schedule planning and in the maintenance of RCDs and pCSs, but not in moment to moment scheduling. The NA performs such tasks from a Network Administrator Level One Screen, such as that shown in FIG. 11. (Given this terminology, FIG. 42 of U.S. Ser. No. 10/460,458 might be referred to as a "Level Three Network Administrator Screen.")

Figure 11:
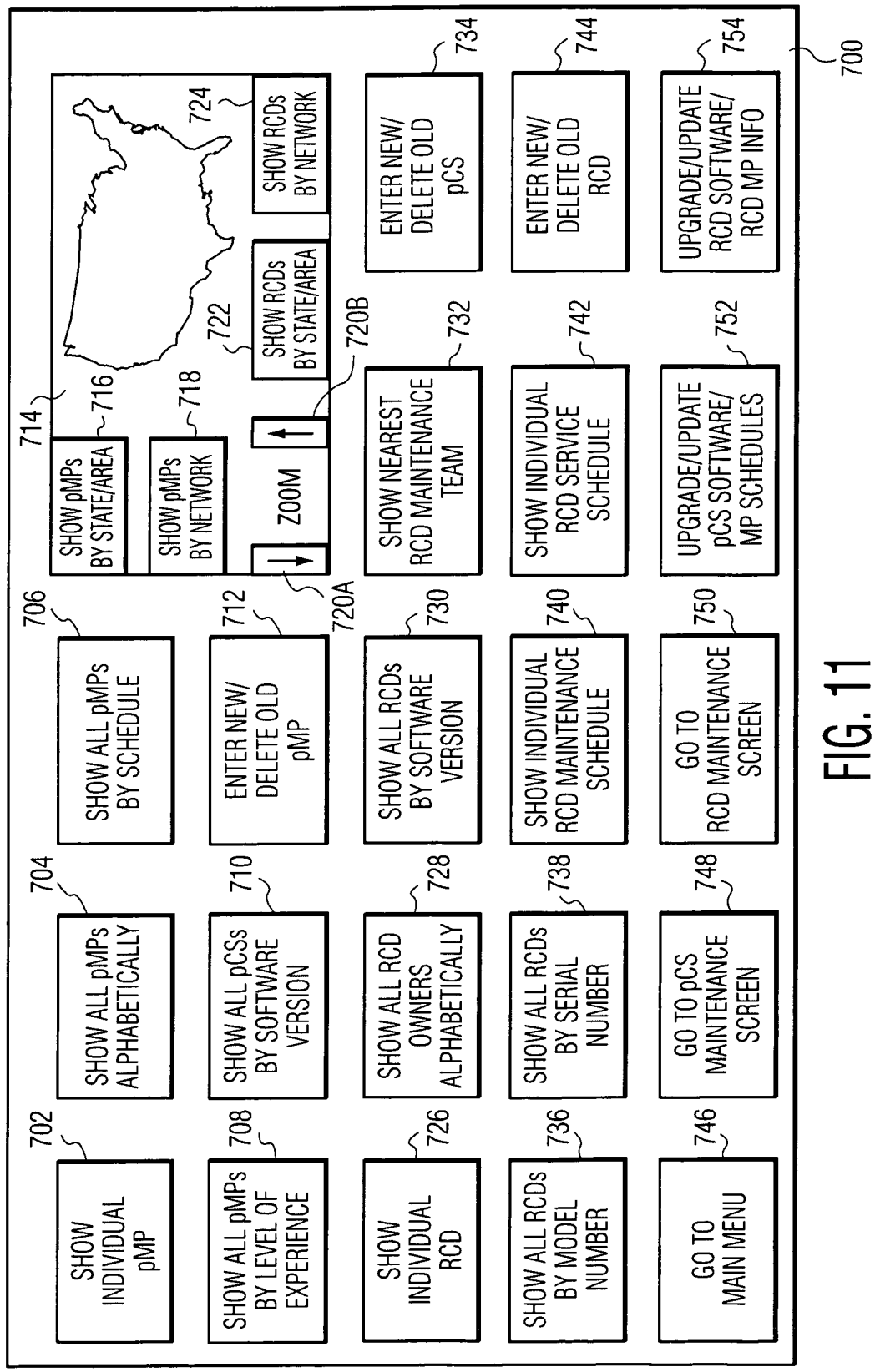
FIG. 11 shows a Level One network administrator screen.

Referring to FIG. 11, screen 700 allows the NA to:
  a) perform MP scheduling functions;
  b) maintain pCSs;
  c) maintain RCDs; and
  d) navigate to other, related screens.

Peripheral MP information is displayed by clicking on or touching (if the NA is working from a touch sensitive screen; Hereinbelow, "clicking on" will imply the possibility of designating a screen choice by "touching," if touch sensitive screens are present.):
  a) box 704, which shows all pMPs, listed alphabetically. (Hereinbelow, clicking on many of the boxes leads to another screen which, if not shown [e.g. the aforementioned alphabetical list of MPs] generally would have self explanatory and/or obvious contents.)
  b) box 706, which shows all pMPs by schedule (e.g. who is on-duty now);
  c) box 708, which shows all pMPs by level of experience (useful for deciding about the feasibility of solving a transient staffing shortage by allowing certain pMPs to transiently increase their caseload);
  d) box 716, which shows pMPs by state, region, city etc. The information referred to in boxes 716, 718, 722 and 724 is displayed on map box 714. Clicking on 720A and B results in zooming out or in, respectively, on the map. Map information may also be displayed as a text page, if requested;
  e) box 718, which shows pMPs by network; and
  f) box 702, which allows the NA to select an individual MP and access detailed information about him (e.g. credentials, experience, performance, etc.).

RCD information is displayed by clicking on:
  a) box 728, which shows all RCD owners, listed alphabetically;
  b) box 722, which shows RCDs by state, region, city, etc. on the map in 714;
  c) box 724, which shows RCDs by network on the map in 714;
  d) box 730, which shows all RCDs by software version (box 710 shows all pCSs by software version);
  e) box 736, which shows RCDs by model number;
  f) box 738, which shows RCDs by serial number;
  g) box 740, which shows an individual RCD's history of routine maintenance;
  h) box 742, which shows an individual RCD's repair/non-routine maintenance history;

i) box 732, which shows the location and contact information about the maintenance team located nearest to a particular RCD; and
j) box 726, which allows the NA to select an individual RCD and access detailed information about it.

The NA can perform a variety of tasks from screen 700:
a) adding or deleting system elements:
  i) The NA can add a new RCD or retire an old one via box 744;
  ii) The NA can add a new pCS or retire an old one via box 734;
  iii) The NA can add a new pMP or delete a retiring one via box 712;
b) upgrading/updating software:
  i) The NA can enter the latest lists of MP and/or network addresses into the RCD memory via box 754. (This information is unnecessary if the NA or CS does the call assignment. It is necessary in the embodiments of the invention (see below) in which calls are assigned automatically, i.e. without a "matchmaker.")
  ii) The NA can update RCD software, also via box 754;
  iii) The NA can update pCS software, via box 752;
  iv) The NA can update pMP schedules, also via box 752.
c) The NA can do remote diagnostic checking and maintenance (in a fashion similar to that described for remote PU and SU maintenance in U.S. Ser. No. 10/460,458; see detailed description related to FIGS. 55A and B):
  i) of the pCS, via box 748; and
  ii) of the RCD, via box 750.
d) Box 746 gives the NA access to a menu of screens that may include:
  i) Level One Network Administration;
  ii) Level Two Network Administration;
  iii) Level Three Network Administration (as shown in FIG. 42 of U.S. Ser. No. 10/460,458);
  iv) Arrest Sensor Management (See FIG. 21 and associated discussion. The NA—if his duties include call assignment—might use this screen to decide if a senor-triggered alarm needed to be assigned to a MP.);
  v) Disaster Management (See FIG. 34 and associated discussion.); and
  vi) Hospital/Rehab Patient and EMT Management (see FIGS. 35-37 and associated discussion.).

Figure 12:
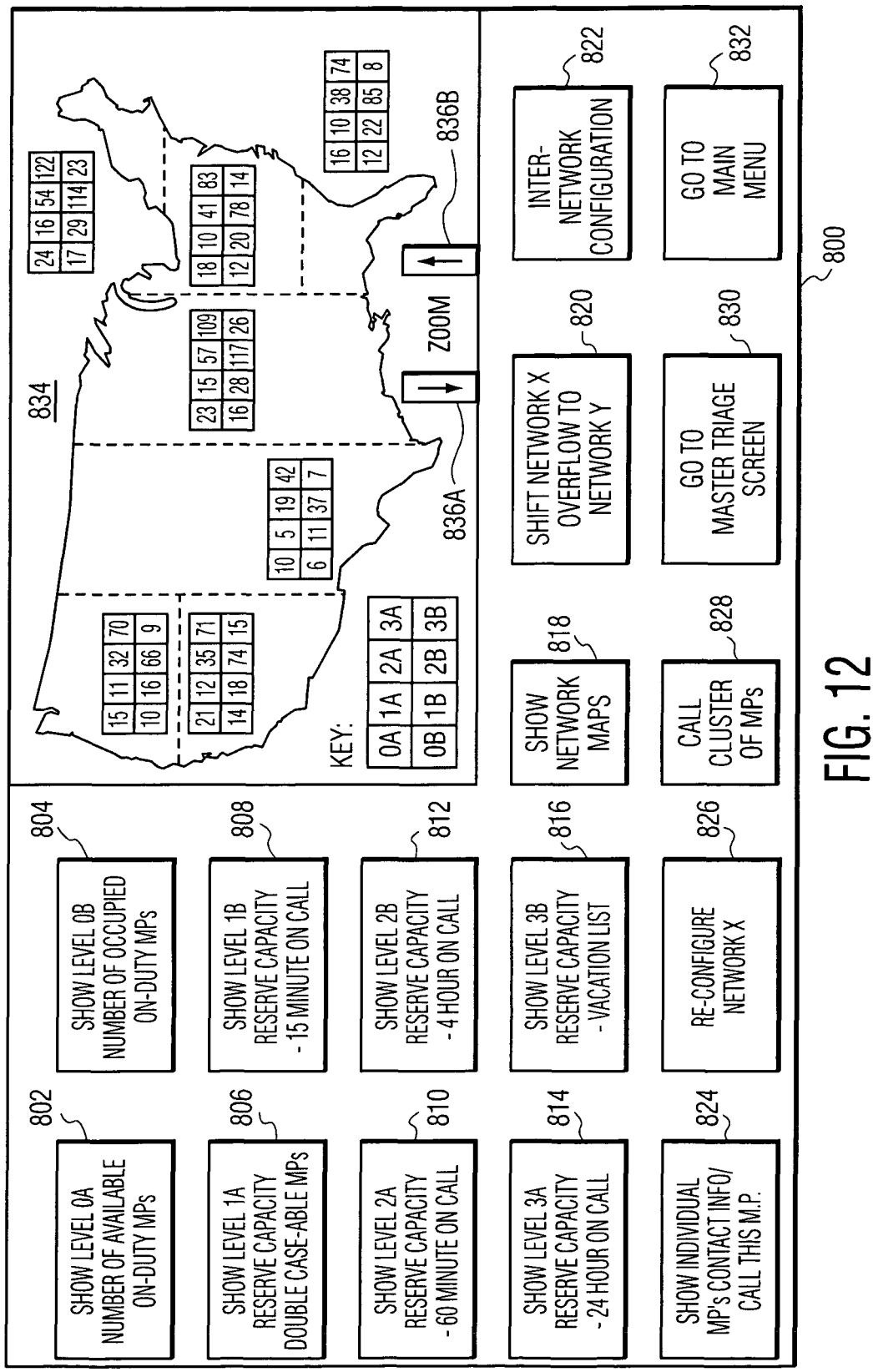
FIG. 12 shows a Level Two network administrator screen.

FIG. 12 shows a possible formulation of a Level Two Network Administrator Screen 800. Boxes 802-816 allow the NA to display each of the eight aforementioned categories of MPs. The display of this information may be a list, or it may be in map format. Screen-in-screen 834 shows a map which may contain such information. The map shows the U.S. divided into seven regions. For each region, a 2×4 matrix of numbers shows the number of MPs in each of the eight categories, 0A to 3B. The NA may choose to zoom in, 836B, and show the MP availability at the state level, the city level, or at an even smaller scale. Zooming out is accomplished with 836A. Alternatively, the NA may choose to display MP resources by network, box 818. These too can be zoomed in or out on, depending on the desired level of scope and detail.

The NA has a number of options which may be exercised via 800:
a) at the MP level:
  i) The NA may show an individual MP's contact information, and may contact that MP, box 824;
  ii) The NA may call a cluster of MPs, as is called for in each of the red, orange and yellow alert sample protocols discussed hereinabove. The MP may click on box 828, after which the keyboard (or other input device) is used to indicate which MPs are in the cluster.
b) at the network level:
  i) Intra-network manipulation: The NA may reconfigure an individual network via box 826, e.g. by adding or subtracting one or more pCSs, or by changing the geometry of the network (e.g. ring-shaped to star-shaped, or to a hybrid). Once the box is clicked on, additional information is entered via keyboard or other input device. (This command entry format, i.e. point and click, followed by keyboard [or other input device] entry, will generally be the case with NA or MP entries.);
  ii) Inter-network manipulation: The NA may:
    change the pattern of overflow from one network to another. For example, FIG. 7B shows the overflow (i.e. incoming calls unable to be accommodated) from Network I going to Network II; the NA may (if both Network I and Network II were very busy) choose to change the overflow from Network I so that it goes to Network III. This is accomplished by clicking box 820, followed by appropriate input to identify Network X and Network Y;
    The NA may choose to make more substantial architectural changes in the network structure. This is accomplished by clicking box 822, followed by appropriate input specifying the reconfiguration details.
c) Miscellaneous NA options:
  i) The NA may choose/need to be involved with the assignment of individual cases in which case box 830 takes him to the Master Triage Screen;
  ii) The NA can go to the Main Menu by clicking on box 832.

One embodiment of the invention is a network of pMPs which can operate either: a) entirely without a master central station and without a network administrator; or b) with a NA whose function is system maintenance but not call assignment/traffic direction/matchmaking. An example of the architecture of such a network is shown in FIG. 7A.

Figure 13:
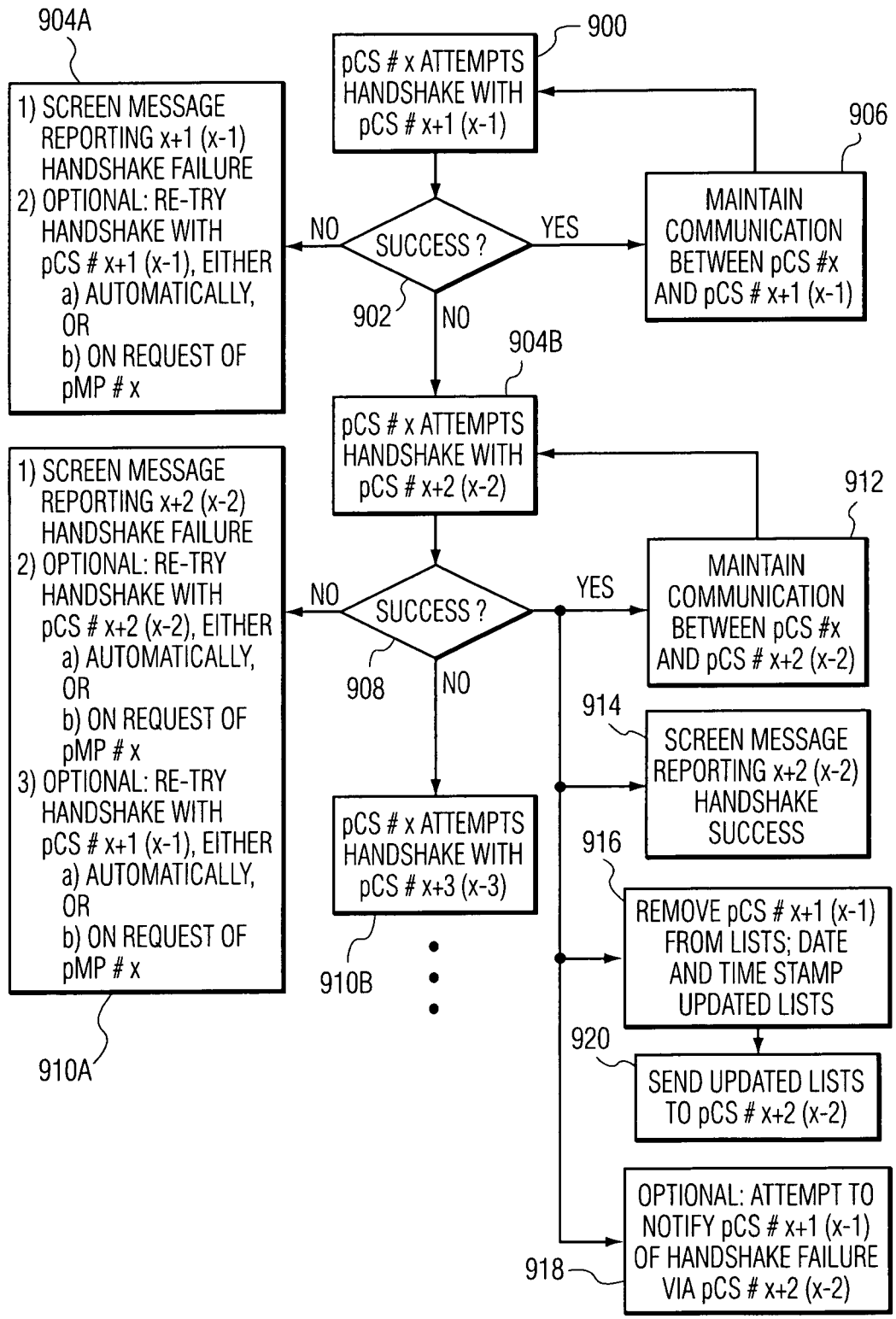
FIG. 13 shows a Possible handshake protocol among networked peripheral central stations.

The maintenance of such a network requires a handshaking protocol between adjacent pCSs, and an algorithm which contains a method of repairing the network in the event of a failed handshake. The flow diagram of FIG. 13 presents one possible handshaking protocol and repair approach. One pCS (e.g. 300B) in the ring is designated as number X (or # X). The pCS to it's right (e.g 300C) is designated as number X+1 (# X+1), while the pCS to its left is designated as number X−1 (# X−1). In similar fashion, each successive pCS to the right is numbered with the next highest integer, i.e. # X+2, # X+3 . . . , while each successive pCS to the left of # X−1 is numbered with the next lower integer, i.e. # X−2, # X−3 . . . .

For the sake of simplicity, in the discussion which follows, reference is made only to the establishment of a handshake between # X and # X+1, while FIG. 13 takes the broader approach of also including the handshake between # X and # X−1. Omitting the X←→X−1 handshake from this discussion does not imply that it does not take place.

At block 900, pCS # X attempts a handshake with # X+1. If 902 the handshake is successful, then 906 communication between X and X+1 may occur. As indicated by the arrow from 906 to 900, the handshake is repeated periodically, either at a fixed frequency, or each time there is information to be passed on from # X to # X+1.

If the handshake is unsuccessful, 902 leads to 904A and 904B. The following events occur:

a) A screen message (on either pCS # X, on pCS # X+1 [if a 'partial {e.g. one-way} handshake' did occur], or, on both pCSs) indicates the handshake failure;
b) There is an optional re-attempt of the handshake, either automatically, or at the request of pMP # X (or, at the request of pMP # X+1). (If the handshake is then successful, the protocol is re-entered at 906.)
c) pCS #X attempts a handshake with pCS # X+2 (block 904B).

If the X←→X+2 handshake is successful, block 908 leads to:
a) 912: Communication between X and X+2 may occur. As indicated by the arrow from 912 to 904B, this handshake is repeated periodically;
b) An optional screen message 914 on the screens of # X, # X+2, or both, reports the successful handshake;
c) An optional attempt 918 to notify pCS # X+1 (via a X+2←→X+1 link) of the failed handshake between pCS # X and pCS # X+1; and
d) 916: i) removal [by pCS # X] of pCS/pMP # X+1 from the list that pCS # X+1 had been on, ii) adding pCS # X+1 to either list 3B, or a separate list of pCSs needing repair attention, and iii) date and time stamping the updated lists that result from the reassignment of pCS # X+1. The updated list is then passed 920 from pCS # X to pCS # X+2.

If the X←→X+2 handshake is unsuccessful, 908 leads to 910A and 910B. The following events occur:
a) A screen message (on either pCS # X, on pCS # X+2 [if a 'partial {e.g. one-way} handshake' did occur], or, on both pCSs) indicates the handshake failure;
b) There is an optional re-attempt of the handshake, either automatically, or at the request of pMP # X (or, at the request of pMP # X+2). (If the handshake is then successful, the protocol is re-entered at 912.)
c) pCS #X attempts a handshake with pCS # X+3 (block 910B). A sequence analogous to blocks 908-920 then follows. pCS # X continues its efforts to handshake with successive network constituents, until it participates in a successful handshake.

Other optional features of this protocol include:
a) the possibility of salvaging pCS/pMP # X+1 as a functioning entity after a failed X←→X+1 handshake, if both the X←→X+2 and the X+2←ΘX+1 handshakes are intact. This would require the network to treat X+1 as a part of X+2, i.e. X+2 would be viewed as an entity with greater call-handling capacity than the standard PCS/pMP;
b) the possibility of notifying all network members (and a NA, if one exists) of a failed handshake;
c) considering the possibility that if pCS # X fails to handshake with a succession of next neighbors, that it removes itself from service, the point being that such a series of handshake failures may indicate that the problem lies in pCS # X. In that instance, the "self-removal" of pCS # X would be followed by i) signaling of such an event to both pCS # X and pCS # X−1, and ii) an attempted handshake between pCS # X−1 and pCS # X; and
d) A similar handshake protocol may run between networks, or between the designated members of different networks. In the event of a faulty inter-network handshake, the repair approach could be similar to that described hereinabove for a faulty intra-network handshake.

Figure 14:
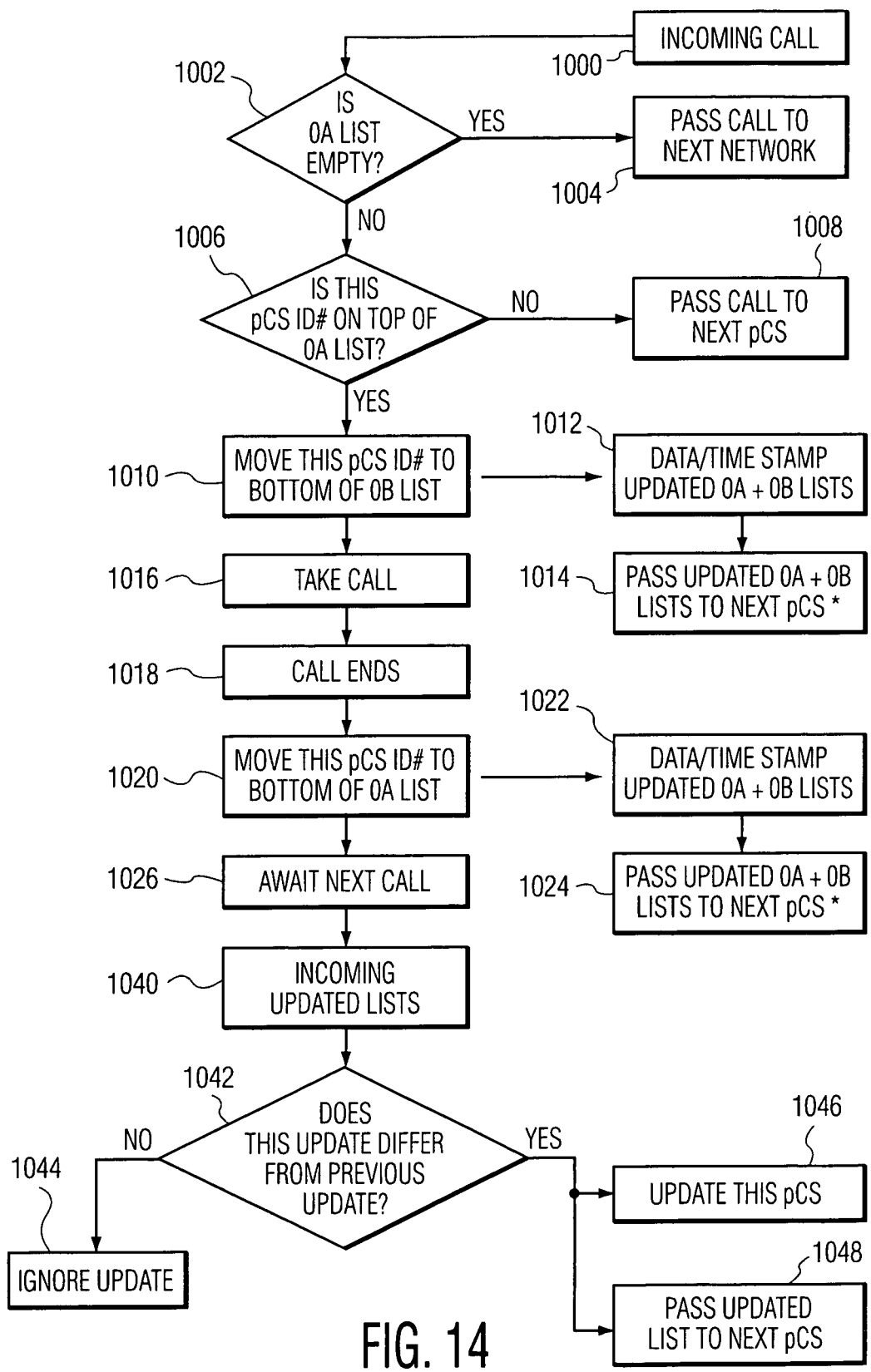
FIG. 14 shows an Incoming call and list processing by non-centralized, peripheral network-based MP assignment system.
Figure 15:
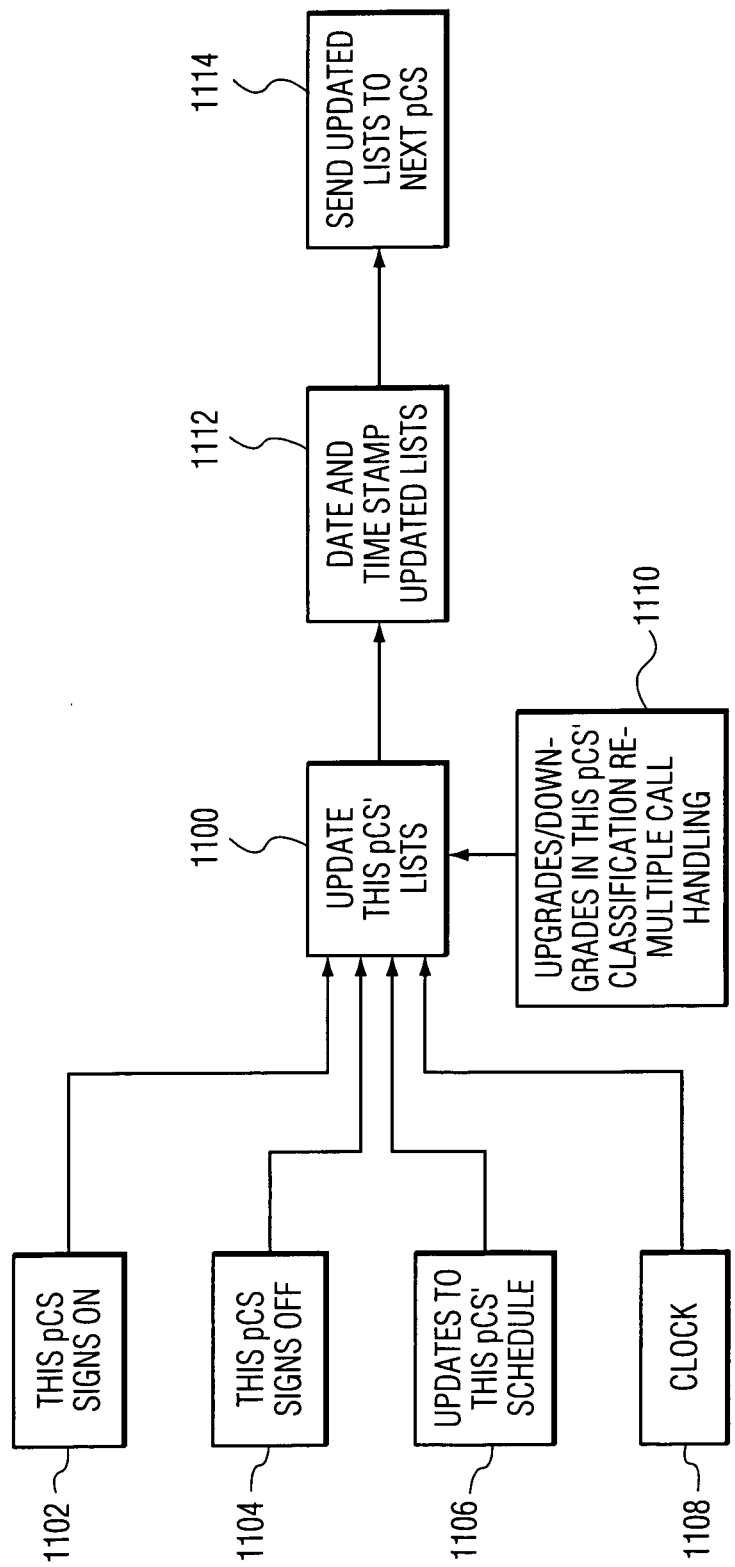
FIG. 15 shows a List updating by non-centralized peripheral network-based MP assignment system.

FIG. 14 shows incoming call and list processing for a network without a discrete call assigning entity. Incoming call 1000 is followed by query 1002, "Is the 0A list for this network empty?". If yes, 1004, the call is passed to the next network. If no, 1006 queries whether this pCS is on top of the 0A list. If this pCS is not on top of the 0A list, then this pCS is not next to receive an incoming call, and the call is passed 1008 to the next pCS in the network. (In an alternative embodiment, this pCS could take the call even if it is not on top of the list. This results in less passing on of calls, but may result in a less homogeneous distribution of calls [i.e. If there is a "key" network member who receives all incoming calls, that member would be likely to get a disproportionately large fraction of incoming calls.].)

If the pCS is on top of the 0A list, then at 1010, this pCS is removed from the 0A list and moved to the bottom of the 0B list i.e. the list of occupied, on-duty call takers. (The parallel discussion of this action, in the setting of FIG. 8 [incoming call handling with centralized call assignment], allowed for the possibility of some MPs having the capability of handling more than one call at a time. In that case, the MP would, after taking a call assignment, move to the bottom of the 1A list, if he was capable of taking another [simultaneous] incoming call. For the remainder of the discussion of incoming call handling, it will be assumed that "moving to the bottom of the 0B list could be replaced by a structure in which the MPs name moves to the bottom of either the 0B or 1A list, whichever is appropriate.) The updated 0A and 0B lists are date and time stamped at 1012, and the list is passed 1014 to the next pCS (and handled as described hereinbelow); alternatively, the updated list could simultaneously be passed to all of the pCSs on the network (and on other networks).

This pCS taking the call 1016 may follow or may be approximately simultaneous with list updating/date and time-stamping/list dissemination. After the call ends 1018 this pCS (or its identification number) becomes available to take another call and is therefore moved 1020 from the 0B list to the bottom of the 0A list. The updated 0A and 0B lists are date and time stamped at 1022, and the list is passed 1024 to the next pCS. Following 1020, this pCS awaits the next call 1026.

Lists, like calls, are passed from one network member to the next. An incoming list (or lists) 1040 is checked to see if it differs from a list already on file. If no, 1044, it represents that list having passed through the full circumference of the network, and it is ignored and not passed on any further. If it is a different list than that on file: a) this pCS is updated 1046, and b) the updated list is passed on 1048 to the next pCS in the ring.

In a non-centralized system (or in a centralized system in which the NA does not handle list management), there must be a mechanism for automatic list management. One possible mechanism is indicated by the flow diagram in FIG. 15. Four types of events result in a updating the lists (at block 1100) stored in a particular pCS:
a) 1102: this pCS signing on at the start of a shift or "tour of duty" (resulting in its removal from the list that it was on and moving to list 0A);
b) 1104: this pCS signing off at the end of a shift (or in the event of equipment malfunction);
c) 1106: updates to this pCS' schedule (For example, a pMP who comes back early from a vacation would move his name from the 3B list to another list, the choice of which would depend on the updated schedule details.);
d) 1108: At the end of a shift, as indicated by clock 1108, MPs would move from active status (level 0) to reserve status (level 3, for example [but possibly levels 1 or 2]), and the lists would be updated accordingly.

If a pMP is newly "certified" to handle two simultaneous calls (having, in the past, only been allowed to handle one call), or if another certification change (e.g. to handle up to three calls, or a downgrade in call handling status) occurs, this information is also inputted to the list updating mechanism. Such information would affect whether, after having taken an incoming call, a pMP is assigned to the 0B list or the 1A list. Changes in certification status 1110 are thus passed to the list updating algorithm.

Following list updating 1100, the newly updated lists are date and time stamped 1112, and then sent 1114 to the next pCS in the network (or, as discussed hereinabove, to all pCSs in the network).

Figure 16:
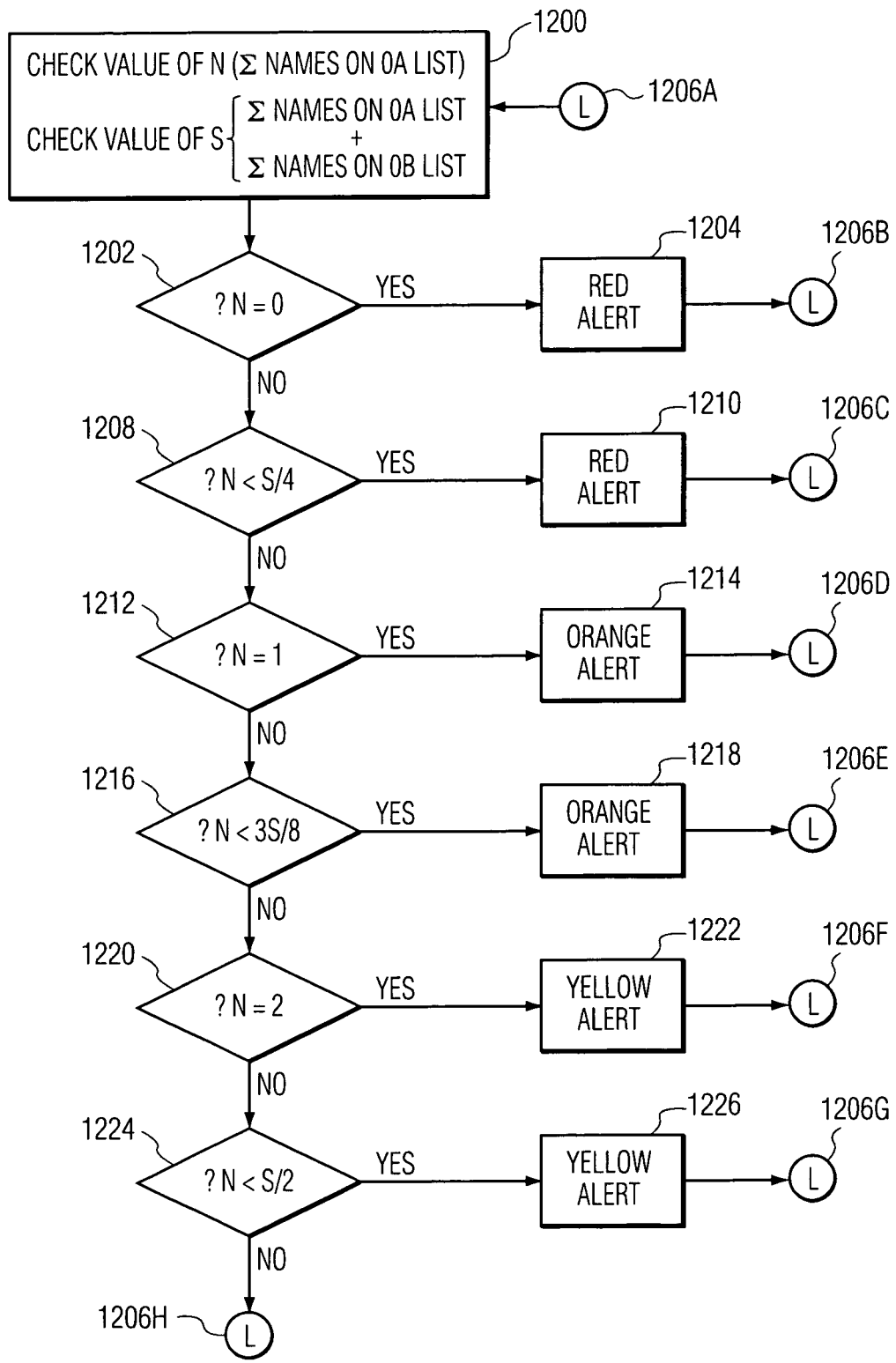
FIG. 16 shows an Alert generation by non-centralized peripheral network-based MP assignment system.

One possible algorithm for the generation of red/orange/yellow alerts in a network without a NA is shown in FIG. 16. (This algorithm could also work with a NA-based system, i.e. instead of the alert only prompting the local network to act, the alert could prompt both system and NA to act, or prompt NA only. In that case, this algorithm could be viewed as a detailed version of elements 512, 520 and 526 of FIG. 9, which asks: "?any red, orange, yellow alerts?") For computational purposes, the number of names on the 0A list is defined as "N" and the number of names on the 0A list+the number of names of the 0B list is defined as "S".

At block 1200, an updated set of values of N and S calculated. At block 1202, if N=0, a red alert is declared 1204, after which L1206B leads to L1206A and the recalculation of N and S. The aforementioned does not constitute and endless loop, since, the declaration of a red alert, as discussed hereinabove and hereinbelow (See the detailed discussion associated with FIG. 17.) results in calling up of reserves, and ultimately, in an increase in the size of the 0A list, and hence in an increase in both N and S.

If N does not equal 0, 1202 leads to 1208 which checks for N<S/4. If N is less than S/4, 1208 leads to 1210 and the declaration of a red alert. Then L1206C leads to L1206A and a reassessment of the values of N and S.

If N is not less than S/4, block 1208 leads to block 1212. If N=1, an orange alert is declared 1214, and L1206D leads to L1206A. If N does not equal 1, block 1212 leads to 1216 which asks if N<3S/8. If yes, an orange alert is declared 1218 and L1206E leads to L1206A.

If N is not less than 3S/8, block 1216 leads to block 1220. If N=2, a yellow alert is declared 1222, and L1206F leads to L1206A. If N does not equal 2, block 1220 leads to 1224 which asks if N<S/2. If yes, a yellow alert is declared 1226 and L1206G leads to L1206A. If no, L1206H leads to L1206A, and another reassessment of the values of N and S.

Algorithms with different values of trigger-points for red, orange and yellow alerts are possible. Different networks may use different values or the same values for alert trigger points. A similar algorithm may also be used to check for alerts on a network of networks (or it could check the capacity of the entire system, as per Table 3). The algorithm could also have the capability of looking at more complex entities (see Table 3) such as the number of 0A+1A MPs, or the number of 0A+1A+1B MPs, or for looking at fractions analogous to those in the aforementioned discussion.

In the case of a NA-less network, the algorithm could run on the computer of any member of the network, on all computers in the network, or on that of a designated key network member. In the case of a network of networks, an analogous statement is true; list updating would have to run from network to network. In the case of a network with a NA, the algorithm could run on the NA computer, or on another computer in the network which has access to all updated lists.

Figure 17:
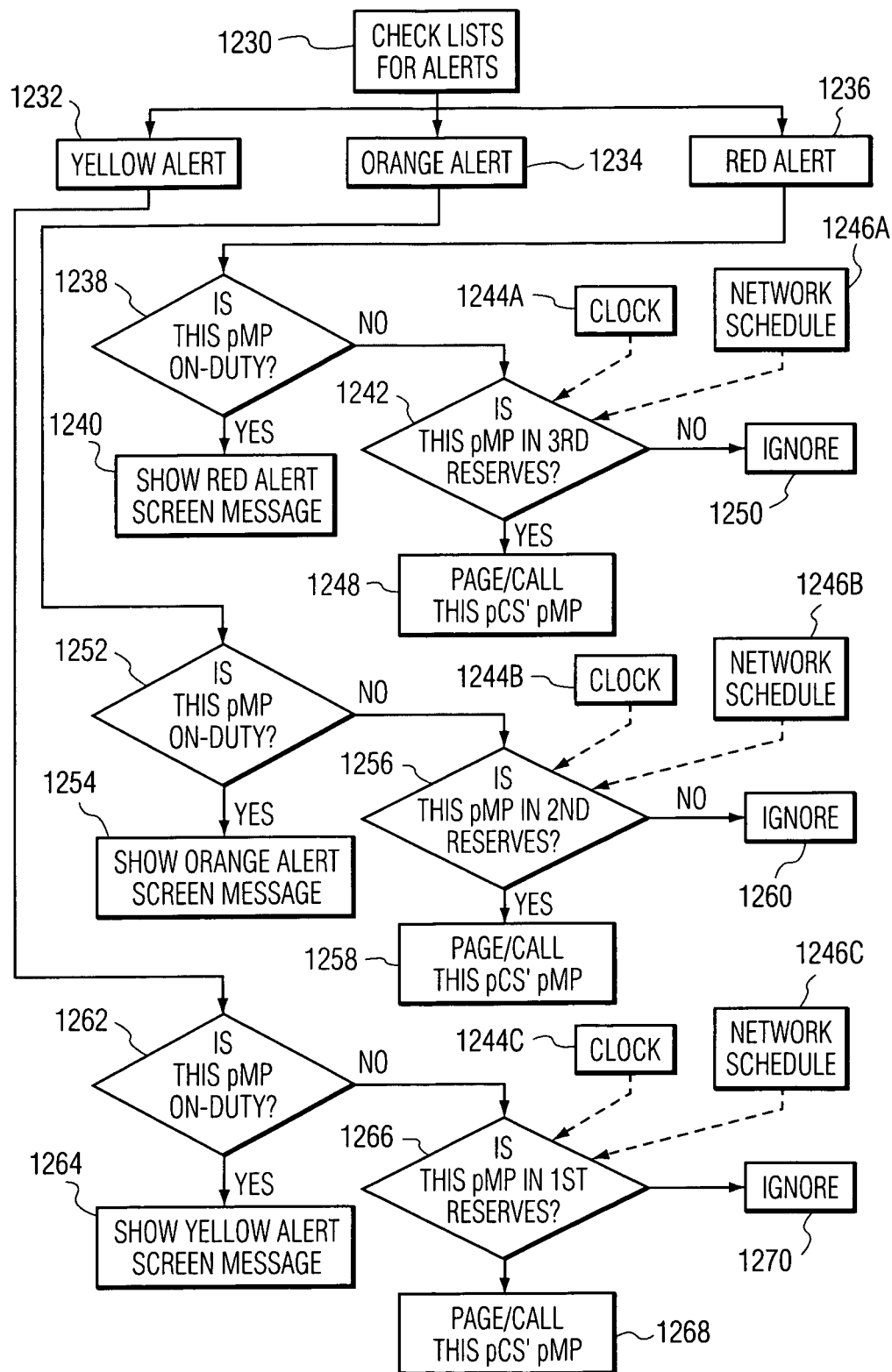
FIG. 17 shows a Red, orange, yellow alert processing by non-centralized peripheral network-based MP network

FIG. 17 shows one possible algorithm for acting upon red/orange/yellow alerts in a network (or network of networks) without a NA. The algorithm would run on each pMP's computer. (This algorithm could also work with a NA-based system, i.e. instead of the alert being generated by the local network, the alert could come from a NA, or a NA-based computer. In that case [using this algorithm with an NA-based system], this algorithm could be viewed as a variation on the parts of the algorithms in FIGS. 10A-C which indicate instructions to call up reserves.)

Referring to FIG. 17, at block 1230, if the list review process (discussed in conjunction with FIG. 16) indicates a red alert 1236, leads to query block 1238 which asks if this pMP is on duty. If yes, 1240, a screen message indicating the alert is presented to him. Such a message may suggest that optional conversations (if he is handling a case) be eliminated, and that brevity be emphasized regarding essential dialogue. If this pMP is not on duty, block 1242 asks if this pMP is in the third reserves. In order to answer, the computer will compare clock time 1244A with the network schedule 1246A (See, for example, Table 1.). If this pMP is in the third reserves, 1242 leads to 1248 and this pMP is paged or called by a variety of messaging systems as are known in the art. If the pMP is not in the third reserves, 1242 leads to 1250, and the alert is ignored. (Red alert does not lead to calling the first or second reserves, since they would have already been called in response to an orange (second reserves called) or yellow alert (first reserves); see below.

Not shown in the algorithm would be the possibility of issuing second, third and, if necessary, additional calls to the same pMP, after the first call, if that MP did not input a response to the system. Possible responses could include: a) "I am not available." b) "I am not now available, but will be available in _minutes." and c) "I am now available and am signing on." The third response would, in principle, be unnecessary, since the signing-on process would be detected (block 1102, FIG. 15). Information from the first two types of responses could be used in projecting the need for additional on-duty MPs over the minutes and hours to come, and adjusting—either automatically by a more complex algorithm, or manually by a NA, the alert status.

Referring again to FIG. 17, at block 1230, if the list review process indicates an orange alert 1234, leads to query block 1252 which asks if this pMP is on duty. If yes, 1254, a screen message indicating the alert is presented to him. If this pMP is not on duty, block 1256 asks if this pMP is in the second reserves. In order to answer, the computer will compare clock time 1244B with the network schedule 1246B. If this pMP is in the second reserves, 1256 leads to 1258 and this pMP is paged or called. If the pMP is not in the second reserves, 1256 leads to 1260, and the alert is ignored. Orange alert does not lead to calling the first reserves, since they would have already been called in response to a yellow alert (first reserves); see below.

If the list review process at 1230 indicates a yellow alert 1232, leads to query block 1262 which asks if this pMP is on duty. If yes, 1264, a screen message indicating the alert is presented to him. If this pMP is not on duty, block 1266 asks if this pMP is in the first reserves. In order to answer, the computer will compare clock time 1244C with the network schedule 1246C. If this pMP is in the first reserves, 1266 leads to 1268 and this pMP is paged or called. If the pMP is not in the first reserves, 1266 leads to 1270, and the alert is ignored.

Figure 18:
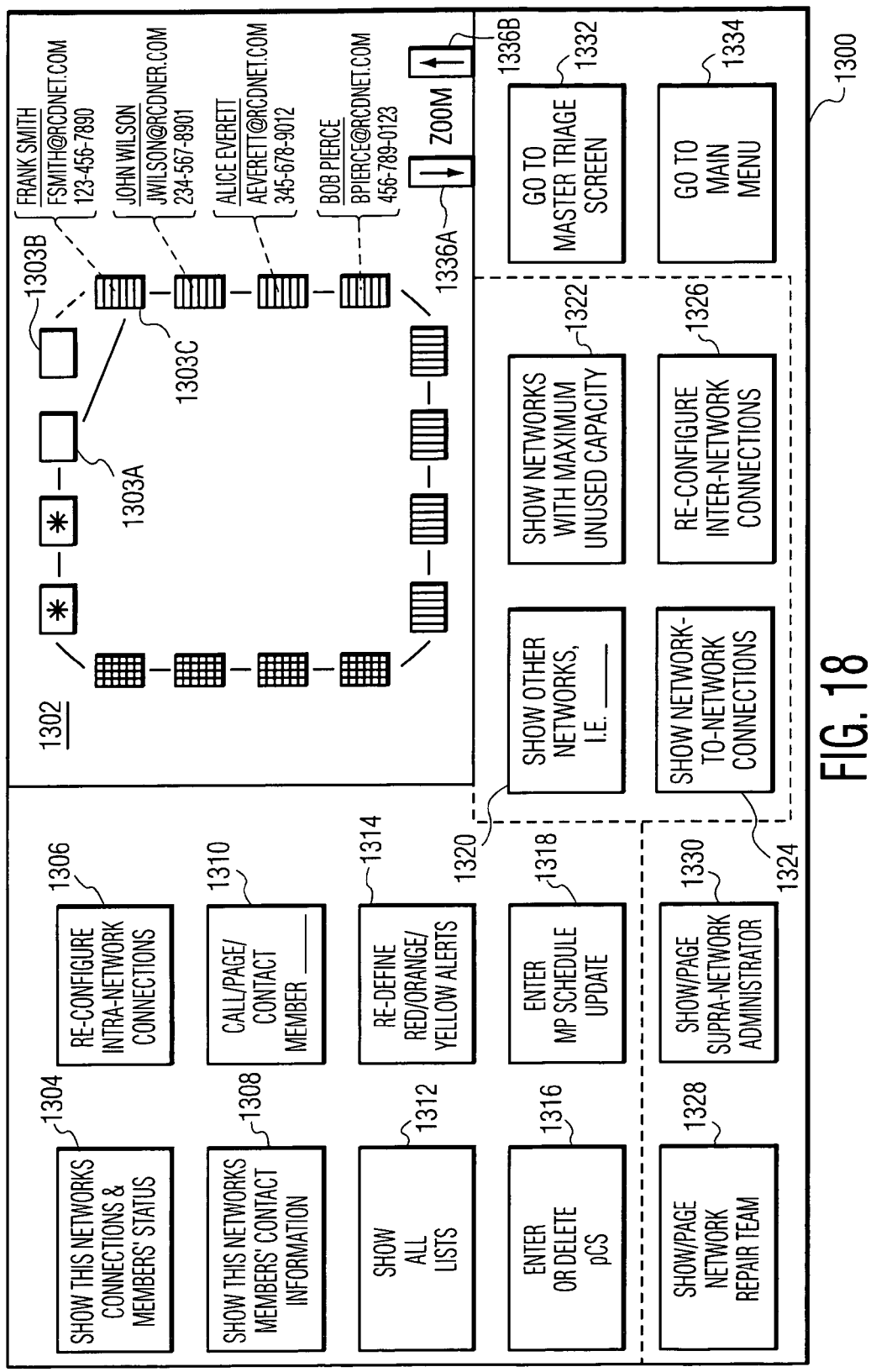
FIG. 18 shows a Peripheral MP network control screen.

Since the non-centralized network may not have a Network Administrator, the NA functions will have to either a) occur automatically, b) become unnecessary, if the system can be so designed, or c) need to, from time to time, be addressed/performed by a pMP. FIG. 18 shows a screen menu 1300 which could be called up by a pMP, which allows the performance of such tasks.

Screen-in-screen 1302 allows the pMP to view details of the network architecture and utilization (both actual and potential) with regard to his and other networks. Clicking on box 1304 shows that pMP's network connections and the status of other members of the network. In the figure, this is shown in 1302 by way of example; Clicking on other boxes (e.g. 1320, 1322, 1324) would cause the displays described in these boxes to appear in 1302.

The example shown in box 1302 in the current figure shows a 16 member network, similar to that shown in FIG. 7A. The four upper unfilled rectangles indicate pMPs who are on duty; the two rectangles with a central "*" indicate those that are, at the moment, handling a case, while the empty rectangles are not handling cases. Horizontal shading of the four rectangles on the right indicates first reserves; Vertical shading of the four rectangles on the bottom indicates second reserves; and Horizontal/vertical shading of the four rectangles on the left indicates third reserves. Contact information including but not limited to name, internet address and telephone number are indicated in the figure for the first reserves.

The presence in 1302 of a line which connects adjacent rectangles, corresponds to adjacent pCSs with an intact handshake between them. In the example shown, such a line is expected but is absent between 1303A and 1303B, indicating a failed handshake between those two pCSs. A line is present between 1303A and 1303C, indicating that a "repair" of the network has been performed, which allows bypassing the point of handshake failure (between 1303A and 1303B). The dotted line between 1303B and 1303C indicates that the handshake between those units is intact; In this case, as mentioned hereinabove, if desired, the 1303B-1303C combination could operate as one pCS with the capacity to handle two or more simultaneous arrests. Those skilled in the art will appreciate the fact that there are many other ways to display the details of network status.

To cause the repair of the pCS corresponding to 1303B in screen-in-screen 1302, the pMP using screen 1300 could click on box 1328, and be shown the address and contact information for one or more repair teams; this information could be displayed within 1302, or elsewhere on 1300. Clicking on one of the teams' name or contact information could cause that team to be paged/contacted. After the pCS corresponding to 1303B has been repaired, the pCS using 1300 could return the pCS corresponding to 1303B to active status within the network by clicking on 1306, and then inputting (e.g. via keyboard), the network re-configuration information (i.e. that 1303B is to be linked to 1303A and 1303C, and that 1303A is no longer to be linked to 1303C). Another example of the use of 1306 would be if the pMP using 1300 needed to remove a different pCS (say, the one corresponding to 1303C) from service, and have the network bypass the newly removed pCS.

A menu of network member contact information (and contact information about members of other networks) can be displayed (e.g. on 1302) by clicking on 1308. A member can be called or contacted by clicking on 1310 after clicking on the to-be-contacted person's name.

Clicking on 1312 causes 1302 to display lists of pMPs. Possible display formats include:
 a) display alphabetically/network members only;
 b) display alphabetically/members of other, or of all networks;
 c) display by reserve status (i.e. level 0A-3B)/network members only;
 d) display by reserve status/members of other, or of all networks;
 e) display all pMPs certified to handle two or more simultaneous cases/this network only; and
 f) display all pMPs certified to handle two or more simultaneous cases/members of other, or of all networks;

Box 1314 allows the user pMP to redefine the level (i.e. number of available pMPs) at which red, orange or yellow alerts are triggered. Box 1316 allows the user to enter or delete a pCS which is either newly joining the network or retiring from it. Box 1318 allows the user to update his schedule, or those of other pMPs.

Boxes 1320-1324 allow the user to address issues outside of his network. He can display another network in a format similar to that shown in 1302 in the figure (i.e. connections, members, reserve status, etc.) by clicking on 1320 and then inputting identifying information for another particular network. He could examine inter-network connections by either: a) clicking successively on two networks (displayed by clicking on 1320) and then clicking on 1324, or b) by double clicking on 1324 to display a zoomed-out map of all networks; Then, using zoom-in control 1336B, and, if necessary, zoom out control 1336A, he could optimize his view of one or more particular inter-network connections. He could re-configure inter-network connections using box 1326, in a manner analogous to the re-configuration of intra-network connections using 1306. At times of increased demand and/or a red, orange or yellow alert, the screen user may choose to show the networks with maximal unused capacity (by clicking on 1322), with the intention of diverting overflow from his network directly to a minimally utilized one.

Routine navigational controls include boxes 1332 and 1334, allowing the user to go to the master triage screen and main menu, respectively. If there is a network administrator, or a supra-network administrator (i.e. an administrator for multiple networks, or all networks), that person may be identified and contacted via 1330.

The aforementioned description of a pMP network control screen is not unique; Many other configurations are possible. Configurations with more than one screen-in-screen are possible, as are configurations without any. Screen 1300 has many similarities to screen 800 (Level Two Network Administrator, FIG. 12). Screen 1300 could be used by a Network Administrator with minimal modification, and screen 800 could be used by a peripheral MP with minimal modification.

Overview of Invention 6 (FIG. 19-21, 37)

While it is recognized that a vast number of arrests occur in the home setting, the ability to provide RCD service to the person who lives alone presents a challenge in terms of both execution and detection. Invention 6 addresses the detection issue: Determine remotely that an arrest has occurred in a person who is alone, and using that information to activate the RCD.

Detailed Description of Invention 6 (FIG. 19-21, 37)

Figure 19A:
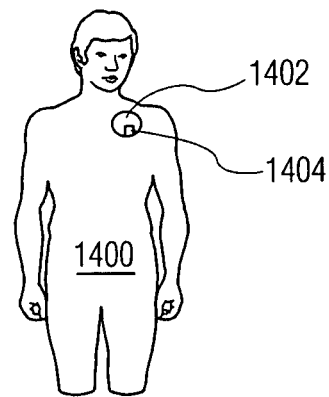
FIG. 19A shows a Leadless implantable arrest sensor.

FIGS. 19A-J show ten different methods of using a sensor in the aforementioned capacity. FIG. 19A shows an implantable device 1402 for detecting cardiac electrical and/or mechanical activity in a potential victim 1400. The device has a transmitter 1404 for transmitting said cardiac electrical and/or mechanical activity. The device may also be used to detect respiratory activity using either a piezoelectric sensor, an accelerometer, impedance measurements or acoustical detecting means.

Figure 19B:
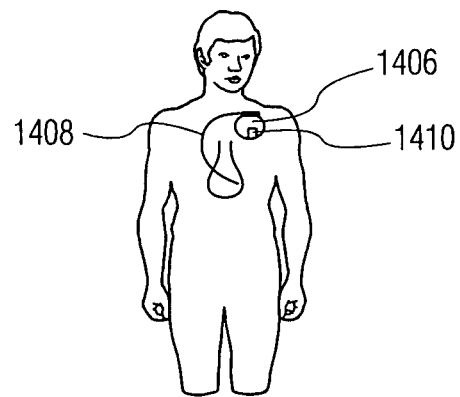
FIG. 19B shows an Implantable arrest sensor with leads.

FIG. 19B shows in implanted device 1406, such as a pacemaker or ICD, with at least one lead 1408 connected to the heart. The lead is used for sensing cardiac electrical and/or mechanical activity. The device has a transmitter 1410 for transmitting said cardiac electrical and/or mechanical activity. The device may also be used to detect respiratory activity using either a piezoelectric sensor, an accelerometer, impedance measurements or acoustical detecting means.

Figure 19C:
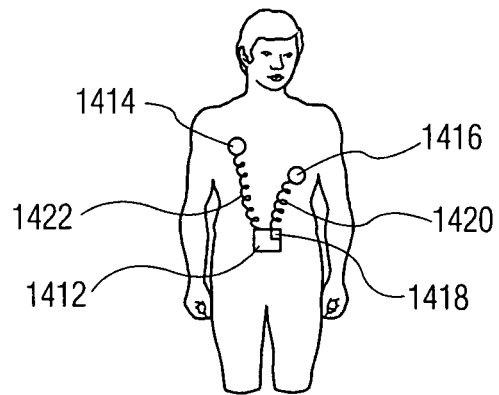
FIG. 19C shows a Wearable arrest sensor.

FIG. 19C shows an external sensing device 1412, with two or more chest wall contact electrodes 1414, 1416, with each electrode linked to the sensing device by a wire 1422, 1420, for detecting cardiac electrical activity and optionally also allowing for the measurement of transthoracic chest wall impedance. The device has a transmitter 1418, for signaling the results of its measurements to a nearby receiver; see below.

Figure 19D:
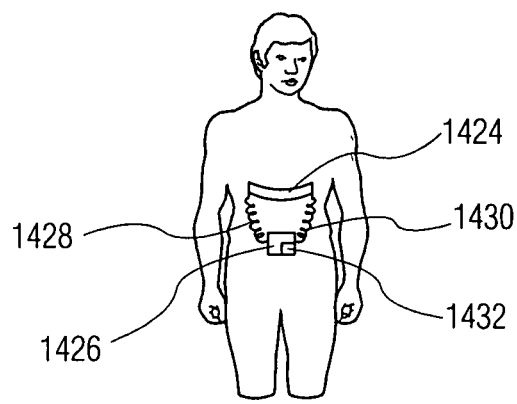
FIG. 19D shows a Belt-based device for sensing ECG and respiration.

FIG. 19D shows a wearable belt 1424, which houses two or more contact electrodes (not shown), with each electrode linked to the sensing device 1426 by a wire 1428, 1430, for detecting cardiac electrical activity and optionally also allowing for the measurement of transthoracic chest wall impedance [TCWI]. In each of the instances of TCWI hereinabove and hereinbelow, a current is applied between the two electrodes to allow for the impedance measurement. In the case of the wearable belt, respiration may also be sensed by force applied to a strain gauge within the belt (not shown), which is transduced and amplified. The device has a transmitter 1432, for signaling the results of its measurements to a nearby receiver; see below. The belt may also contain a piezoelectric crystal transducer or accelerometer-based device for detecting a sudden deceleration, at the moment of victim impact, after a collapse.

Figure 19E:
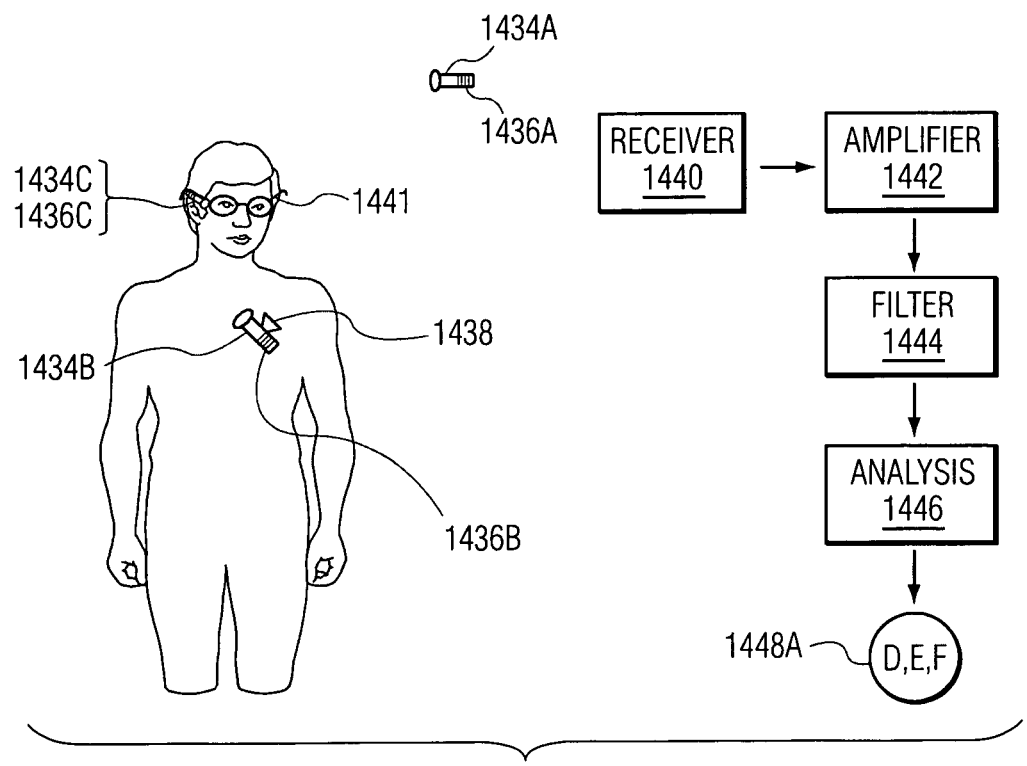
FIG. 19E shows a Microphone devices for sensing change in respiratory status and/or for using ambient conversation as inhibitory input and devices for processing this information.

FIG. 19E shows three possible microphone arrangements to detect acoustical signals corresponding to a potential victim's respirations. Freestanding microphone 1434A sends its signal to electronics package and transmitter 1436A for transmission to nearby receiver 1440. 1434A and 1436A may be mounted anywhere that a potential victim navigates. There may be one or more such devices in the victim's home or workplace. Microphone 1434B, worn on the victim's clothing, sends its signal to electronics package and transmitter 1436B for transmission to nearby receiver 1440. Microphone 1434C, worn on the potential victim's glasses 1441, sends its signal to electronics package and transmitter 1436C (1434C and 1436C shown in the figure as a single entity) for transmission to nearby receiver 1440. Receiver 1440 output is amplified by 1442, optionally filtered by 1444 and analyzed by analysis circuitry and/or software 1446. If 1446 indicates a possible, probable or definite change in respiration, it produces output 1448A which serves as a "button press" for the RCD (see FIG. 20 detailed description), which results in the establishment of contact with an MP, as described hereinbelow. The microphones may also detect victim collapse by detecting the sound(s) of the victim collapsing.

A combination of the devices shown in FIGS. 19D and 19E allow for a microphone to be placed against the chest wall to detect cardiac acoustic activity (the so-called first and/or second heart sounds). These sounds, or a signal indicating their presence, or a signal indicating their absence, or a signal indicating their presence at an inappropriately fast or slow rate, could be transmitted to a nearby receiver and processed as described hereinabove and hereinbelow.

Figure 19F:
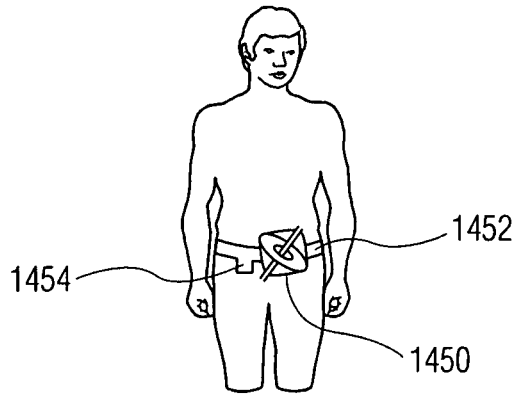
FIG. 19F shows a Gyroscope device for sensing sudden change in body attitude.

FIG. 19F shows a wearable gyroscope 1450, held securely to belt 1452 with transducer (not shown) to detect a change in the attitude of the victim (i.e. his orientation with respect to the vertical, with respect to any given direction). The transduced signal is amplified, optionally filtered, optionally analyzed and then transmitted by 1454 to a nearby receiver. Transmission may be continuous, with analysis at the receiver end, or transmission may only occur in the event that change of victim body position signals are generated. The analysis circuitry/software make look not only at the amount of change in attitude but its first, second or higher order derivatives, in order to distinguish victim falling/collapse from routine victim activity. The victim may wear more than one such gyroscopic device, each one oriented differently to allow both greater sensitivity and specificity in distinguishing a victim collapse. The power supply for the gyroscope and its electronics, not shown in the figure, would be supported by belt 1452.

Figure 19G:
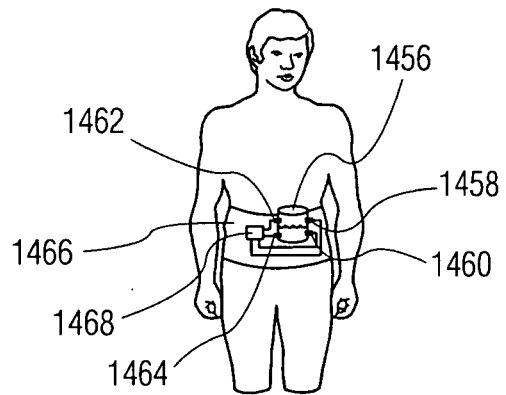
FIG. 19G shows a Fluid based device for sensing change in body attitude.

FIG. 19G shows a fluid-containing vessel 1456 for detecting a change in victim body attitude. When the victim is upright, the electrically conductive fluid allows a current to flow between electrodes 1460 and 1464 which are embedded in the wall of 1456. However, if the victim is supine: a) the flow of current between 1460 and 1464 is interrupted, and b) optionally, a flow of current between another pair of electrodes (i.e. 1458-1460, 1462-1464, or 1458-1462) may be used to confirm the change in attitude; electrodes 1458 and 1462 are placed so that they lie above the surface of the liquid when the potential victim is upright. The device, along with electronics package and transmitter 1468, are worn on belt 1466. Electrodes and the electronics package may also detect a rapid series of changes in conductivity corresponding to a splash in the fluid, which in turn corresponds to the victim's sudden collapse. For example, a splash might be indicated by momentary conduction between the 1458-1462 pair rapidly followed by conduction between the 1458-1460 pair (and possibly rapidly followed by one or more cycles of this pattern or of transient conduction between yet another electrode pair). The selection of a fluid with optimum viscosity may allow optimum distinction of victim collapse from routine victim activities; a less viscous fluid will splash less during routine victim activity. The potential victim may wear a single such sensor or multiple ones. Wearing multiple sensors may increase the sensitivity and specificity of collapse detection by: a) wearing sensors with different orientation; b) wearing sensors, the fluid in each of which fluid has different viscosities [using one or more of i) splash analysis and ii) the analysis of a time-averaged fluid motion to best distinguish a fall from a non-fall]; c) wearing sensors with different container shape (resulting in a different "splash" pattern in each such container); d) wearing sensors on different parts of the body (such that the response of one sensor to a fall may differ from that of another, even if the two sensors are identically constructed); or e) wearing sensors whose electrode array 1458-1464 differs in geometry from one sensor to the other.

Figure 19H:
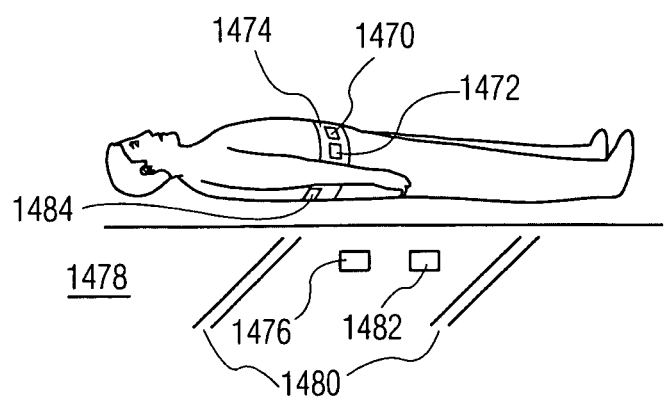
FIG. 19H shows a Ground proximity sensor for sensing victim's body.

FIG. 19H show a ground-proximity detecting device 1472, worn on belt 1474, in conjunction with power supply, electronics package and transmitter 1470. The device may detect the victim's proximity to the ground 1478 by:
  a) an increase in 60 cycle signal detection (the 60 cycle source being electric wiring 1480 running in or near the floor);
  b) an inboard ultrasound or laser device; or
  c) an ultrasensitive global positioning mechanism.

In addition, one or more sources of visible light, infrared light, acoustic or ultrasound energy arrayed within the floor 1476 may serve to trigger 1472. Alternatively, a belt-based source or any of the aforementioned energy sources 1484 may be used to trigger one or more detectors in the floor 1482, which in turn signals the RCD (either directly, or through a short-range transmitter).

FIG. 19I shows a video setup for detecting victim collapse. Video camera 1486, along with electronics package/transmitter/optional analysis package 1488 in FIG. 19I1 observe an upright potential victim, while 1486/1488 observes the same victim after a collapse in FIG. 19I2. FIG. 19I3 shows a nearby receiver 1490 which passes camera signals to amplifier 1491, and analysis package 1492. If indicative of a collapse, the signals serve as a "button push" signal for activating the RCD (See below in conjunction with the discussion of FIG. 20, and see above.) As indicated, analysis of the video information may occur before it is transmitted, using the analysis package contained within 1488, rather than 1492. The presence of more than one camera will increase sensitivity and specificity.

Software packages which allow image analysis linked to a drive mechanism for the camera housing will allow the camera to automatically follow a potential victim around its field of view. A camera which allows a large degree of zoom, either optical, digital or both, may allow for the detection of a) chest wall motion during respiration (and, its absence), b) cardiac motion (especially if the victim is supine and has an enlarged heart and thin chest wall), and c) carotid (or other) arterial pulsations.

Figure 19J:
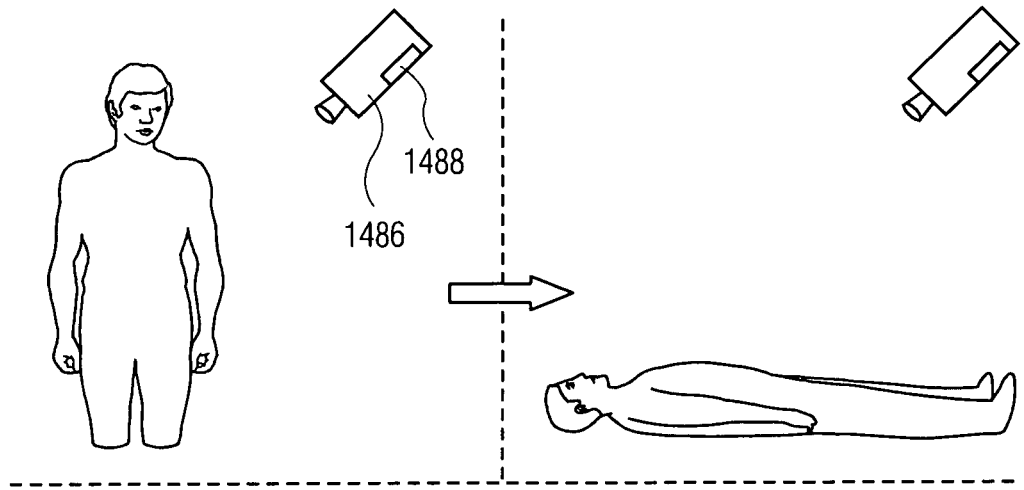
FIG. 19J shows a Polarized light emitter and sensor for detecting change in attitude of victim's body.
Figure 19J:
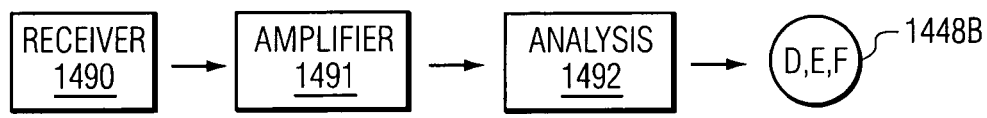
Figure 19J:
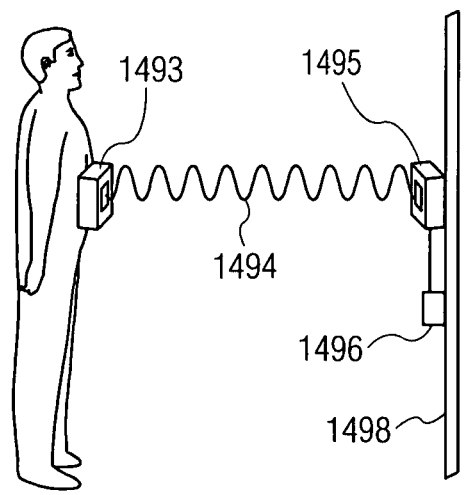

FIG. 19J shows a potential victim wearing a device 1493 which emits polarized light 1494 which is detected by detector 1495. Power supply/optional transmitter and optional analysis package 1496 are mounted on wall 1498. Alternatively there may be no transmitter with the output of 1496 being directly connected to the RCD. The analysis package may alternatively be contained within the RCD. When the potential victim is no longer upright, the output of detector 1495 declines. In a preferred embodiment of the invention, there would be multiple detectors 1495. Alternative means of arraying the polarized light source and detector include: a) having the light source on the wall and the detector (along with a transmitter, power supply and electronics package on the victim); b) having a mirror on the wall and both the light source and detector on the victim; c) having a mirror on the victim and both the light source and detector on the wall. In the case of a), the light source could consist of a strip that runs along the perimeter of each room that the victim moves through, so that no matter which way the victim faces, he is facing the source. In the case of b), the mirror could consist of a strip that runs along the perimeter of each room that the victim moves through, so that no matter which way the victim faces, he is facing a mirror.

The ideal sensor arrangement could consist of a) one sensor modality, or b) two or more of the sensor modalities described in conjunction with FIGS. 19A-J, see below.

Figure 20:
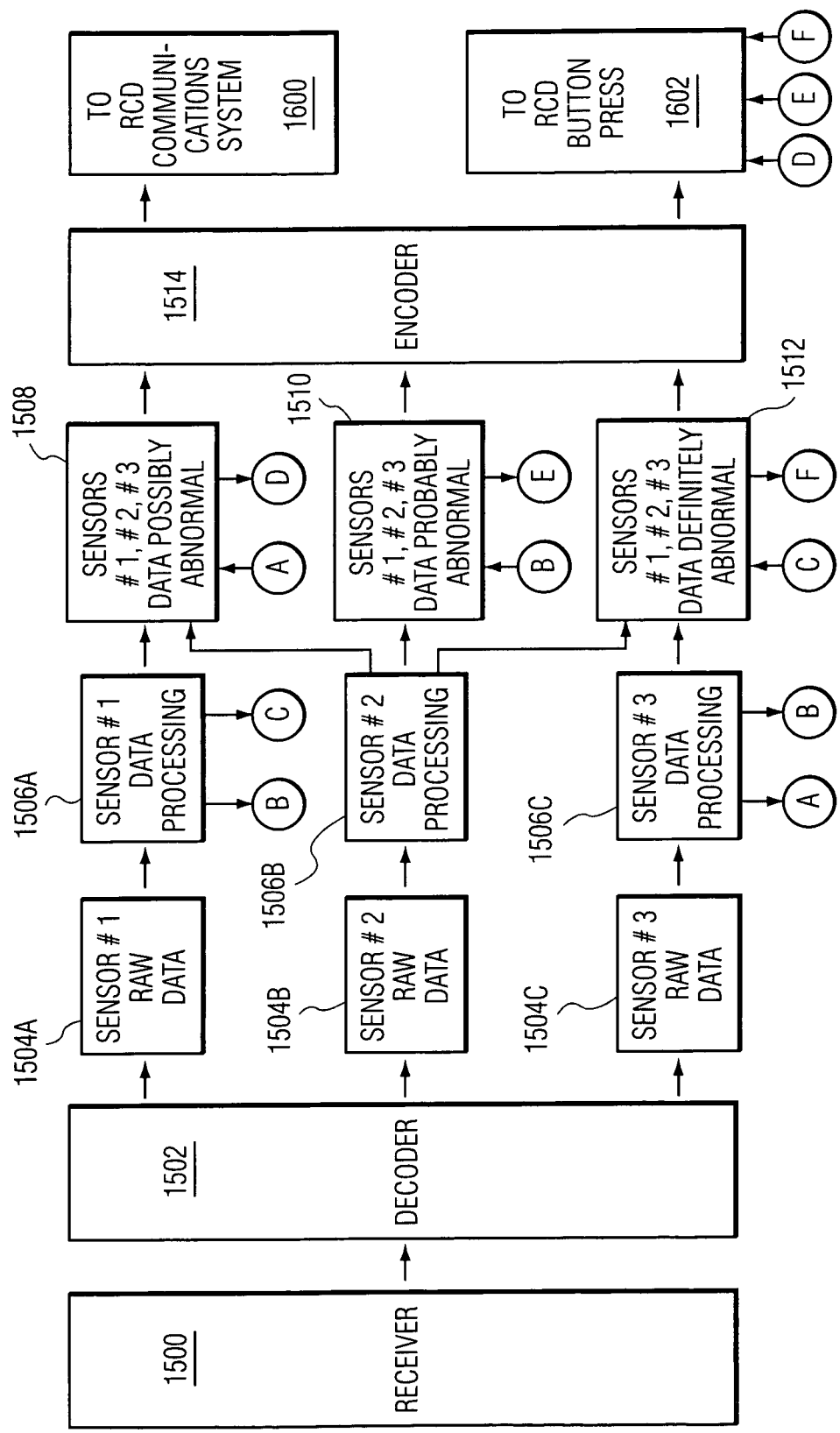
FIG. 20 shows an Arrest Sensor Signal Processing.

FIG. 20 shows sensor signal processing. In the figure, three different sensor inputs are shown; there may be more or less such inputs. If there are a plurality of inputs, they may be from identical sensors in different locations, from sensors with identical modality but slightly different design features (e.g. two fluid-based attitude change detectors (as in FIG. 19G), each with a different fluid viscosity, or from entirely different types of sensors (e.g. those in FIGS. 19E, 19G and 19I).

Receiver 1500 receives signals from the aforementioned transmitters, and sends it to decoder 1502. (Alternatively, signals from wall-mounted detectors may have a "hard-wire" connection to the system, bypassing the front-end of the aforementioned system.) The figure shows the raw data from three sources 1504A-C outputting the decoder and passed to data analysis circuitry/software 1506A-C. 1506A-C may be a) hardwired/preprogrammed; b) run on software which is update-able from a central station (or which is locally updated), or c) consist of a neural network which allows the unit to "learn" to distinguish normal from abnormal patterns of sensor output. Each of 1506A-C yields one of four possible outputs:

a) Its associated sensor output indicates a possible collapse 1508;
b) Its associated sensor output indicates a probable collapse 1510;
c) Its associated sensor output indicates a definite collapse 1512; or
d) There is no indication of a collapse.

(Circles in the figure containing the letters "A" through "F" are intended to indicate direct electrical connections between identically lettered points [e.g. 1506C outputs via "A" to 1508], and are placed to avoid confusing line-crossings.)

The outputs of each of 1508, 1510 and 1512 go to a) the RCD "button press" mechanism 1602 [Button Press is discussed extensively in U.S. Ser. No. 10/460,458. It indicates electronic activation of the RCD analogous to an enabler pressing the activation button. It carries the same meaning here.]; and b) via encoder 1514, to the RCD communications system 1600 for transmission to the central station [Thus the sensor output—either processed, unprocessed or both may be transmitted to the CS.].

Figure 21:
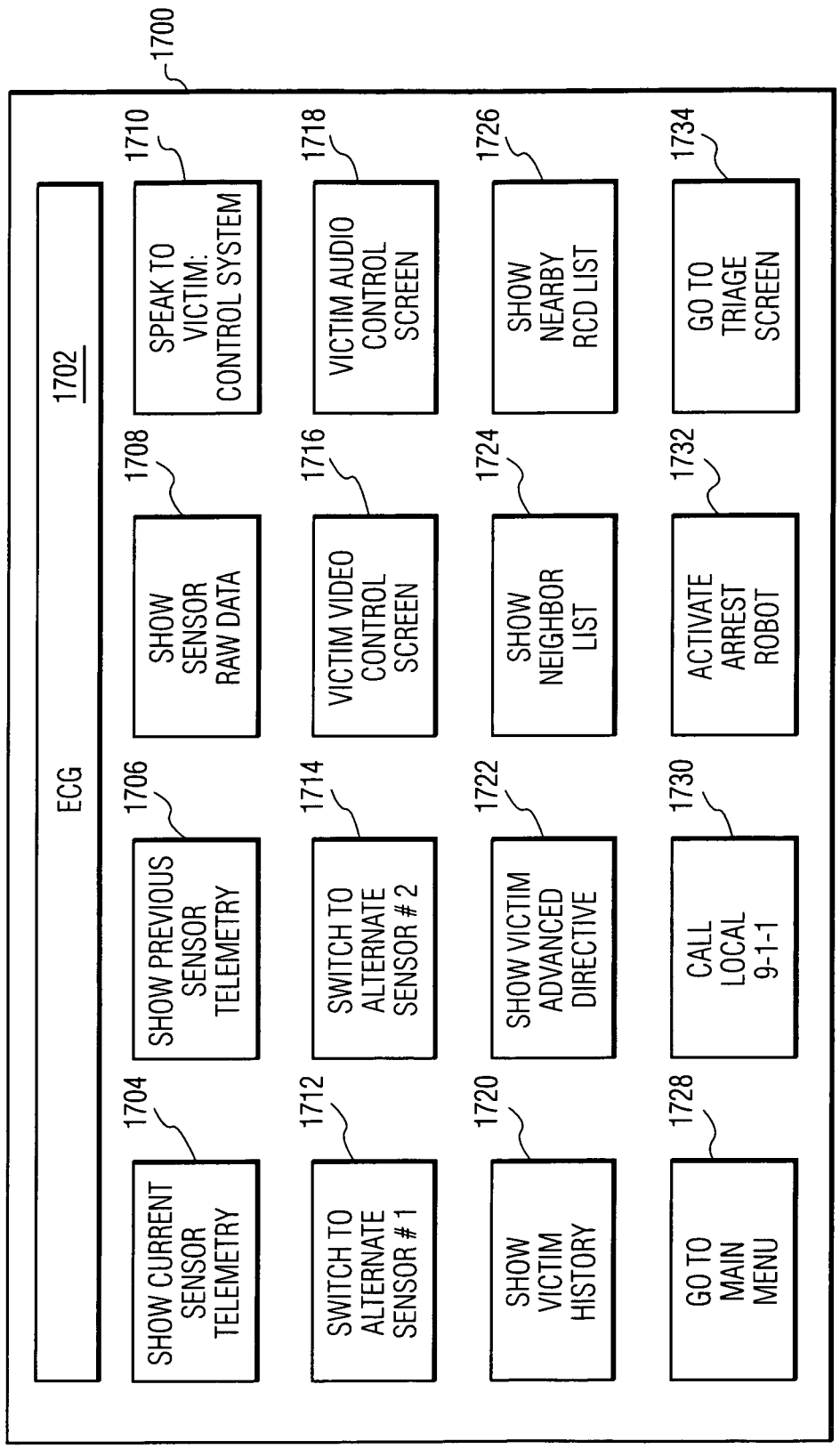
FIG. 21 shows an Arrest Sensor Monitoring and Treatment Screen.

FIG. 21 shows a central station screen 1700 for arrest sensor monitoring and treatment. By clicking on 1710, the MP may enable the transmission of a voice message to the victim. The ECG, for those sensors which allow its detection, is displayed at 1702. The MP may look at sensor information in a number of different formats:

a) He may look at unprocessed, raw sensor data (current and previous) by clicking on 1708;
b) He may look at real-time processed sensor data by clicking on 1704;
c) He may look at previous sensor data by clicking on 1706;
d) He may cause his display to show one of the victim's other sensors by clicking on 1712 or 1714; or
e) In an alternate embodiment of the invention, he may cause the victim's monitoring system to switch to an alternate sensor (e.g. a different camera) by double clicking on either 1712 or 1714.

The MP may bring up a control screen (not shown) which allows control of the victim's microphone information processing (e.g. gain, filtering, etc.), and allows the transmission of an alarm by clicking on 1718.

The MP can show:
a) victim history, medications and implanted devices, if in the system or accessible via another database, by clicking on 1720;
b) advanced directives (e.g. do not resuscitate under certain conditions) by clicking on 1722;
c) a list of neighbors and their telephone numbers by clicking on 1724; and
d) a list of nearby RCDs by clicking on 1726 ( . . . the idea being that such locations may be more likely to have a person who can do CPR).

The MP can:
a) go to either the Main Menu or Triage Screen (not shown but analogous to FIGS. 43 and 42 respectively, in U.S. Ser. No. 10/460,458) by clicking on 1728 or 1734, respectively;
b) get the contact information for, and call the 9-1-1 unit nearest the victim by clicking on 1730; or
c) activate an arrest robot (see below) by clicking on 1732.

Figure 22:
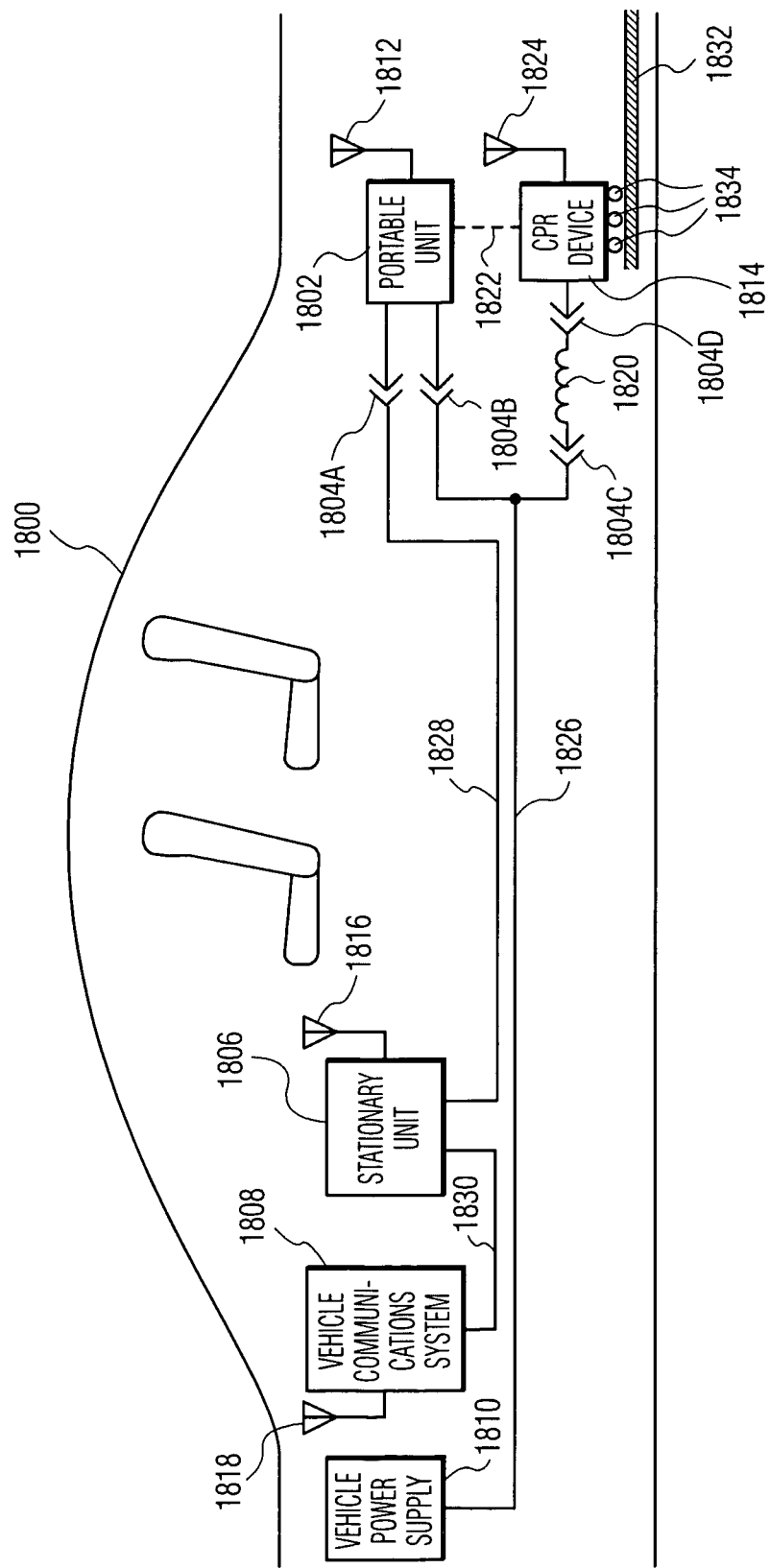
FIG. 22 shows an RCD unit in a motor vehicle.
Figure 23:
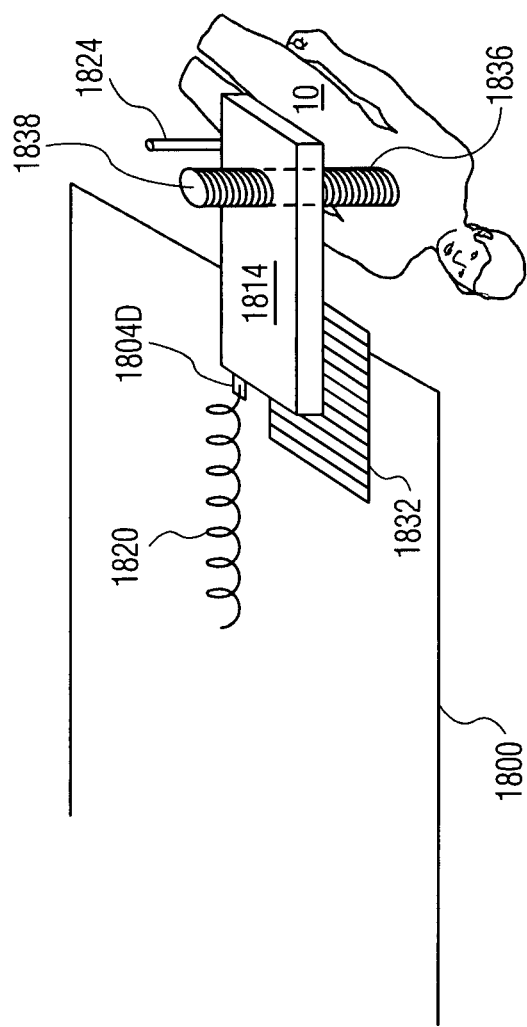
FIG. 23 shows a CPR device at perimeter of motor vehicle applying chest compression to victim.

Overview of Inventions 7-9 (FIGS. 22-24)

There are four advantages which result from placing a remotely controlled defibrillator in a motor vehicle:
A) Although it is known that most arrests occur in the home, having the defibrillator located in a motor vehicle instead of the home allows the owner the possibility of being protected when he/she is at work, (as well as at home) as long as the walk time between the actual work location and the place where the motor vehicle is parked is not excessive (e.g. under a few minutes). Assumptions implicit in the last statement are that most people in all but the large cities: a) drive to work and b) park their cars a short distance from their actual work locations. A motor vehicle-based RCD would expand the number of hours per day that the RCD could serve the owner, if:

1) the owner works, drives to work and parks the car within a short walk-time; and
2) the owner uses the car for errands, trips or any activity.

If two or more people live in the same home, but only one drives to work, then a disadvantage of the motor vehicle based approach is that during the working hours, the people who remain at home lose their protection. (Obviously, this could be remedied by having two RCDs, one in the home and one in the motor vehicle.) The removal of protection of those remaining at home during the work/errand hours would be balanced by the fact that other people in the work environment could benefit from the RCD.

B) Some motor vehicles, e.g. the G.M. OnStar and a BMW-based system, have a vehicle communications system which lets the owner communicate with a central station for an assortment of situations including keys and children locked in the vehicle. Such vehicles thus already have a means of communication linkage to a central facility, which would facilitate setting up a remotely controlled defibrillation system.

C) A motor vehicle-based RCD could take advantage of the vehicle power supply, for both: 1) charging of its own batteries; and 2) supplying energy to a device with high energy requirements such as a device for performing chest compression or CPR.

D) Allowing motor vehicle buying customers to have the option of purchasing a vehicle with a defibrillator system may improve the sales of that brand of motor vehicle.

Detailed Description of Inventions 7-9 (FIGS. 22-24)

FIG. 22 shows motor vehicle 1800 containing Portable Unit (PU) 1802. The PU is a remotely controllable defibrillator and communications unit which has the properties as the PU described in U.S. Ser. No. 10/460,458. The motor vehicle could be a car, SUV, bus, truck, motor home, farm vehicle, military carrier, train, boat, submarine or spacecraft.

During periods when the PU is not used on a victim, the PU is linked to the vehicle power supply 1810 through wire(s) 1826 and detachable link 1804B. It is linked to the stationary unit "SU" through wires 1828 and detachable link 1804A. The SU is an intermediate communications unit which has properties similar to the SU described in U.S. Ser. No. 10/460, 458. The SU as shown in FIG. 22, however, does not perform the locking/supporting function and the power supply function that the SU of U.S. Ser. No. 10/460,458 does. It would be possible for the SU of inventions 7-9 to perform the locking function by locating it immediately adjacent to the PU. It would be possible for the SU of inventions 9-11 to supply power to the PU by dividing wires 1826 into a component (1826A, not shown) which links 1810 to 1806, and a component (1826B, not shown) which links 1806 to 1804B. The SU may also change the voltage and waveform of the electrical energy supplied by 1810 to a voltage and waveform optimized for PU performance. The SU is, of course, not literally stationary when contained in a motor vehicle; nevertheless, the terminology of U.S. Ser. No. 10/460,458 has been preserved herein. Accordingly, this communications unit is referred to as the stationary unit.

During operation, the PU would usually be uncoupled from its direct links to the motor vehicle including: A) communications link 1804A (after which the PU would communicate through antenna 1812) and B) power link 1804B (after which the PU would run on its own rechargeable batteries). Element 1822 is an optional electrical link between the PU and the CPR device which may carry electrical power and/or telemetry information. If present, it may be: A) fixed at both ends, B) detachable at one end and fixed at the other, or C) detachable at both ends. If it is in place at the time that the PU is uncoupled and moved, at least one end of 1822 would be uncoupled, if CPR device 1814 is not simultaneously moved. If 1814 is simultaneously moved, at least one end of 1822 could be uncoupled to facilitate transport, or remain coupled during transport.

Once the PU is decoupled from the vehicle, it communicates with the central station in a number of possible ways including:

A) PU 1802 to antenna 1812 to antenna 1816 to vehicle SU to direct electrical link 1830 to vehicle communications system 1808 to antenna 1818 to central station;
B) PU 1802 to antenna 1812 to antenna 1816 to SU to direct electrical link 1830 to vehicle communications system 1808 to antenna 1818 to another vehicle's communications system (1808A, not shown [either directly through that vehicle communications system antenna 1818A, or through that vehicle's stationary unit 1806A (not shown)]) to that vehicle's communications system antenna 1818A, to central station (Alternatively, 1808A may have one antenna for incoming signals and a separate one for outgoing signals.);
C) PU 1802 to antenna 1812 to antenna 1818 to vehicle communications system 1808 to antenna (Alternatively, 1808 may have one antenna for incoming signals and a separate one for outgoing signals.) to CS;
D) PU 1802 to antenna 1812 to antenna 1818 to vehicle communications system 1808 to antenna 1818 (same or different 1818 as aforementioned) to another vehicle's communications system (1808B, not shown [either directly through that vehicle communications system antenna 1818B, or through that vehicle's stationary unit 1806B {not shown}]) to that vehicle's communications system antenna 1818B, to central station (Alternatively, 1808B may have one antenna for incoming signals and a separate one for outgoing signals.);
E) PU 1802 to antenna 1812 directly to central station (CS);
F) PU 1802 via "land line" (not shown) directly to CS;
G) PU 1802 to antenna 1812 to a SU (1806C, not shown, via its associated antenna 1816C, not shown) in a vehicle (1800C, not shown) other than 1800 to that vehicle's communication system (1808C, not shown,) to central station;
H) PU 1802 to antenna 1812 to a vehicle communication system (1808D, not shown via its associated antenna 1818D) in a vehicle (1800D, not shown) other than 1800 to that vehicle communication system antenna (1818D, not shown) to central station (Alternatively, 1808D may have one antenna for incoming signals and a separate one for outgoing signals.);
I) PU 1802 to a non-vehicle-based SU (i.e. the form of SU described in U.S. Ser. No. 10/460,458):
  1) to the CS, directly;
  2) through other non-vehicle-based SUs, and then to the CS
  3) through a vehicle-based SU (1806E, not shown), to that vehicle's communications system (1808E, not shown), to antenna 1818E (not shown), to the CS;

4) through a vehicle-based SU (1806F, not shown), to that vehicle's communications system (1808F, not shown), to antenna 1818F (not shown), to another vehicle's communications system (1808G, not shown [via antenna 1818G, not shown]) to the CS via antenna 1818G; or 5) to the CS through a network consisting of both: a) one or more vehicle based SUs/vehicle communications systems and b) one or more stationary SUs.

J) PU 1802 to the CS through a network consisting of both: a) one or more vehicle based SUs/vehicle communications systems and b) one or more stationary SUs.

Other embodiments of the invention include:

A) embodiments in which the vehicle stationary unit's functions are performed by the vehicle communications system, and in which, therefore, the vehicle stationary unit is not a separate entity from the vehicle communications system;

B) embodiments in which a non-vehicle-based PU (as described in U.S. Ser. No. 10/460,458) or SU (as described in U.S. Ser. No. 10/460,458) communicates with the CS through a network consisting of either: a) one or more vehicle-based SUs/vehicle communications systems or b) (i) one or more vehicle-based SUs/vehicle communications systems and (ii) one or more stationary SUs; and C) embodiments in which an implantable cardioverter defibrillator or "ICD" (as described in U.S. Ser. No. 10/460,458) or SU (as described in U.S. Ser. No. 10/460, 458) communicates with the CS through a network consisting of either: a) one or more vehicle-based SUs/vehicle communications systems or b) (i) one or more vehicle-based SUs/vehicle communications systems and (ii) one or more stationary SUs.

D) embodiments in which one or more SUs—either vehicle-based or non-vehicle based contains a router to allow it to select one or more "hops" in the communications path from defibrillator to central station.

Element 1814 is a CPR device which allows for the automatic delivery of either A) chest compressions, B) lung ventilation, or C) both chest compressions and lung ventilation. Telemetry information may pass in both directions between PU 1802 and 1814 via either electrical connection 1822 (if in place), or via antennae 1812 and 1824. Such telemetry information may include:

A) Items and parameters controlled by the MP including:
1) the rate of chest compressions;
2) the depth of chest compressions;
3) the "shape" of the mechanical impulse (i.e. the force vs. time curve of the impulse;
4) the surface area over which the chest compressing element contacts the chest;
5) the position of the chest compressing element with respect to either the victim's chest or the chest compressing device's housing;
6) parameters related to the relative positions of different supporting members of the chest compression device housing;
7) the respiratory rate;
8) the respiratory volume;
9) the frequency with which a "sigh" breath (i.e. a breath of increased volume) is applied;
10) the volume of the sigh breath;
11) the duration of inspiration and expiration;
12) the amount of positive end expiratory pressure, if any;
13) the presence of "dead space" in the ventilatory circuit;
14) the mixture of inspired gasses;
15) the temperature of the inspired gasses;
16) the humidity of the inspired gasses; and
17) the temporal relationship between chest compression and lung ventilations, specifically:
   a) the ratio of chest compression frequency to ventilation frequency; and
   b) when, during a chest compression cycle, ventilation begins and ends.

B) Information coming from the apparatus including:
1) chest compliance during compression (how 'hard' it is to compress the chest);
2) chest recoil dynamics following a compression;
3) chest/lung compliance during ventilation;
4) the content of expired gasses (e.g. end tidal carbon dioxide content);
5) chest auscultatory information, if available;
6) ultrasound information about cardiac motion, if available; and
7) information about the relative position of the relative positions of the different members of the chest compression device housing and the victim.

The CPR device receives electrical power from the vehicle power supply 1810 via wire(s) 1826, detachable connector 1804C, additional coiled wire(s) 1820 and additional detachable connector 1804D. Additional coiled wire(s) 1820 and additional detachable connector 1804D are optional. They allow the CPR device to be moved within the vehicle, or outside of the vehicle without disconnecting from the vehicle power supply; The advantage of this: Even though the CPR device would have its own rechargeable batteries, chest compression and ventilation may consume substantial enough amounts of electrical energy to make it valuable to have an energy supply beyond that which comes from the CPR device's rechargeable batteries.

Besides removal of the CPR device from the vehicle, in one embodiment of the invention, the CPR device may be rolled/slid to the back of the vehicle along one or more tracks 1832 and positioned at the perimeter of the vehicle. Optional wheels, bearings and/or gears 1834 facilitate this movement. The track(s) may run:

A) beneath 1814;
B) above 1814;
C) to the right and/or left of 1814; and/or
D) through 1814.

The movement of 1814 to the perimeter of the vehicle may be passive (i.e. the device is slid by an enabler (EN)) or active, powered by one or more motors (not shown in the figure, but using technology known in the art), which are housed either within the CPR device or outside of it. The motors, if present, may be controlled by the enabler or by the MP.

Upon reaching the perimeter or near-perimeter of the vehicle, the device may either:

A) operate from that location, for a victim on the ground lying below the device;
B) be lowered to the ground either:
  1) by having the enabler detach it and lower it;
  2) by a passive (i.e. non-motorized) pulley and/or gear arrangement powered by the enabler;
  3) by an active (i.e. motorized) pulley and/or gear arrangement powered by a motor, controlled by the enabler; or
  4) by an active (i.e. motorized) pulley and/or gear arrangement powered by a motor, controlled by the MP.

Once on the ground, the CPR device may be:
A) operated at the point that it touches down; or
B) moved to another location:
1) by having the enabler move the device
2) by an active—i.e. motorized—arrangement powered by a motor, controlled by the enabler; or
3) by an active—i.e. motorized—arrangement powered by a motor, controlled by the MP.

Optionally, a warning signal indicating the approach of the limit of coil 1820 capacity to stretch may be made available to either the EN or the MP. This signal may be generated based on:
A) a device which senses the position of the CPR device along track 1832;
B) a device which senses the number of revolutions made by wheels 1834;
C) a strain sensor within detachable links 1804C, 1804D and/or coiled wire(s) 1820;
D) video information relayed by the optional video apparatus within the PU (as discussed in U.S. Ser. No. 10/460,458) and/or
E) a global positioning device located within 1814.

Although some of the components of the motor vehicle based system are grouped on the left side of the figure, and some are grouped on the right, many other geometric arrangements are possible including:
A) arrangements in which the components in the front of the vehicle have a different spatial relationship than that shown in FIG. 22 (e.g. the vehicle power supply positioned behind, to the right of, or to the left of the SU);
B) arrangements in which the components in the rear of the vehicle have a different spatial relationship than that shown in FIG. 22 (e.g. the CPR device positioned either to the right or left of the PU);
C) arrangements with all of the components at the rear of the vehicle;
D) arrangements with all of the components at the front of the vehicle;
E) arrangements with a different distribution of components between the front and back of the vehicle (For example, the SU could be adjacent to the PU, rather than on the other side of the vehicle.); and/or
F) arrangements with one or more components of the system in the mid-portion of the vehicle, i.e. neither in the front nor the back.

FIG. 23 shows the CPR device 814, positioned on its track 1832 so that a portion of it extends beyond the perimeter of motor vehicle 1800, allowing compression of a victim 10, lying on the ground. Chest compressing cylinder 1836 is moved up and down by actuator 1838. Motion of 1836 may be caused by electromagnetic force, or by a variety of electromechanical arrangements as are known in the art. An arrangement of springs, not shown, may be responsible for some or all of either the downward or the upward motion of 1836. By anchoring one side (the left one in the figure) of 1814 to the vehicle, 1814 is stabilized so that it may remain approximately stationary during the application of force to the chest wall. Wire(s) 1820 carry electrical power to 1814 through connector 1804D. Telemetry information passes to and from 1814 via antenna 1824 or through electrical connection 1822 (not shown in FIG. 23; shown in FIG. 22).

Figure 24A:
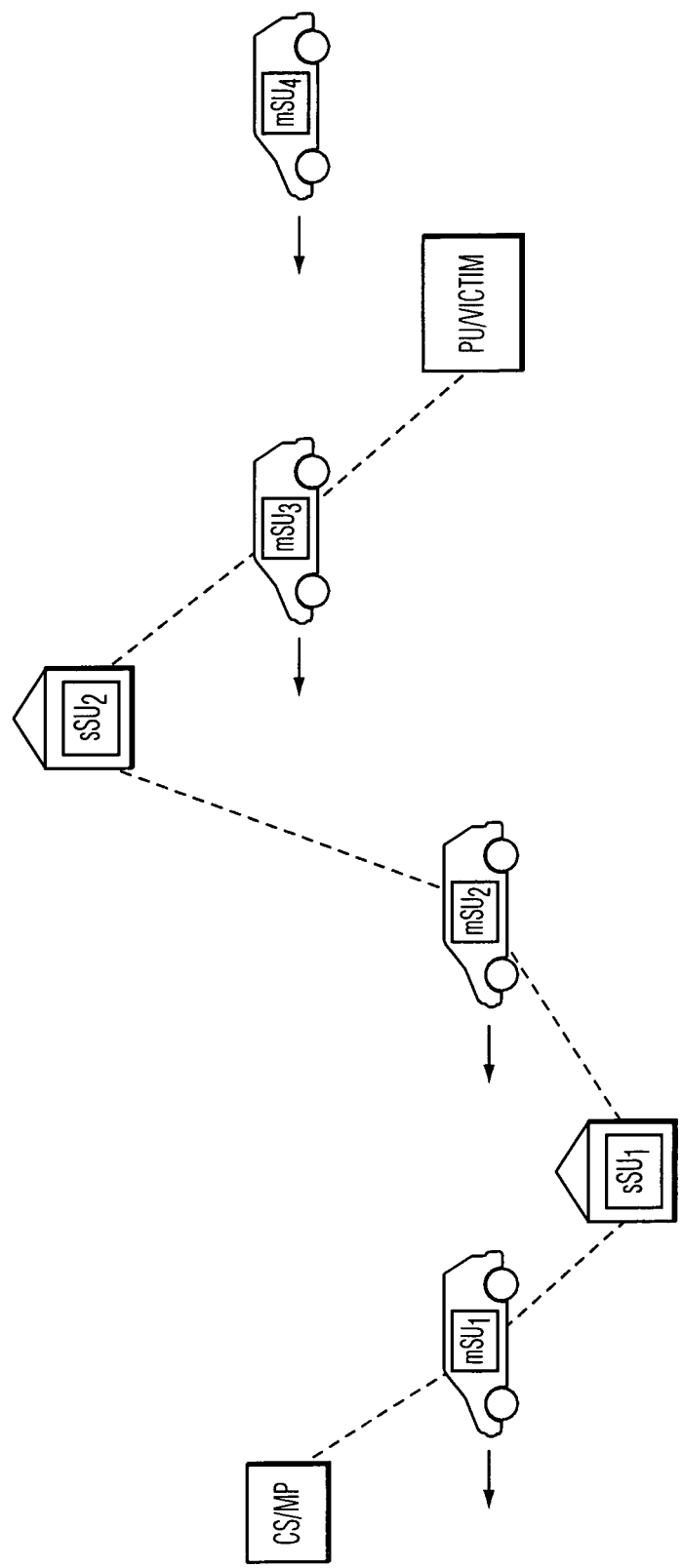
FIG. 24A shows a Network of mobile and stationary SUs linking PU and CS, at (early) time, $t_1$.
Figure 24B:
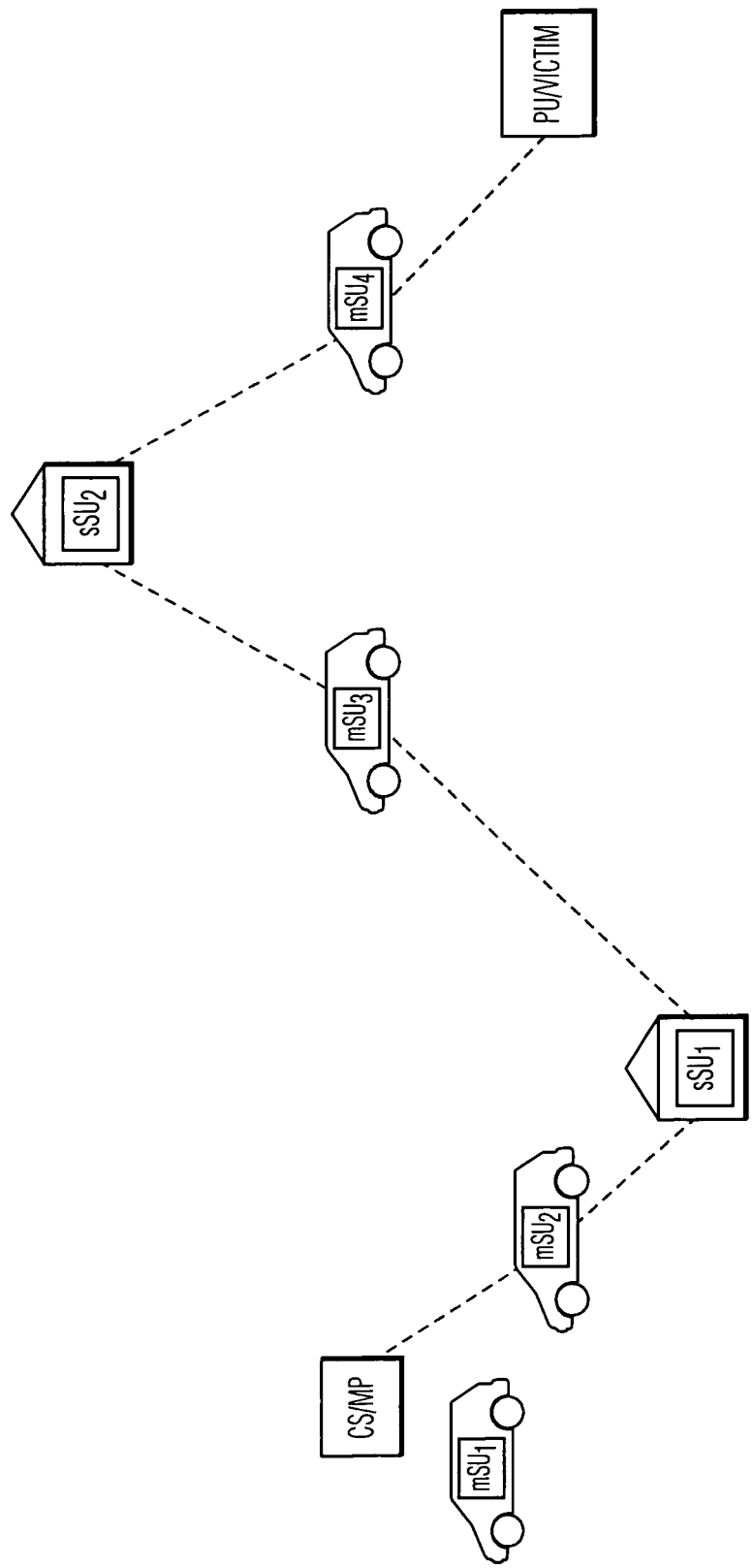
FIG. 24B shows a Network of mobile and stationary SUs linking PU and CS, at (later) time, $t_2$.

FIGS. 24A and 24B show a network of SUs linking the central station/medical professional (CS/MP) with the portable unit/victim (PU/MP). As discussed above in conjunction with FIG. 22, the stationary units in motor vehicles are not really stationary, but continue to be so called, in accordance with the naming convention of U.S. Ser. No. 10/460,458. Two types of SUs are shown:
A) mSUs: mobile SUs, located in motor vehicles; and
B) sSUs: (truly) stationary SUs, located in homes.

In FIG. 24A, the signal path from CS to PU is: CS to mSU to $sSU_1$ to $mSU_2$ to $sSU_2$ to $mSU_3$ to PU. (Signals passing from one entity to another are denoted by broken lines.) The path from PU to CS would include the same entities listed in reverse order. Although the example in the figure shows an alternating sequence of sSUs and mSUs, one could have a network in which:
A) all of the SUs are sSUs;
B) all of the SUs are mSUs;
C) there are a plurality of mSUs directly linked to each other (without an intervening sSU); and
D) there are a plurality of sSUs directly linked to each other (without an intervening mSU);

FIG. 24A shows the linkages at a time arbitrarily designated as $t_1$. At a later time, designated as $t_2$, the four motor vehicles have each moved to the left as shown in FIG. 24B. (The arrows in FIG. 24A indicate the direction of travel of the motor vehicles.) $mSU_1$, at $t_2$, is no longer in a position to link the CS and $sSU_1$ but $mSU_2$ is in such a position, and performs the aforementioned link. Similarly $mSU_3$, at $t_2$, is no longer in a position to link the $sSU_2$ and the PU (as it did at $t_1$), but it can link $sSU_1$ and $sSU_2$, and does so. $mSU_4$, at $t_2$, is no longer in a useless position; At $t_2$ it can link the PU and $sSU_2$, and does.

Motion of the SUs need not be all in the same direction, or in any particular direction. Each mSU may:
A) communicate as part of an SU-vehicle communications system pair, as shown in FIG. 22, elements 1806, 1830, 1808;
B) communicate without using the vehicle communications system; or
C) represent only the vehicle communications system, in an embodiment in which some or all of the vehicles do not have SUs, or in which some or all of the vehicles do not use their SUs.

The PU/victim in FIGS. 24A and 24B could also be an ICD/victim, i.e. a victim in whom an ICD is implanted which is capable of communication with a nearby SU, as described in U.S. Ser. No. 10/460,458.

Each SU may be coupled to a routing device which lets it:
A) find the next nearest SU;
B) poll multiple (or all of the reachable) SUs to determine the appropriate next SU; and/or
C) cause a plurality of reachable SUs to contact and obtain information concerning position and/or signal strength and/or availability of downstream neighboring SUs; and each of these downstream SUs may obtain similar information from a plurality of further downstream neighbors; and this step may be repeated one or more times with successively further downstream neighbors; with the aggregated information used algorithmically to construct an optimum communications route in both directions between the PU and the CS, using such algorithms and techniques as are known in the art.

Alternatively, the communications route may be determined entirely by the central station, which does so using:
A) GPS information indicating the location of each mSU;
B) stored information about the location of each sSU;
C) information known to it about total system volume, at that moment in time.

In this case the CS would pass this routing information on to the constituents of the route by either:

A) passing information about the complete route (e.g., that at $t_1$, the route from CS to PU is $mSU_1$ to $sSU_1$ to $mSU_2$ to $sSU_2$ to $mSU_3$ and the return route is the reversed sequence); or
B) passing routing information directly from the CS to each constituent of the route.

Overview of Invention 10 (FIGS. 25-31)

During the past few years it has become clear that for certain victims of cardiac arrest, the administration of CPR prior to a shock, improves the outcome. It has, for a longer time, been clear that CPR is also necessary for victims who have hypotension or so-called electromechanical dissociation during an arrest. The inventions described herein allow for the automatic provision of this modality, with control and monitoring of the CPR device by the MP.

Detailed Description of Invention 10 (FIGS. 25-31)

Figure 25A:
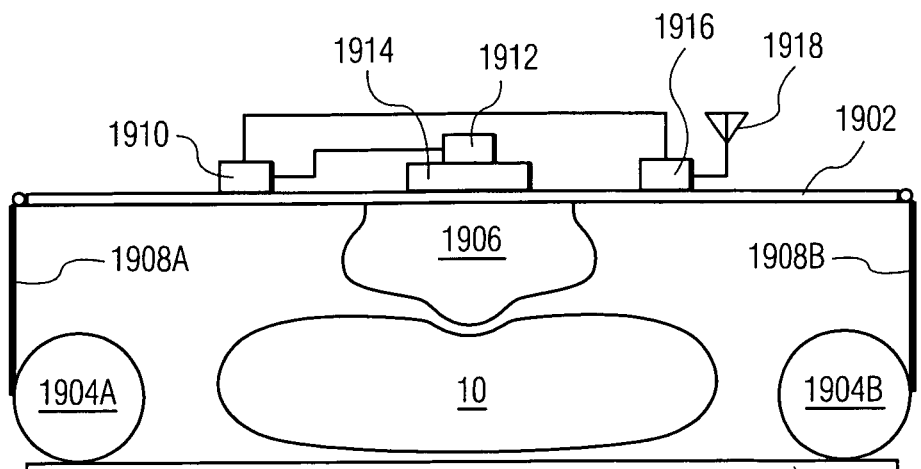
FIG. 25A shows a Biplane CPR device, frontal view.

FIG. 25 shows a biplane CPR device and a variation on its design. Referring to FIG. 25A, "biplane" refers to the fact that during operation, the rigid planar element lying above the victim 1902 is parallel to the rigid element 1900 which lies beneath victim 10 (shown in cross sectional view). To achieve chest compression, servos 1904A and 1904B take up respective belts 1908A and B which causes 1902 to be pulled downward. This causes rigid or semi-rigid element 1906, placed over the victim's sternum, at the appropriate point rostral to the xiphoid process, to be pressed downwards, effectuating a chest compression. Other shapes of 1906 are possible. It is possible that 1906 would come in multiple sizes and shapes (including various contact areas) to fit different victims. The servos may reel in the belts directly onto their rotating shaft, or onto a different shaft connected to the servo shaft by either one or more gears, belts, clutches or combinations of these. A ratchet wheel may be used to create an impulse, i.e. a sudden, brief increase in compressive force. Relaxation (i.e. release of the compression) may be either a) passive (i.e. by interrupting the servo power supply, or b) active (i.e. by reversing current flow, when a DC motor is in use, c) by reversing the direction of the shaft which takes up belts 1908A and B (i.e. by changing the gear arrangement which links the servo shaft and the belt take-up shaft; or d) by activating another servo (not shown) which moves in the opposite direction of 1904A and B. 1902 may be spring-loaded from above and/or below (not shown) or have damping apparatus above and/or below.

Apparatus within a gear, clutch or belt arrangement which attaches the servo shaft to the belt-uptake shaft may be designed to allow slippage when the torque reaches a certain value, to prevent excessive amount of applied pressure.

In order to maintain ideal geometry (which entails keeping 1902 parallel to 1900), a level measuring transducer 1914 may be used to monitor deviations from horizontality for 1902. Such deviations, if any are processed by power supply/electronics package 1910, and sent to transmitter 1916, antenna 1918, and from there to another antenna attached to a receiving apparatus/electronics/data package which generates a corrective signal which is applied to one or both servos. Alternatively, the link between the level detector and the servos could be a direct electrical connection. Another level-measuring transducer 1912 is shown for detecting deviations from parallel (to 1900) alignment that are orthogonal to those detected by 1914. These sorts of deviations will be important if an arrangement with four servos (analogous to that shown in FIG. 26B). Such deviations could also be important with a two-servo apparatus, if there are a series of belts on each side of the apparatus, all moved by the same servo but with each belt linked to the servo through its own belt/gear/clutch apparatus. In the figure, 1910 uses the same power supply/electronics/data package and transmitter/antenna as does 1914.

To facilitate setup, at least one of servos 1904A and B would initially not be attached to element 1900, allowing 1900 to be more easily positioned under the victim. Once 1900 is placed beneath 10, the unattached servo(s) is/are securely fastened to 1900.

Embodiments of the apparatus which use non-servo types of motors, as are known to a person skilled in the art, are also possible.

Apparatus which allows automatic ventilation of the patient may be coupled to the aforementioned, using technology that is known in the art. Proper control and synchronization of this apparatus with the chest compression rhythm is discussed below.

Figure 25B:
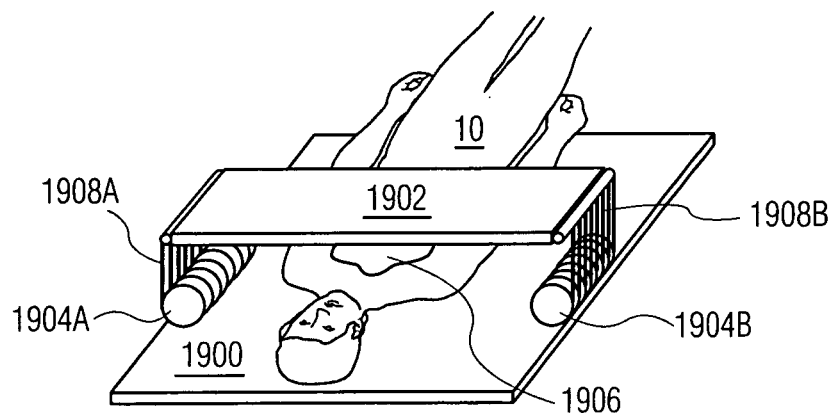
FIG. 25B shows a Biplane CPR device, oblique elevational view.

FIG. 25B shows an elevational oblique view of the same victim-apparatus combination as is shown in FIG. 25A.

Figure 25C:
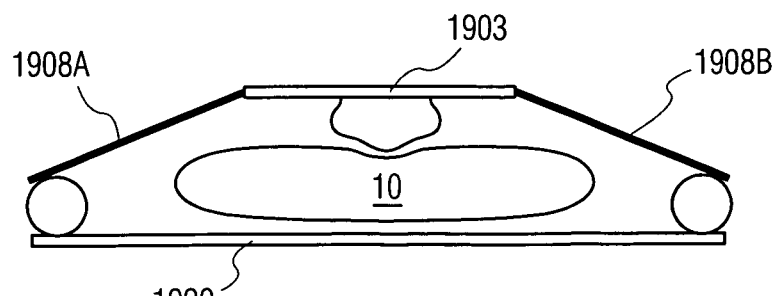
FIG. 25C shows a Biplane CPR device, frontal view, asymmetric plane dimensions.

FIG. 25C shows a variation in which 1903 is less wide than 1900. An advantage of this variation is ease of storage and the ability to control unintended right/left motion of 1903/1906 by lengthening or shortening one of 1908A or B. A disadvantage is that only a fraction of the force applied to belts 1908 is transmitted downward. Yet another variation (not shown) would have the width of 1903 greater than that of 1900. The advantage/disadvantage situation is the same as with the shortened version of 1903, except that storage becomes a disadvantage.

FIG. 26 shows a "triangular" CPR, so-called because of the approximate triangle formed by the two force-supplying belts 1922A and B, and the under-victim element 1901.

Figure 26A:
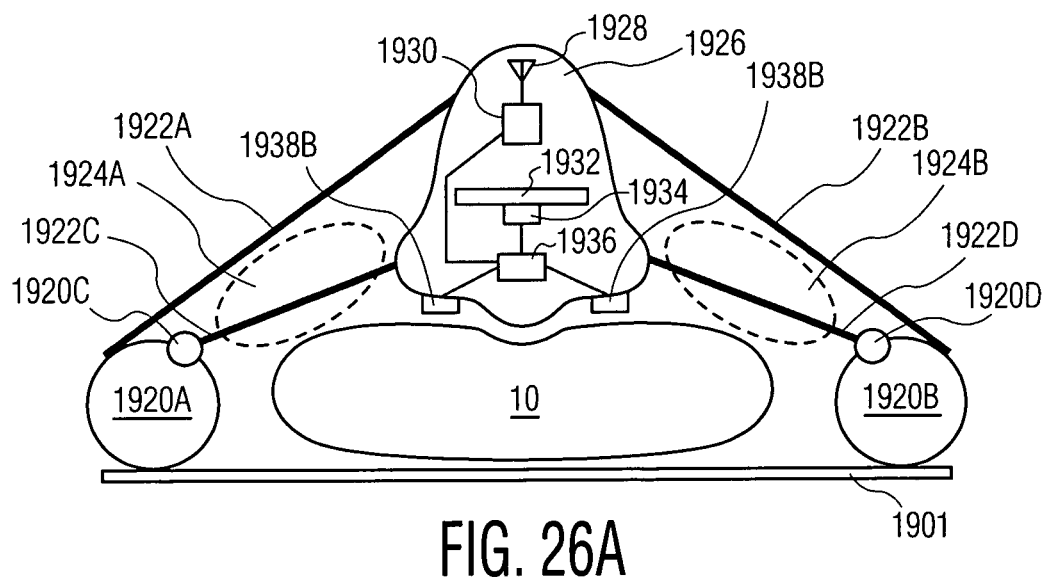
FIG. 26A shows a Triangular CPR device, frontal view.

In FIG. 26A, which shows a cross-sectional view, many of the elements are analogous or identical in function to those in the aforementioned biplane CPR device:
a) 1901 is analogous to 1900;
b) 1920A and B are analogous to 1904A and B;
c) 1922A and B are analogous to 1908A and B;
d) 1926 is analogous to 1906;
e) 1930 is analogous to 1916;
f) 1928 is analogous to 1918;
g) 1932 is analogous to 1914;
h) 1934 is analogous to 1912; and
i) 1936 is analogous to 1910.

Elements in the triangular device which are not analogous to those in the biplane device include:
a) belts 1922C and D, and servo motors 1920C and D. The belts extend from respective positioning/orienting servos 1920C and D to sternal compression element 1926. These latter two servo motors receive control signals which are based on i) the level-sensing apparatus (with transducers 1932 and 1934) within 1926, and ii) pressure transducers 1938A and B located at the base of 1926. These servos—as was the case with 1904A and B—may receive their information either via RF link or by direct connection. They allow more precise manipulation of 1926. For example: 1926 could be moved to the left (in the figure) by simultaneously shortening each of belts 1922A and C. Alternatively, 1926 could be rotated clockwise by shortening each of 1922B and C (while allowing 1922A and D to lengthen). Embodiments of the invention without the positioning/orienting belts and servos are possible. (Similarly embodiments of the biplane CPR device containing a second set of belts and servos for positioning/orienting [with a diagonal orientation of the additional set of belts] are possible.) Embodiments of the inventions in which the orienting/ positioning function of servos 1920C and D are performed by 1920A and B (in addition to the 1920A and B primary function of providing the power for chest compression), such that a system of gears, belts and/or clutches allows a different amount of force (if any) to be applied to 1922C and D, compared to that applied to 1922A and B, are possible. Embodiments of the invention in which belts 1922A and C are replaced by a single belt (as are 1922B and D) which is either i) a closed loop, which runs along the respective side of 1926, held in place by "inverted" u-shaped guides; ii) an open loop which is secured at one low point and one high point on the appropriate side of 1926; or iii) an open loop which is secured at two points within the servo assembly, and which runs along the respective side of 1926, held in place by "inverted" u-shaped guides;

b) optional inflatable elements 1924A and B. These, when present, also help maintain the position and orientation of 1926. They may be present in addition to 1920C and D/1922C and D, or instead of it; or neither of the two systems may be present. They may be inflated before or after positioning of the apparatus on the victim, by either the CPR device or a separate pressure source. Their inflation may be: i) such that the volume that they contain is fixed; ii) such that the volume that they contain is dynamically varied, by the CPR device, e.g. to maintain a constant pressure within the bag during chest compression, or to properly position the bag using telemetry information from level sensors 1932 and 1934. In an alternative embodiment of the invention, the bags may be filled with either a liquid or a gel.

Apparatus which allows varying the size and shape of the footprint of 1926 on the sternum is possible for this invention and for 1906 and the biplane device. The variation could be remotely controlled or manually manipulated. The remotely controlled version would have a receiver within 1926 (or 1906) which receives signals which a) manipulate the opening and closing of valves within 1926 (1906) which control the distribution of a fluid within 1926; or b) electromagnetically manipulate the orientation and position of small but rigid elements within 1926 (1906).

In an alternative embodiment of the invention (also applicable to the biplane version), elements 1938A and B may be ultrasound probes (including sources/detectors), which collect data to on the position/orientation of 1926 (1906) with respect to the torso margins to assure placement of 1926 (1906). In this situation, 1938A and B would likely be placed in a more lateral position on 1926 (1906) to allow visualization of the torso edges. Alternatively, positioning/orienting may be aided by one or more light sources on the victim-side of 1901 (1900) which are detected by detectors on the sides of 1926 (1901). Still other alternative embodiments use a light source on 1926 (1901) and a detector on 1901 (1900) or a light source and detector on the same element, with a mirrored surface on the opposing element. Alternatively, positioning/ orienting could be aided by visual information from the video camera within the RCD (as described in U.S. Ser. No. 10/460, 458), operating with either the biplane or the triangular device.

Apparatus which allows automatic ventilation of the patient may be coupled to the aforementioned, using technology that is known in the art. Proper control and synchronization of this apparatus with the chest compression rhythm is discussed below.

Figure 26B:
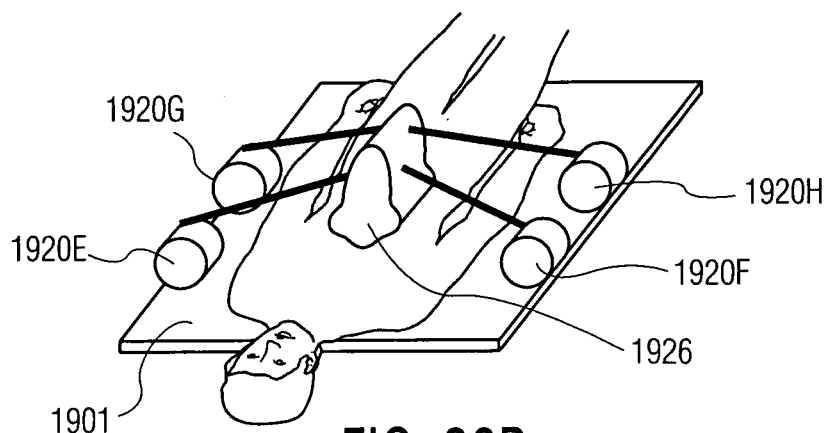
FIG. 26B shows a Triangular CPR device, oblique elevational view.

FIG. 26B shows an oblique elevational view of the victim and device in FIG. 25A. In this figure, positioning/orienting servos and belts are absent. The presence of two of each of compression servos allows for better positioning/orienting and stability of 1926, compared to the case with only two compression motors. Furthermore, by positioning servos 1920E and F closer to the head-end of 1901 than is the head-end of 1926, and by positioning servos 1920G and H closer to the foot-end of 1901 than is the foot-end of 1926, it would be possible to aid in the positioning of 1926 along the head-foot axis. If, during use, it began to drift toward the head end, an increase in the torque applied by 1920G and H, and a decrease in the torque applied by 1920E and F, would help restore 1926 to its proper location. Such head-foot position correction could be used in conjunction with the biplane device. Still other alternative embodiments are possible in which:

a) two (or four) large servos provide chest compression and four smaller ones provided head-foot position correction;

b) only two (rather than four) servos are used for head-foot position correction (one on each side of the victim), and c) a system with two or four compression servos, two or four head-foot positioning servos and two or four right/ left positioning/orienting servos.

Embodiments of the apparatus which use non-servo types of motors, as are known to a person skilled in the art, are also possible.

Figure 26C:
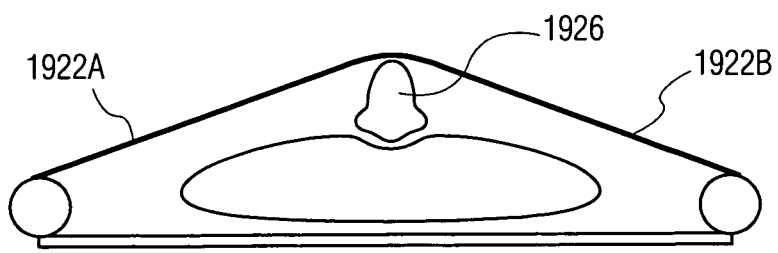
FIG. 26C shows a Triangular CPR device, frontal view, asymmetric plane dimensions.

FIG. 26C shows another embodiment of the invention in which belts 1922A and B attach to 1926 at its top. In yet another variation, the two belts may then be replaced by a single belt which either a) slides freely through an inverted U-shaped guide at the top of 1926 or b) is secured to the top of 1926.

Figure 26D:
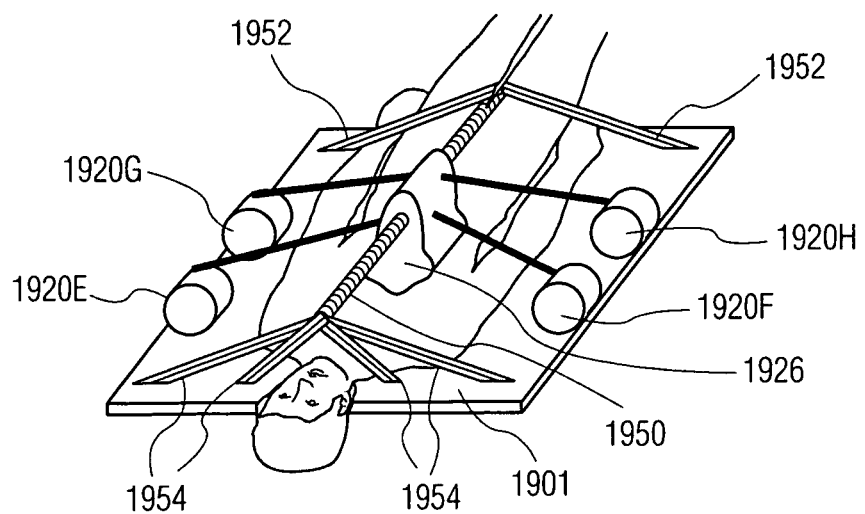
FIG. 26D shows a Triangular CPR device, oblique elevational view, variation with central positioning rod.

FIG. 26D is a variation of the device shown in FIG. 26B. In this embodiment, right to left drift or deviation of 1926 is prevented by a rod 1950 which passes through a hole in 1926. The head end of 1950 is supported by brackets 1954, the foot end by brackets 1952. Embodiments are possible with a) a larger or smaller number of 1952 or of 1954; and b) different positioning and or angulation of one or more of 1952 or 1954.

Figure 26E:
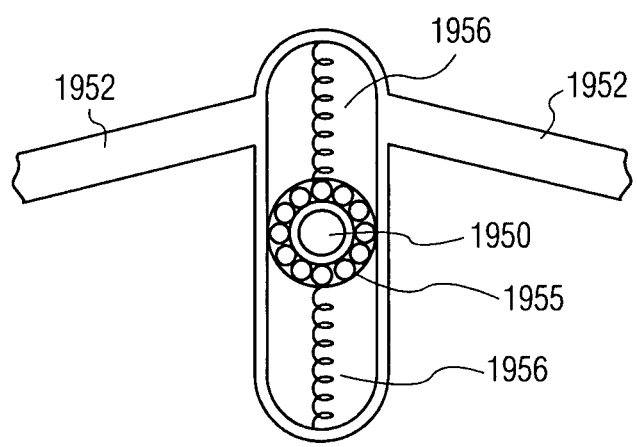
FIG. 26E shows a Triangular CPR device, central rod support detail.

FIG. 26E shows a detailed end view of the junction between brackets 1952 and rod 1950. Bearings and bearing housing 1955 allow for guided motion of 1950 in the up-down direction with a minimum of friction. Springs 1956 restore a neutral position to the end of 1950 when motors 1920 do not exert a downward force. Embodiments with only one spring are possible, as are embodiments without any springs and without any bearings. The junction at the head-end of the device, associated with brackets 1954 would be similar in structure, though need not be identical to that shown in FIG. 26E.

FIGS. 27-28 shows another means of providing automated chest compression. The essence of the approach is to create a sturdy box around the victim, by starting with an "exploded" version of the box, shown in FIG. 27A, sliding the flat, exploded version under the victim, then properly folding it (as shown in FIGS. 27B, C, D), and then adding on the compression device shown in FIG. 28B, to form the finished product as shown in FIG. 28A.

Referring to FIG. 27A, while sliding the flattened box (consisting of all of elements 2000-2020) under a victim, the hinge elements 2001A, 2001B, 2003A and 2003B are immobilized in the open configuration (such that each of 2000 [which is to become the bottom], 2002A and B [which are to become the sides] and 2004A and B [which are to become the top] are co-planar [i.e. they form a single flat sheet]). Immobilization may be achieved by either:

a) inserting rigid removable rods 2006A and B into fitted receptacles (indicated by the horizontal dotted lines) and thereby preventing folding; and/or b) inserting a four locking rods 2018 into their fitted receptacles. There are many possible mechanisms by which the insertion of each of 2018A and B could prevent folding, as are known in the art. In the mechanism shown in the figure, the insertion of the 2018 rods into (or rotation of the rods within) respective locks 2019 causes respective bars 2017 to rotate 90 degrees. Bars 2017A are shown in a position which prevents folding; bars 2017B are shown in the position which allows folding.

Passing the assembly under the victim (such that the victim's head ends up lying between 2012B and C, and the victim's legs are on either side of 2012A) may be further facilitated by the placement of bearings at various points on:

a) the under-surface (i.e. the side facing the ground during insertion) of each of 2002A and B, and 2004A and B, and perhaps 2000; and b) the over-surface (i.e. the side facing the victim) of each of 2002A and 2004A.

Once the assembly has been passed under the victim, each locking item must be unlocked, i.e. rods 2006A and B would be removed and locking rods 2018 would be rotated to cause bars 2017 to be in the unlocked position (vertically oriented in the figure).

Embodiments of the invention are possible with:
a) 2006-type rods, but not 2017/2018/2019 locks;
b) 2017/2018/2019 locks but not 2006-type rods;
c) no locking mechanism;
d) a larger or smaller number of 2006-type rods;
e) a larger or smaller number of 2017/2018/2019 locks; and
f) other types of locking mechanisms, as will be obvious to those skilled in the art.

Once the locking mechanism is removed, sections 2002A and B are folded so that they are vertically oriented (i.e. they make a 90 degree angle with respect to 2000), on either side of the victim. Each of sections 2004A and B are folded over the victim so that they make a 90 degree angle with each of 2002A and B.

Figure 27B:
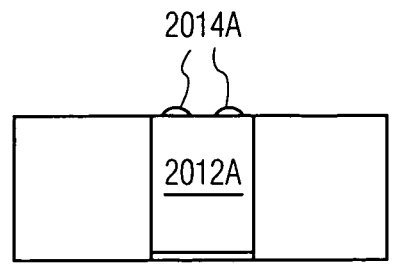
FIG. 27B shows a Rectangular CPR Box, folded, frontal view.
Figure 27C:
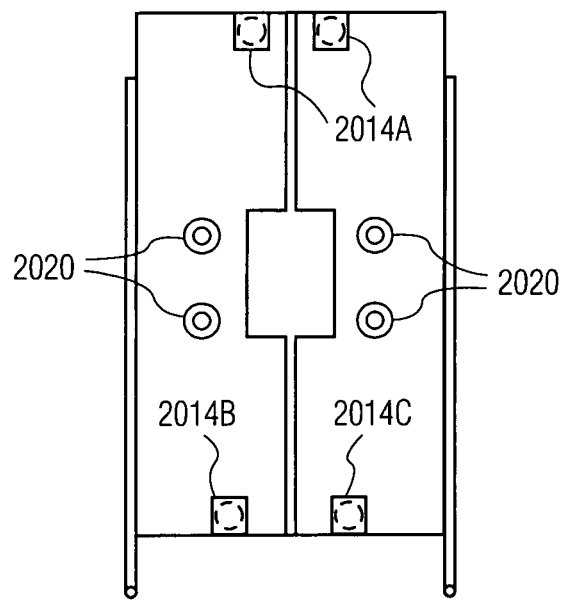
FIG. 27C shows a Rectangular CPR Box, folded, top view.
Figure 27D:
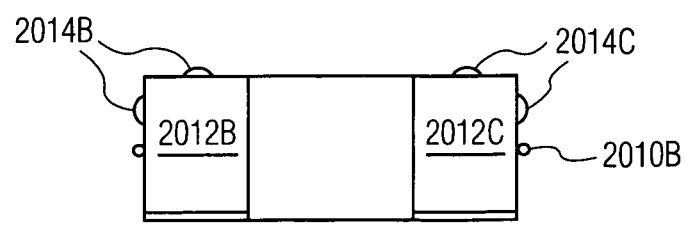
FIG. 27D shows a Rectangular CPR Box, folded, rear view.

The next task is to render the box rigid, such that the angles between adjacent walls becomes fixed at 90 degrees. One method of accomplishing this, shown in FIGS. 27A-D, is:

a) folding projection 2012A at the foot end up, so that it touches top sections 2004A and B;

b) securing it to top sections 2004A and B; In the embodiment of the invention shown in the figure, this is accomplished by snapping each of snaps 2014A to its counterpart 2016A (either 2014A or 2016A can be the male snap);

c) folding projections 2012B and C at the head end up, so that they touch top sections 2004A and B; and d) securing them to top sections 2004A and B; In the embodiment of the invention shown in the figure, this is accomplished by snapping each of snaps 2014B and C to their counterparts 2016B and C (either set can be the male snaps);

The partially assembled rectangular box is shown in FIGS. 27B (frontal view from foot end), 27C (top view) and 27D (frontal view from head end). The four holes 2020 accommodate the chest compression mechanism (shown in FIGS. 27I and 27J and are fitted preferably with threads so that a cylindrical support element with screw tips may be screwed into each.

Inflatable bladders 2008A and B are filled by pumping air or another gas or a fluid into each of tubes 2010A and B. When inflated, these prevent the victim in the box from moving/ drifting to his right or left during CPR, and thereby assuring that chest compression is properly delivered over the victim's sternum. They can also be used to move the victim to the right or left, if he was not properly centered at the time of the initial placement of the flattened box under him. Such movement could be facilitated by bearings or rods which are under the victim and can roll during such lateral movement (as illustrated in FIG. 28F in conjunction with the triangular CPR box, and discussed in conjunction therewith). Ideally such bearings or rods would be retractable, so that they do not impact the victim's back, once chest compression begins.

There are numerous possible variations of this invention including:

a) boxes with different sizes and/or boxes with different ratios of length:width:height than that shown in FIGS. 27A-D;

b) boxes with a hole on each side, so that the victim's arms may lie outside of the box;

c) boxes of different shapes, e.g.
  i) boxes whose front/rear silhouette is trapezoidal, rather than rectangular—e.g. such that the combined widths (i.e. the right-to-left dimensions) of 2004A and B are less than the width of 2000;
  ii) boxes whose side silhouette is trapezoidal, rather than rectangular—e.g. such that the length (i.e. the head-to-foot dimension) of 2004A and B are less than the length of 2000, and such that elements 2002A and B are trapezoidal in shape;
  iii) triangular-shaped boxes—discussed hereinbelow, in conjunction with FIGS. 28;

d) boxes with different placement/size of the cutout for chest compression;

e) boxes without inflatable bladders 2008A and B;

f) boxes with inflatable bladders in other locations (in addition to or instead on the victim's sides), e.g. above and/or below the victim; and g) as discussed hereinabove and hereinbelow, boxes with different means of maintaining the shape of the box (either in its flattened or in its rectangular configurations).

Figure 27E:
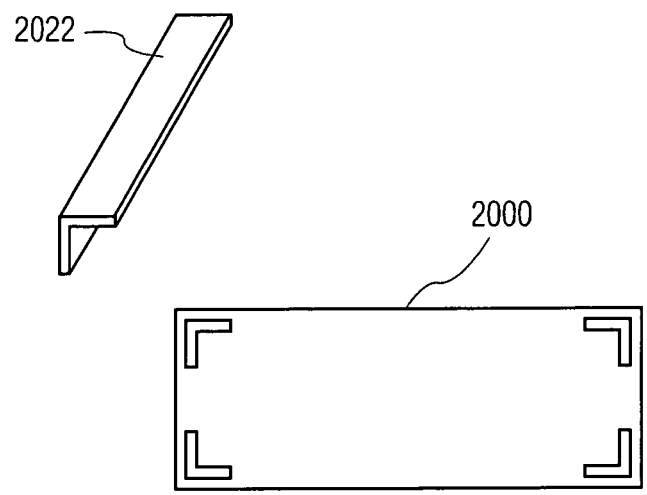
FIG. 27E shows a Rectangular CPR box, L-shaped support detail.

In order to prevent the folded CPR box from changing shape (such that its front profile, rather than rectangular, assumes the shape of a parallelogram), various means may be utilized, for fixing the angles between adjacent walls at a value of 90 degrees:

FIG. 27E shows a rigid L-shaped element 2022 to be inserted at each of the four junctions between adjacent walls of the assembled box, and a side view of the box with the L-shaped elements in place. The four 2022 could be secured to each of the two box walls with which each 2022 comes in contact using techniques known to those skilled in the art (and not illustrated in the figure). Embodiments with fewer than four 2022 are possible. Embodiments in which each of 2022 runs the entire length (from the head end to the foot end) of the box are possible, as are embodiments in which each of 2022 runs less than the full length; Embodiments are also possible in which there are separate 2022 for the head end and for the foot end, with a total of up to eight such 2022.

Figure 27F:
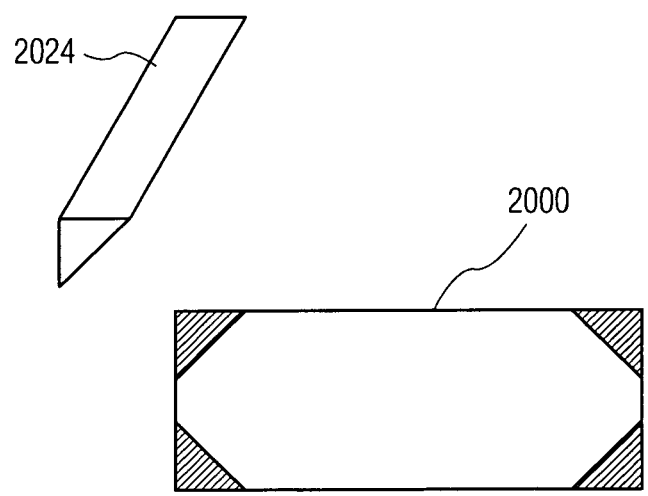
FIG. 27F shows a Rectangular CPR box, type-I triangular support detail.

FIG. 27F shows a rigid triangular element 2024 to be inserted at each of the four junctions between adjacent walls of the assembled box, and a side view of the box with the triangular elements in place. The four 2024 could be secured to each of the two box walls with which each 2024 comes in contact using techniques known to those skilled in the art (and not illustrated in the figure). Embodiments with fewer than four 2024 are possible.

Embodiments in which each of 2024 runs the entire length (from the head end to the foot end) of the box are possible, as are embodiments in which each of 2024 runs less than the full length; Embodiments are also possible in which there are separate 2024 for the head end and for the foot end, with a total of up to eight such 2024.

Figure 27G:
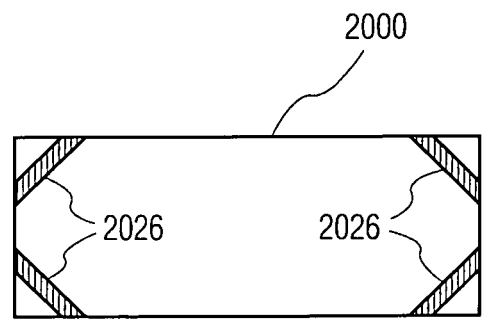
FIG. 27G shows a Rectangular CPR box, type-II triangular support detail.

FIG. 27G shows the use of four struts 2026 to secure the rectangular structure of the box. Each of the four 2026 could be held in place by snaps or by another fastening mechanism, using techniques known to those skilled in the art (and not illustrated in the figure). Embodiments with fewer than four struts on either end of the box are possible. Embodiments with such struts only at the head end, only at the foot end, or both (with up to eight such struts in total) are possible.

Figure 27H:
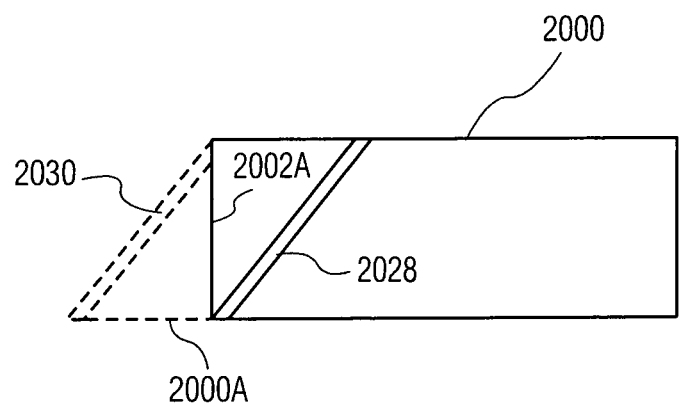
FIG. 27H shows a Rectangular CPR box, type-III triangular support detail.

FIG. 27H shows two additional methods of securing the rectangular shape:

a) The first method, a variation on the theme of FIG. 27G shows the use of a strut 2028 which extends from the lower left (in the figure) corner of the box to a point on the top wall. Embodiments with two, three or four such struts on either end of the box are possible. Embodiments with such struts only at the head end, only at the foot end, or both (with up to eight such struts in total) are possible. Each of the four 2028 could be held in place by snaps or by another fastening mechanism, using techniques known to those skilled in the art (and not illustrated in the figure).

b) The second method: The broken lines in FIG. 27H illustrate another support mechanism based on the inflexibility of the triangular structure: 2000A is a rigid extension of the bottom of the CPR box 2000. Either both of 2000A and 2000 are a single item, or, if separate, are joined so that the junction between them may not flex. 2030 is a strut which extends from 2000A to the junction of 2002A and 2004A, or (not shown in the figure) to another point on the outside of 2002A. 2030 may be placed at the head end, at the foot end, at points in between the head and foot end, or at multiple points. Alternatively, a wide version of 2030 may extend all of the distance from the head end to the foot end, or part of the distance (and, if part of the distance, there may be more than one such wide 2030). 2030 could be secured to each of 2002A (or the junction of 2002A and 2004A) and 2000A using techniques known to those skilled in the art (and not illustrated in the figure).

Any of the aforementioned support mechanisms may be utilized: a) alone; or b) in combination with one or more other ones of the aforementioned mechanism. They may replace on or more folding projections 2012A-C, or they may be present in addition to the folding projects.

Figure 27I:
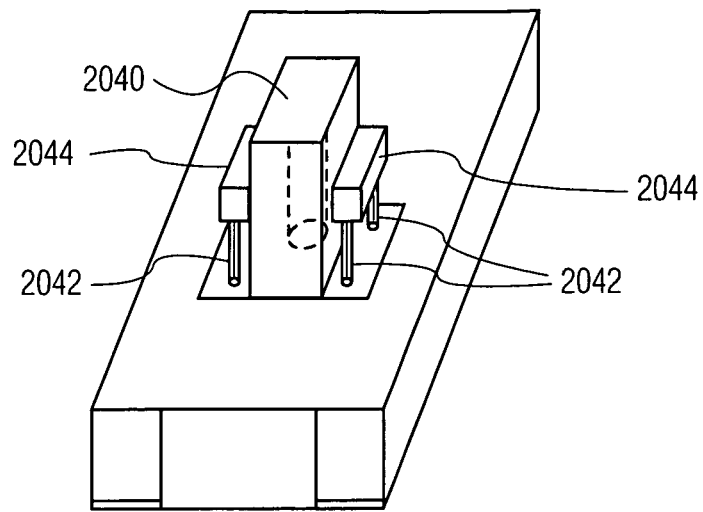
FIG. 27I shows a Rectangular CPR Box, assembled.

FIG. 27I shows the fully assembled rectangular CPR box, in an oblique elevational view from the head end, with chest compression device 2040 in place. Four support structures 2042 (three of which are visible) extend from 2040 and insert into the four receptacles 2020 (FIGS. 27A and C). In one embodiment of the invention they are manually screwed in by the person assembling the device (in which case screwdriver access, not shown, would be provided). In another embodiment, a motorized mechanism (also not shown in the figure), screws each of the four 2042 elements into place. Support structure housings 2044 are rigidly attached to the housing of 2040.

Figure 27J:
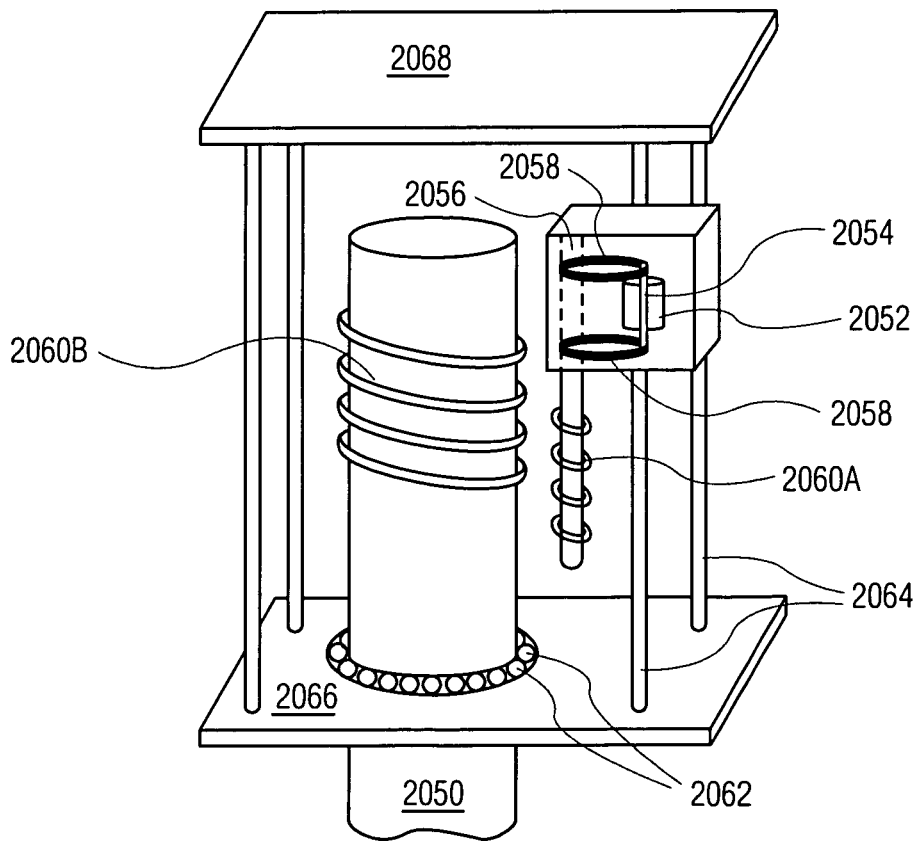
FIG. 27J shows a Detail of possible chest compression mechanism.

FIG. 27J shows one embodiment of the chest compression mechanism, which is contained within 2040, rotated 90 degrees with respect to its orientation in FIG. 27I. In this embodiment, compression shaft 2050 is moved up and down by motor 2052. The rotation of motor shaft 2054 is transmitted to shaft 2056 by belts 2058. Shaft 2058 includes worm-gear 2060A, which meshes with worm-gear 2062B on 2050. Preferentially, a ring-shaped arrangement of bearings 2062 (bearing housing not shown in the figure; lubrication system also not shown in the figure; both are known in the art) help reduce friction between 2050 and the base of its housing 2066, and help maintain proper vertical orientation of 2050.

Four support elements 2064 are shown, the one positioned on the front/right of the figure is partially cut away for illustrational purposes. A housing for the motor is shown, but support elements for the motor within the housing and for the motor housing itself, each of would be present, are not shown. In an alternate embodiment of the invention, shaft 2050 may extend beyond the top surface of the housing 2068, with, optionally, a ring of bearings that sits between the shaft and the upper portion of the housing.

Other embodiments of the compression device are possible including embodiments:

a) with a different gear arrangement;
  b) in which the worm gear 2060A (which drives 2060B) is on the motor shaft (i.e. without second shaft and without belts 2058);
  c) in which other types of gear arrangements link rotational motor energy to 2050;
  d) in which the motor is replaced by a coil of wire which surrounds an iron (or other magnetic material)-containing 2050, and whereby the passage of a pulse of electrical current through the coil causes vertical movement of 2050 which causes chest compression; In this embodiment, relaxation of 2050 (i.e. its upward motion following the compression) could come from a spring-loading arrangement (with the spring(s) pulling 2050 up after a compression) or could come from a second coil, placed either above or below the aforementioned coil, which, when a current passes through it, actively pulls 2050 upward; and
  e) with a ratchet arrangement which causes a non-rectangular shape to the compressive force vs. time envelope.

Still other mechanical arrangements will be obvious to those skilled in the art.

Apparatus which allows automatic ventilation of the patient may be coupled to the rectangular CPR box, using technology that is known in the art.

FIGS. 28A-F show a triangular version of the CPR box. It is similar to the aforementioned rectangular CPR box except for:

a) the shape differences between the boxes; and
  b) the inclusion of a shelf (which, when the box is assembled, will be horizontally oriented) for supporting the chest compression device.

Some features and their corresponding elements (e.g. 2006A and B, 2017A and B, 2018A and B, 2019A and B), which are shown in the rectangular box figures, are not shown in conjunction with the triangular box figures; Their absence in FIG. 28 is not intended to imply their absence from the triangular box embodiment of the invention. They are omitted from FIG. 28 for purposes of simplification; if included in the triangular embodiment, their placement and function would be analogous to their placement and function in the rectangular embodiment.

Bottom portion 2100 is attached to left portion 2102A by hinge 2101A, and is attached to right portion 2102B by hinge 2101B. As was the case with the rectangular box, means for rendering the hinged sections inflexible, with inserting portions at a 180 degree angle with respect to each other during insertion under the victim, would be provided, and would be analogous to those illustrated in FIG. 27A. Means analogous to those illustrated in FIGS. 27E-H (for maintaining box shape in the folded state) are optional; the fact that the outer structure of the box is triangular in shape gives it a means of maintaining rigidity that is not implicit in the structure of a rectangular box. Projections 2110A-C are analogous to 2012A-C, each showing two un-numbered projections which may contain a snap or other fastening device (not shown, known in the art) to allow fastening of the top right side of the assembled box to the top left side. (The counterpart to which each snap would be secured, analogous to 2016A-C in FIG. 27A would also not shown, would also be present.)

Hinge 2103 attaches shelf 2104 to 2102B. When the device is assembled, this shelf will support the Chest compression device. Hole 2106 will accommodate compression shaft 2050, and screw receptacles 2108 will accommodate projections 2042. Projections 2112 will be fastened to 2102A (snaps, snap receptacles, other fastening means not shown, known in the art). Optional projections at the head and foot end, analogous to 2102A-C are not shown; If incorporated they would provide: a) additional structural support; and b) prevent motion of the victim along the head-foot axis during device use.

Figure 28A:
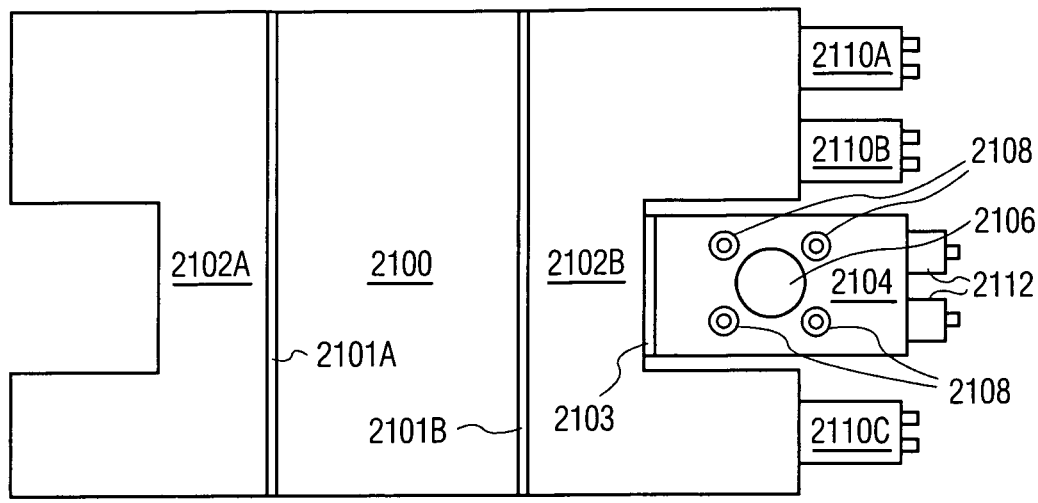
FIG. 28A shows a Triangular CPR Box, unfolded.

During use, the device is initially maintained in approximately the configuration shown in FIG. 28A while it is passed under the victim. Walls 2102A and 2102B are then folded upwards so that the segments that become their top portions touch, and are fastened to each other; while 2104 is folded so that its plane is horizontal, and is attached to what becomes the top portion of the cut-out section of 2102A.

As was the case with the rectangular version of the CPR box, numerous variations in the design of the triangular box are possible including:
  a) boxes of different overall size;
  b) boxes with different ratios of height:width:length;
  c) boxes with different placement of the cut-out portion (with regard to its height above 2100 [when assembled] and with regard to its position along the head-foot axis);
  d) boxes with different sized cut-out portions;
  e) boxes with different head-to-foot dimension for shelf 2104 [which must necessarily be no larger than the size of the cut-out region];
  e) boxes with arm holes; and
  f) boxes which form either an equilateral triangle (shown in the figure), an isosceles triangle, or boxes in which the length of each side of the triangle is unequal. For any boxes in which the sections corresponding to 2102A and B are of unequal size, the cut-out section must be proportioned so that shelf 2104 lies horizontally, after folding to the partially assembled state has taken place.

Figure 28B:
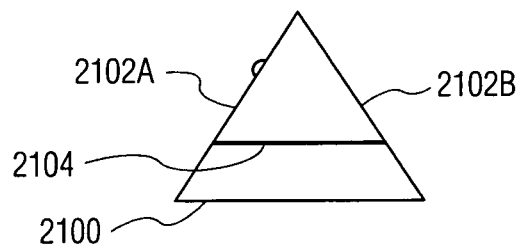
FIG. 28B shows a Triangular CPR Box, folded, frontal view.
Figure 28C:
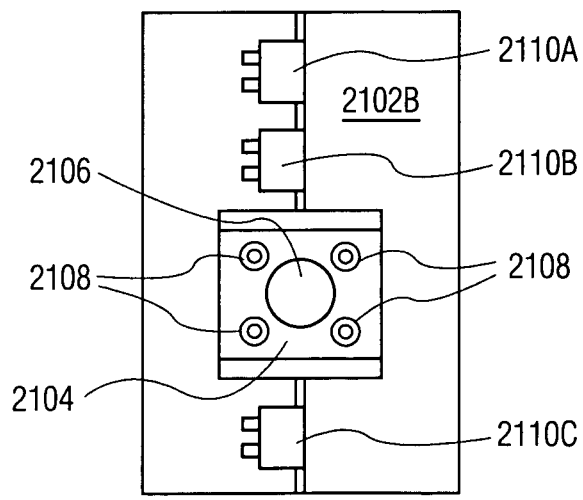
FIG. 28C shows a Triangular CPR Box, folded, top view.
Figure 28D:
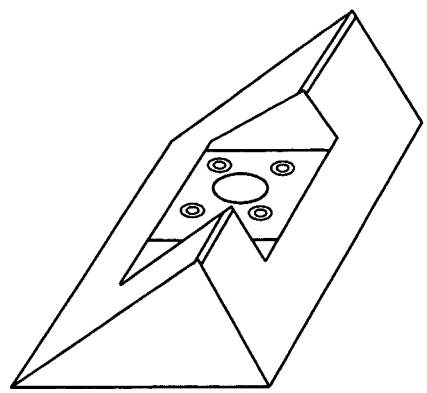
FIG. 28D shows a Triangular CPR Box, partially assembled, oblique elevational view.

FIG. 28B shows a frontal view of the partially assembled device. FIG. 28C shows a top view of the partially assembled device, with shelf 2104 visible through the opening in the top. FIG. 28D shows a front elevational view of the partially assembled device, with shelf 2104 visible through the opening in the top.

Figure 28E:
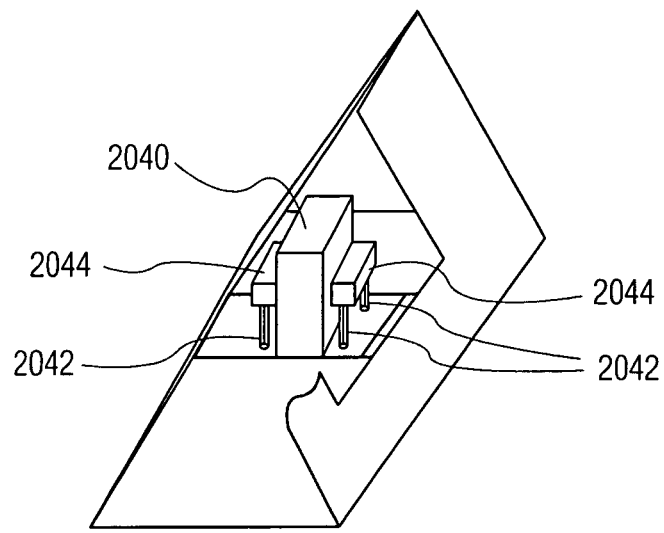
FIG. 28E shows a Triangular CPR Box, assembled, with right side partially cut away, oblique elevational view.
Figure 28F:
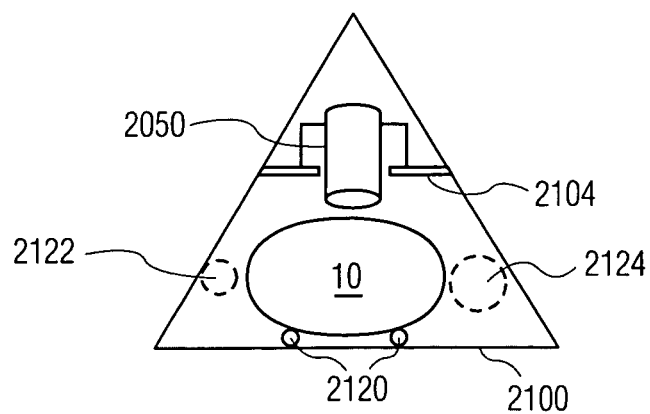
FIG. 28F shows a Triangular CPR Box, assembled, side view.

FIG. 28E shows a front elevational view of the assembled triangular CPR box with chest compression device in place and with the top/front portion of the right side cut away to allow visualization of the placement of the chest compression unit 2040. Unit 2040, its support structure elements 2042 (which, when incorporated in the triangular CPR box, insert into holes 2108 [which are preferably fitted with threads so that a cylindrical support element with screw tip may be screwed into each]) and support structure housings 2044, are identical in structure and function to their counterparts (discussed in conjunction with the rectangular CPR box, and shown in FIGS. 27I and 27J).

FIG. 28F shows a frontal view of the assembled device, with a cross sectional view of a victim superimposed. In the embodiment of the invention shown in the figure, the victim is lying on bearings 2120 which facilitate his being moved along the right-left axis. The bearings are optional, and could, optionally be replaced by one or more cylindrical rods which run parallel to the head-foot axis. Either the bearings or rods could be optionally retractable after the victim has been properly positioned. Retraction would:
  a) prevent undesirable right-left victim motion during CPR; and
  b) prevent skin surface injury due to compression forces concentrated in the vicinity of the bearing or rod.

In the un-retracted state, the bearings and/or rods would also facilitate sliding the unfolded triangular CPR box under the victim. Such bearings or rods could also be used in conjunction with the rectangular CPR box.

Inflatable bladders 2122 and 2124, analogous in structure and function to 2008A and B, would facilitate (especially with bearings/rods in the non-retracted state) moving the victim to the right or left for proper positioning. (Alternatively [in the case of both the triangular and the rectangular CPR boxes], the position of the chest compression device could be altered to match patient location.) In the figure, bladder 2124 has been additionally inflated and bladder 2122 has been partially deflated, to move the victim to the left in the figure.

Apparatus which allows automatic ventilation of the patient may be coupled to the aforementioned triangular CPR box, using technology that is known in the art.

Heretofore, rectangular, triangular and trapezoidal-shaped boxes have been described; many other shapes are possible. All but triangular shaped frameworks will require some additional support mechanism to assure stability of the framework during chest compression. The support mechanism may be either in the form of a) struts or other cross-pieces attached to adjacent surfaces (which thereby create a triangular structure, e.g. 2026 [FIG. 27G], and 2028 [FIG. 27H]), or b) rigid bodies (e.g. 2022 [FIG. 27E]) which may be either inserted or positioned to contact adjacent, otherwise flexible joints (where flexible is defined as a situation in which the angle between two joint constituents may be easily changed).

A vehicle-mounted CPR device has these advantages:
  a) It can provide CPR for a victim who is alone; and
  b) It allows easy movement of apparatus which might be heavier than some people can comfortably move.

Figure 29A:
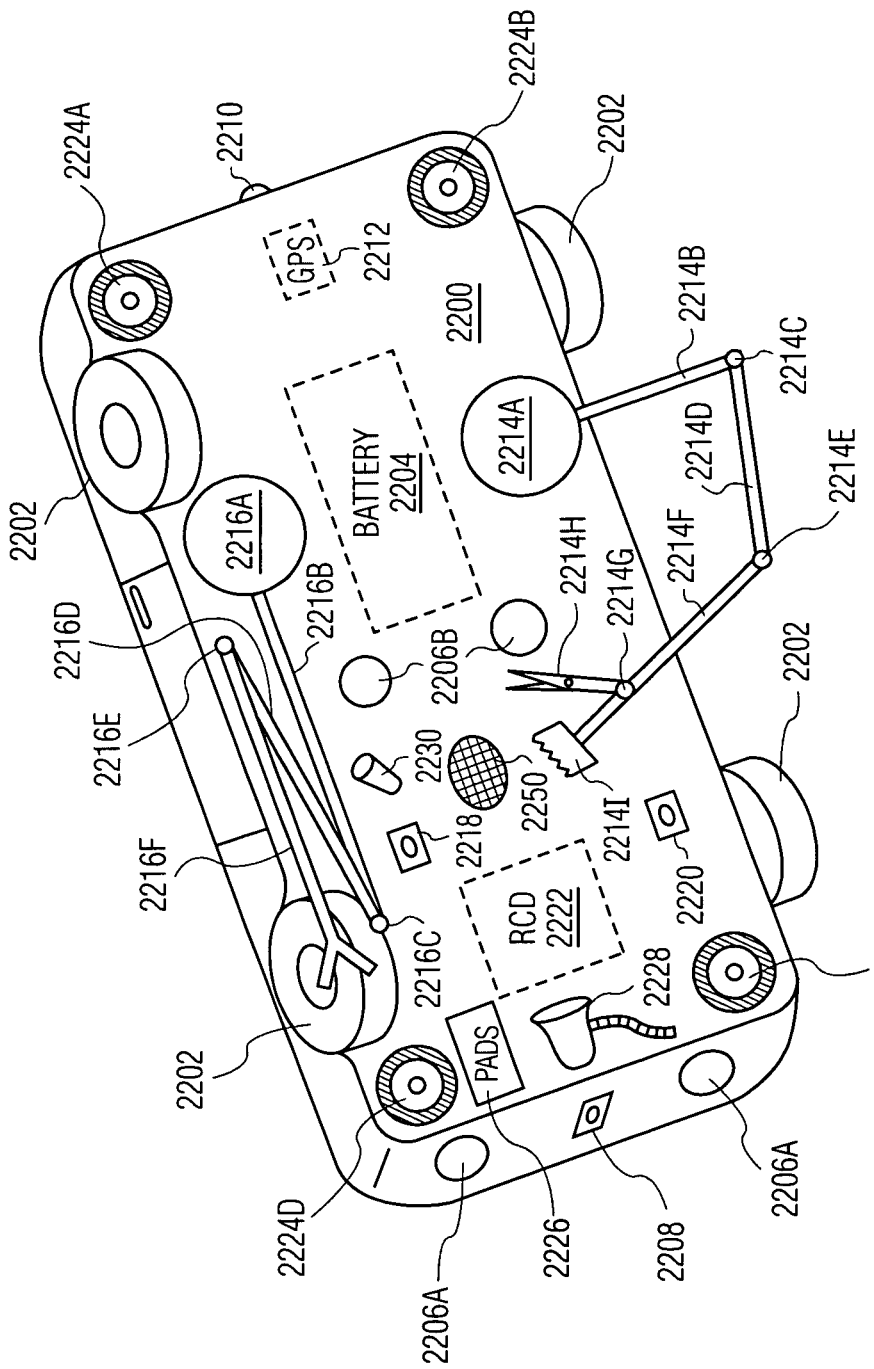
FIG. 29A shows a Vehicular CPR device and resuscitation device.
Figure 30:
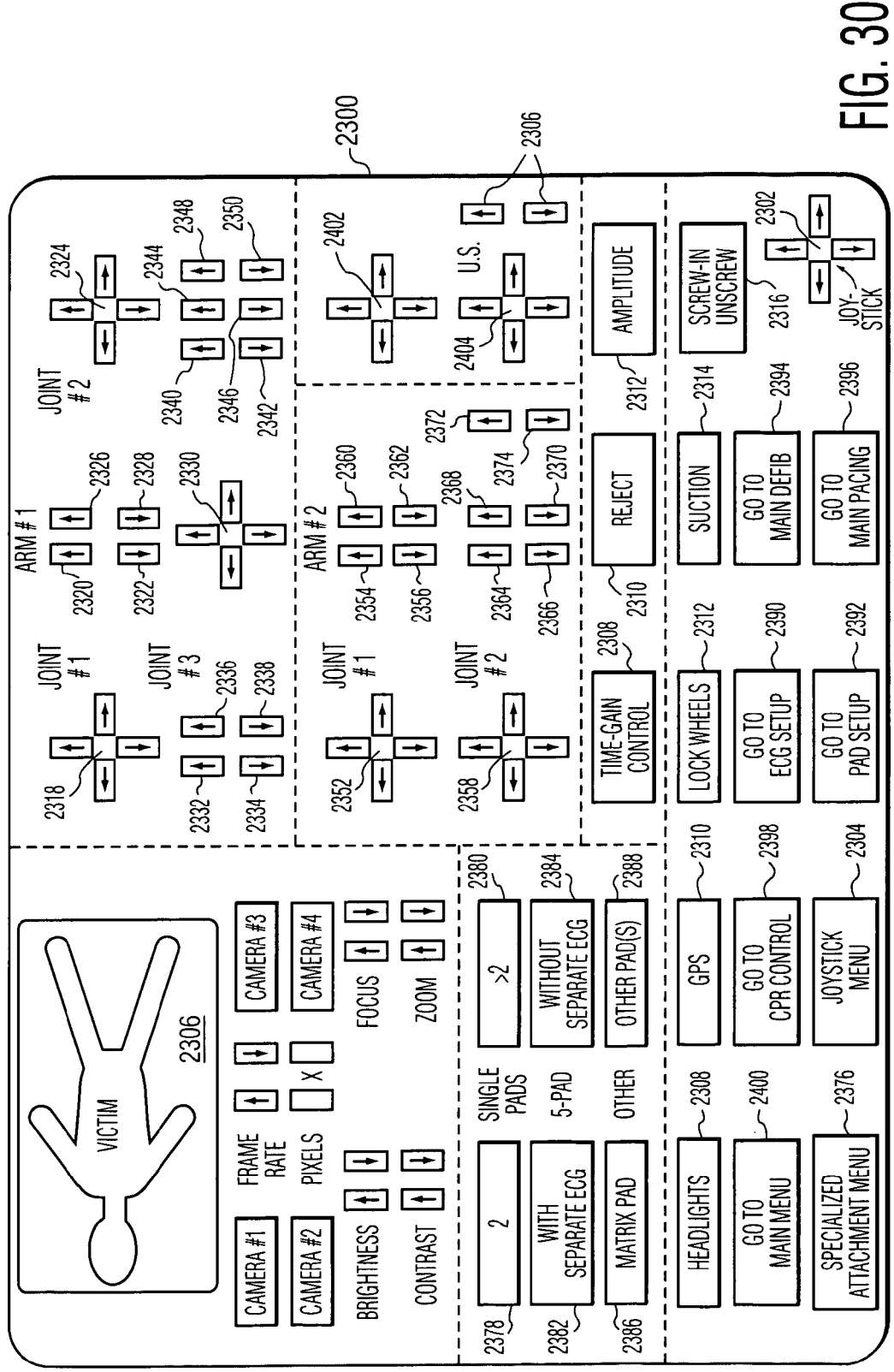
FIG. 30 shows a Vehicular CPR device control screen.

An oblique elevational view of one embodiment of such a vehicle is shown in FIG. 29A. The control panel for such a vehicle is shown in FIG. 30 and is discussed hereinbelow.

The vehicle is powered by batteries 2204 (The broken line forming its perimeter indicates its placement within vehicle 2200.), which charge via a charger which may be powered by current from a building source, or current from a motor vehicle, e.g. an automobile (see discussion associated with FIG. 22, hereinabove). In a preferred embodiment of the invention, vehicle movements are controlled from a control panel similar to FIG. 30, though other embodiments include:
  a) a control panel of greater or lesser complexity;
  b) a wheeled vehicle which is not motorized, and is moved by the power and mechanical guidance of an enabler (i.e. a bystander who has decided to help in the resuscitative effort).

Tires 2202 (four are shown; larger or smaller numbers are possible), are rotated by an engine (not shown), using techniques known in the art. Steering and braking are accomplished by techniques known in the art. Headlights 2206A at the front of the vehicle (and an optional additional pair at the rear of the vehicle, not shown) aid in navigation. Front 2208 and rear 2210 video cameras are navigational aids for a remote vehicle pilot, which display a view of the selected camera(s) either within the screen shown in FIG. 30, or on a separate screen (see, for example, FIG. 37). Embodiments with a larger or a smaller number of cameras are possible. A global positioning device 2212 aids in locating a lost vehicle, and may be of use for navigation during a routine case.

Ideally, the device is maneuvered to approach a supine victim and to carefully move over the victim so that:
 a) the head-foot axis of the victim is centered under the central long axis of 2200; and
 b) chest compression shaft 2250 lies over the victim's sternum.

If the victim is not supine, either:
 a) an enabler (defined hereinabove) rotates/maneuvers the victim so that he is supine; or
 b) remotely maneuverable arms 2214 and 2216 may be used by a medical professional at the screen shown in FIG. 30 (or similar control screen) to manipulate the victim to the supine position.

Remotely controlled arm 2214 consists of:
 a) motor-containing/supporting unit 2214A which may also contain one or more joints;
 b) proximal (referring to the segment nearest to 2214A) arm segment 2214B;
 c) joint 2214C;
 d) mid-arm segment 2214D;
 e) joint 2214E;
 f) distal arm segment 2214F;
 g) joint 2214G;
 h) terminal arm segments 2214H and 2214I.

Remotely controlled arm 2216 consists of:
 a) motor-containing/supporting unit 2216A which may also contain one or more joints;
 b) proximal arm segment 2216B;
 c) joint 2216C;
 d) mid-arm segment 2216D;
 e) joint 2216E;
 f) terminal arm segment 2214F.

In a preferred embodiment of the invention, each of joints 2214C, E and G and each of joints 2216C and E are capable of:
 a) flexion and extension, such that the more distal member moves either towards of away from the more proximal member, while leaving unchanged the plane defined by the arm segments on either side of the joint; and
 b) rotation, such that the proximal member of each joint maintains a fixed spatial orientation, while the distal member of that joint maintains a fixed angle with respect to the proximal member.

In a preferred embodiment of the invention, each of arms 2214B, D and F and each of arms 2216B, D and F are capable of both shortening and of lengthening, when commanded to do so from the control screen.

Each of distal arms 2214H, 2214I and 2216F contains one or more specialized attachments at its terminal region. By way of illustration: 2214H contains a scissor, 2214I contains a razor and 2216F contains a gripping device. In a preferred embodiment of the invention:
 a) each arm would have at least one gripping device;
 b) when any arm has more than one specialized attachment, the MP could select which attachment is to be used, and could control that attachment.

Other embodiments are possible:
 a) without control arms;
 b) with more than two control arms;
 c) with only one or more than two specialized devices at the terminal end of each arm;
 d) with arms which contain a greater or lesser number of segments and joints; and
 e) with one or more arms mounted on the front, back, right side or left side of the vehicle.

Video cameras 2218 and 2220 on the underside of the vehicle allow the MP to precisely position the vehicle over the victim and do other tasks described hereinbelow. The under-vehicle scene may be further illuminated by lights 2206B. Optionally, each of 2218, 2220 and 2206B may be oriented by user controls; and each of cameras 2218 and 2220 (as well as front, rear and optional additional cameras) may have aspects of image processing controlled from the user screen.

Once the MP/user has determined that the vehicle is properly positioned over the victim, the vehicle is secured/locked in that position by:
 a) locking one or more of wheels 2202; and/or
 b) utilizing position-securing devices 2224A-D.

Figure 29B:
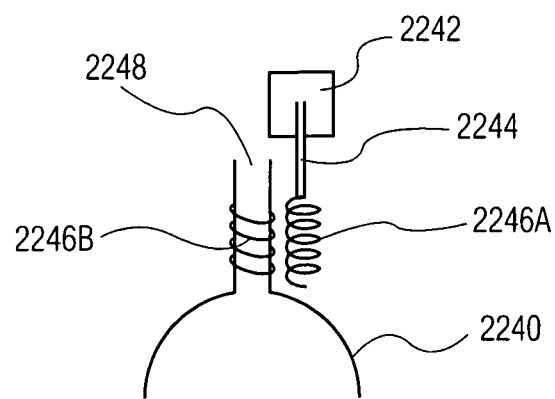
FIG. 29B shows a Suction cup-type vehicle immobilizing device.

One type of position-securing device is a suction cup apparatus shown in FIG. 29B. In one embodiment of the invention, the MP lowers suction cup 2240 by activating motor 2242 which turns shaft 2244. This turns worm-gear 2246A which turns worm gear 2246B which causes 2240 to move downward and to be forced against the surface which underlies the vehicle. To further increase the attractive force of the applied suction cup, the MP may cause a pump to apply a negative pressure inside the suction cup via hollow tube 2248. Not shown in the figure, but known in the art are:
 a) a pump to supply the negative pressure; and
 b) position guiding apparatus to stabilize 2248.

Embodiments with other mechanical arrangements for deploying the suction cup are possible and will be apparent to those skilled in the art.

Figure 29C:
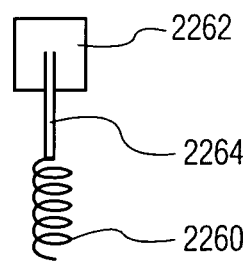
FIG. 29C shows a Corkscrew-type vehicle immobilizing device.

FIG. 29C shows a corkscrew type device 2260 for stabilizing the vehicle on an easily penetrated surface such as earth. 2260 is screwed into the ground by motor 2262, to which it is attached via shaft 2260. Embodiments are possible with separate shafts for the motor and for the corkscrew, with rotational force transmitted from one shaft to the other by belts, gears or both. Embodiments with other mechanical arrangements for deploying 2260 are possible and will be apparent to those skilled in the art.

Depending on the nature of the surface which lies beneath vehicle 2200, position stabilization by the suction cups (e.g. for a hard, flat surface), the corkscrew (for an earth surface) or wheel locking (e.g. for a carpet surface) may be best, and the choice is selected by the MP. The MP may select one means of vehicle stabilization, or more than one (e.g. in the case of a tiled floor, wheel locking first, followed by deployment of the suction cups); the MP may select to use different modalities at different points on the vehicle. Embodiments with a greater or lesser number of stabilizing devices are possible, including embodiments with both suction cup-type and corkscrew type devices. Embodiments with other types of vehicle position stabilizing devices will be obvious to those skilled in the art.

Once the vehicle is stabilized above the victim, the MP may:
 a) use video cameras 2218 and 2220 to assess the victim;
 b) maneuver scissor attachment 2214 and gripping attachment 2216F to cut the shirt/blouse and expose the chest, so that one or more ECG/defibrillator electrode pads may be applied to the chest;

c) maneuver razor attachment 2214I, if necessary, to shave hair from the victim's chest prior to electrode pad application;

d) apply the aforementioned electrode pads, using 2216F to take one or more pads from supply-depot 2226. This depot may contain a variety of electrode pads which are electrically hooked up as shown in FIG. 7B in U.S. Ser. No. 10/460,458 and geometrically arrayed in a series of compartments as shown in the upper portion of FIG. 7A (elements 166A-E therein) in U.S. Ser. No. 10/460,458. The housing for the aforementioned compartments may i) during vehicle non-use, lie within 2200; and ii) after vehicle stabilization, be cause to descend from the vehicle undersurface, allowing the MP to proceed with pad selection;

e) use gripping attachment 2216F (and, optionally, a second such attachment, if present, on arm 2214, to remove the backing of the pad and apply it to the chest wall of the victim;

f) apply an oxygen saturation transducer (not shown; discussed in conjunction with FIG. 7A [element 174] of U.S. Ser. No. 10/460,458) to a fingertip or ear lobe of the victim;

g) apply a blood pressure cuff (not shown; discussed in conjunction with FIG. 7A [element 172] of U.S. Ser. No. 10/460,458) to the victim's arm;

h) apply ventilation mask 2228 to the victim's face to supply oxygen, or air, or oxygen-enriched air to the victim; and to allow the measurement of end-tidal carbon dioxide. (Not shown is an optional strap or straps to hold the mask to the victim's face and/or nose clip within the mask which, when pinched, further enhances mask adherence to the victim's face.); and i) use ultrasound transducer 2230, mounted on a mechanism which is steerable by the MP and maneuvered so that it is touching the appropriate locations(s) on the victim's chest, to assess victim cardiac motion (and the status of his heart valves, aorta and pericardial space).

Once one or more of the electrode pads (to obtain electrocardiogram and, possibly, information about the victim's respiration, if any [by transthoracic chest impedance measurements]), oxygen saturation transducer, blood pressure cuff and ventilation mask are applied to the victim, the MP can medically assess the victim. He can thereby decide on the need, if any, for:

a) cardioversion or defibrillation;
b) pacing (either for bradycardia or tachycardia;
c) chest compression; and/or
d) ventilation;

and he can proceed with the required therapies, if any. The electrical aspects of arrest management, from this point, are as described in U.S. Ser. No. 10/460,458, and utilize remote control defibrillator and communications apparatus 2222 (The broken line forming its perimeter indicates its placement within the body of vehicle 2200.). Chest compression and ventilation are as described hereinbelow, in conjunction with FIG. 31.

At the end of the encounter between victim and vehicle:

a) shaft 2250 is raised so that its bottom is flush with the undersurface of the vehicle or is retracted inside of it;

b) such tasks as electrode pad removal or disconnect, and face mask removal or disconnect may be accomplished by either arms 2214 and 2216, or an on-scene enabler;

c) arms 2214 and 2216 are maneuvered to their neutral positions; and d) vehicle position stabilizing devices are deactivated:
   i) Any suction cup 2240, if used, may be detached by supplying positive pressure through 2248, and then using motor 2242 to raise that 2240;
   ii) Any corkscrew 2260, if used, would be removed from the ground by causing motor 2262 to turn in the direction opposite to that used in the initial setup;
   iii) The wheels, if locked, would be unlocked.

The simplest embodiment of the vehicle is a chest compression device on wheels, which is manually maneuvered into place. The weight of the vehicle stabilizes the compression device against recoil during a compression; therefore, the under-victim box or board (necessary in the conjunction with the biplane and triangular CPR devices and the rectangular and triangular CPR boxes) is unnecessary when the CPR vehicular device is used. Embodiments of the invention can be constructed with or without:

a) motorized control of the vehicle;
b) ventilation apparatus;
c) apparatus for MP-guided application of an electrode pad, and defibrillation;
d) apparatus for MP-guided pacing of the heart;
e) ultrasound apparatus;
f) GPS;
g) position securing apparatus; and
h) a deployable victim positioning device (other than arms 2214 and 2216) analogous to the inflatable bladders in the aforementioned CPR boxes (with suitable means for securing the bladders [e.g. one or more vertical projections extending downward from the vehicle under-surface]).

FIG. 30 shows a medical professional screen 2300 from which vehicular securing device 2200 and its associated position securing devices may be controlled.

The vehicle is maneuvered using joystick cluster 2302. (The curved line which extends from the element number and terminates in the central clear area of the up/down/right/left arrow cluster is intended to indicate that each of these four aforementioned controls is considered to be a joystick control and is collectively referred to as 2302. This terminology will be used throughout the discussion of 2300.) The upward point arrow calls for forward motion, the right-pointing arrow for a right turn, etc. Box 2304 gives the MP access to additional vehicle motion controls such as velocity, braking, drive wheel selection, etc. It also leads to a sub-menu (not shown), which allows raising or lowering the vehicle about the ground, to accommodate either particularly large or particularly small victims.

The MP is aided in vehicle positioning by using the vehicle video cameras, and displaying their image(s) on screen-in-screen image 2306. The controls which appear below 2306 in the figure (without element number since they are self explanatory) include:

a) selection of camera #1, #2, #3 and/or #4 (If more than one camera is selected, 2306 becomes a split screen.);
b) for the selected camera: selection of brightness, contrast, focus and zoom (which may be optical, digital or both); and
c) for the selected camera: selection of information density including frame rate and pixel density (e.g. by touching the empty pixel boxes and then inputting the desired value via a keyboard.

Further vehicle positioning aids include headlights control 2308 (which leads to a sub-menu, not shown) and GPS information access 2310.

Once the vehicle is in the desired position, the wheels may be locked by clicking on 2312; clicking on it a second time unlocks them. Clicking on 2314 enables suction cup lowering, which may then be further controlled by joystick cluster 2302. The up and down arrows causing up and down motion of the suction cups, and the right and left arrows causing the application of positive or negative pressure within the cups. If it is desired to control individual suction cups (rather than all four simultaneously), double clicking on 2314 gives access to a sub-menu, not shown, with detailed control options. Clicking on 2316 enables corkscrew-type vehicle stabilizer lowering, which may then be further controlled by joystick cluster 2302. The up and down arrows causing clockwise and counterclockwise motion of the corkscrew. If it is desired to control individual corkscrew-type stabilizers (rather than all four simultaneously), double clicking on 2316 gives access to a sub-menu, not shown, with detailed control options.

Cluster 2318 controls joint 2214C (FIG. 29A), i.e. the most proximal joint of arm 2214, or arm #1. The up and down boxes cause joint flexion and extension, respectively, while the right and left boxes cause clockwise or counterclockwise rotation along the shaft of 2214B. Clicking on box 2320 causes extension of proximal segment 2214B, while clicking on box 2322 causes shortening of 2214B.

In similar fashion to the control of joint #1, cluster 2324 controls joint 2214E, i.e. the middle joint of arm #1. The up and down boxes cause joint flexion and extension, respectively, while the right and left boxes cause clockwise or counterclockwise rotation along the shaft of 2214D. Clicking on box 2326 causes extension of middle segment 2214D, while clicking on box 2328 causes shortening of 2214D.

Cluster 2330 controls joint 2214G, i.e. the distal joint of arm #1. The up and down boxes cause joint flexion and extension, respectively (between segments 2214H and 2214F, while the right and left boxes cause clockwise or counterclockwise rotation along the shaft of 2214F. Clicking on box 2332 causes extension of distal segment 2214F, while clicking on box 2334 causes shortening of 2214F. Clicking on box 2336 causes joint flexion and extension, respectively (between segments 2214H and 2214F).

Boxes 2340-2350 control the specialized attachments for arm #1. For example:
a) 2340 and 2342 may cause opening and closing of the scissors at the end of arm segment 2214H;
b) 2344 may cause activation of an electric razor at the end of 2214I (and a second click may cause deactivation); and
c) 2346 may cause tilting of the angle of the razor with respect to the skin surface (and a second click may cause tilting in the opposite direction).

Boxes 2348 and 2350 may cause clockwise and counterclockwise rotation of arm housing 2214A.

Control of arm #2 is similar to the control of arm #1, except that, in the embodiment of the invention shown in FIG. 29, arm #2 has one less joint than arm #1, and the control screen reflects this. Cluster 2352 controls joint 2216C, i.e. the proximal joint of arm #2. The up and down boxes cause joint flexion and extension, respectively, while the right and left boxes cause clockwise or counterclockwise rotation along the shaft of 2216B. Clicking on box 2354 causes extension of proximal segment 2216B, while clicking on box 2356 causes shortening of 2216B.

In similar fashion to the control of joint #1 of arm #2, cluster 2358 controls joint 2216E, i.e. the distal joint of arm #2. The up and down boxes cause joint flexion and extension, respectively, while the right and left boxes cause clockwise or counterclockwise rotation along the shaft of 2216F. Clicking on box 2360 causes extension of distal segment 2216F, while clicking on box 2362 causes shortening of 2216F.

Boxes 2364-2370 are used to manipulate the grasping device at the end of 2216F. 2364 and 2366 open and close the jaws, while 2368 and 2370 increase and decrease the force applied between the two grasping segments.

Boxes 2372 and 2374 may cause clockwise and counterclockwise rotation of arm housing 2214A.

The selection and control of other specialized attachments for either arm #1 or arm #2 may be accessed through box 2376, which may lead to one or more sub-menus, not shown.

As discussed hereinabove, one or both arms may be used to select one or more electrode pads for placement on the suitably prepared chest of the victim. The pad selection menu consists of boxes 2378-2388. Selection possibilities include clicking on box:
a) 2378, to remove two single-electrode pads, one at a time;
b) 2380, to remove more than two single-electrode pads, one at a time (specifying the number of such pads with a keyboard entry);
c) 2382, to remove a 5 electrode pad (see U.S. Ser. No. 10/460,458 for description) with additional inboard ECG electrodes;
d) 2384, to remove a 5 electrode pad (see U.S. Ser. No. 10/460,458 for description) without additional inboard ECG electrodes;
e) 2386, to remove a matrix electrode pad (see U.S. Ser. No. 10/460,458 for description); and
f) 2388, to remove another type of electrode pad.

AS discussed in U.S. Ser. No. 10/460,458, once the electrode pad has been applied to the victim, the MP may access the ECG setup screen by clicking on box 2390 (e.g. to select the electrodes from which the ECG is read; see FIG. 29 of U.S. Ser. No. 10/460,458). If the MP determines that there is a need for pacing or defibrillation he may:
a) go to the pad setup screen by clicking on box 2392, to select the electrodes through which pacing or defibrillation energy is applied (see FIGS. 30, 31 and 32 of U.S. Ser. No. 10/460,458);
b) go to the main defibrillation menu (see FIG. 33 of U.S. Ser. No. 10/460,458); or
c) go to the main pacing screen (see FIG. 38 of U.S. Ser. No. 10/460,458).

The MP may choose to initiate CPR before, after or instead of electrical therapy. He can access the CPR control screen by clicking on 2398 (discussed hereinbelow in conjunction with FIG. 31). He may go to the Main Menu (from which he can access all menus) by clicking box 2400.

Cluster 2402 allows the MP to manipulate the position (up/down/right/left) of cardiac ultrasound probe 2230 on the underside of vehicle 2200. Cluster 2404 allows the manipulation of the angle that the probe makes with the victims chest wall. Boxes 2306 allow the MP to push the probe with either greater or less force. Clicking on boxes 2308, 2310 and 2312 allows the MP to control ultrasound image processing.

Other embodiments of control screen 2300 are possible including those:
a) with greater numbers of controllable items (e.g. the orientation of each of the vehicle's video cameras);
b) with smaller numbers of controllable items, either:
i) because the vehicle itself has fewer controllable items;
ii) because access to more of the controllable items is through sub-menus; or
iii) because control of some or all of the items controlled by so-called "clusters" (e.g. 2318) has been instead relegated to an actual joystick.
c) with different layouts of the control boxes on the screen.

Figure 31:
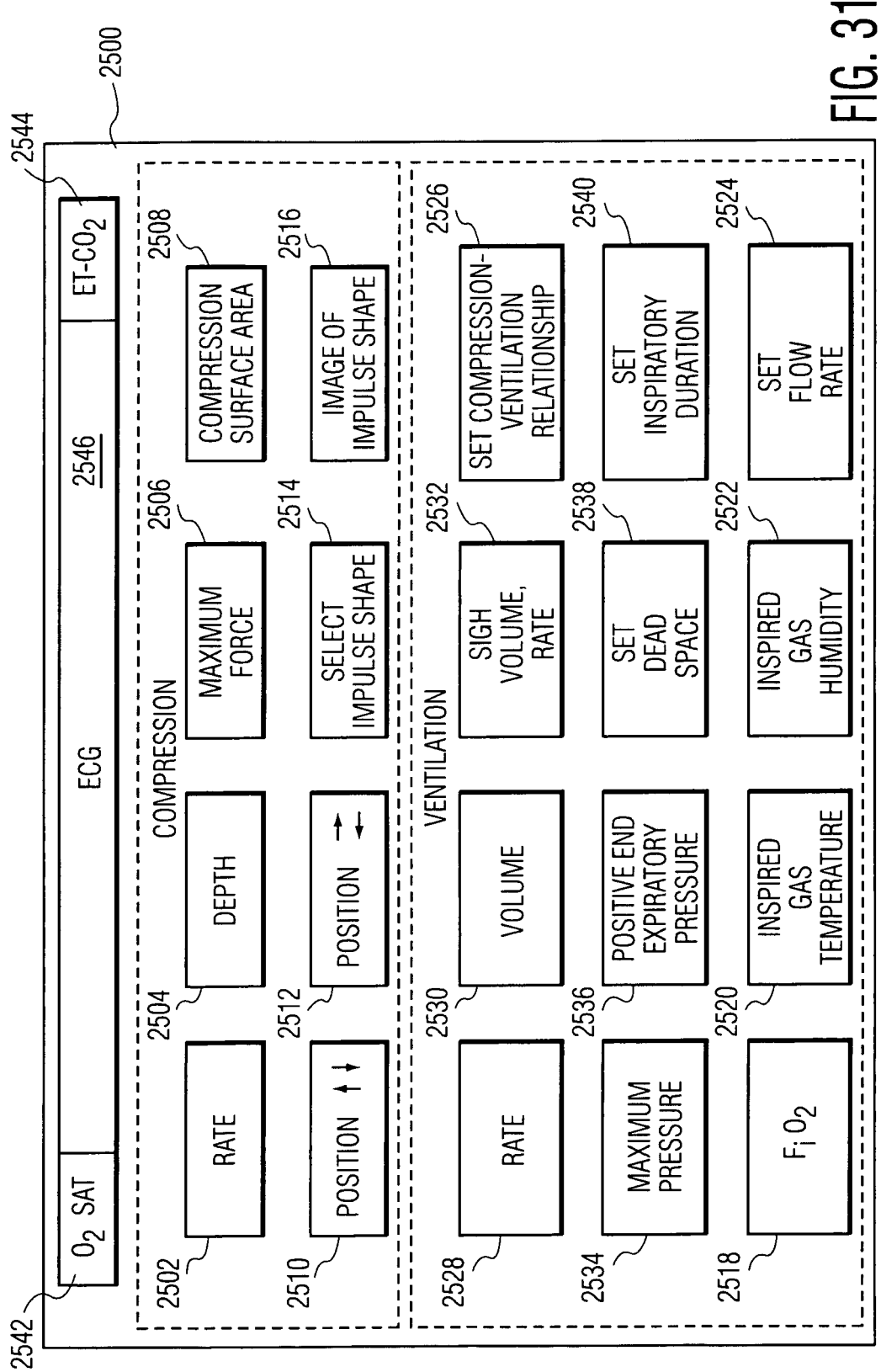
FIG. 31 shows a Compression/Ventilation control screen for CPR device.

FIG. 31 shows a control screen 2500 for the monitoring of CPR by a MP, that may be used in conjunction with the devices described herein.

The eight boxes within the upper broken line control chest compression. Clicking on box 2502 allows for control of the rate of chest compression. Clicking on it leads to either a sub-menu (not shown) with choices for compression rate, or clicking on 2502 could be followed by a keyboard entry with the desired rate.

The depth of chest compression is entered in similar fashion to rate, by clicking on 2504. Specifying a value of depth is best accompanied by the setting of a maximal value of compression force, to avoid chest or rib injury; maximal force is set by clicking on 2506. Once set, the value of maximal force takes priority over compression depth; i.e. if the maximal force value is reached during a compression that has not yet reached the desired depth, that compression is terminated and the MP is alerted. Another parameter related to maximal force is the value of force at all times during the impulse: the impulse shape, selected by clicking on 2514. For example: for a force value that is constant from the start of the compression impulse until its end, the impulse shape is rectangular. There are a limitless number of other possible impulse shapes, e.g. sinusoidal, trapezoidal etc. A sub-menu (not shown) of such shapes may be selected via 2514. An image of a shape named in the sub-menu may be viewed in screen-in-screen 2516.

As indicated hereinabove, it is possible to design the portion of the compression element which contacts the victim's chest so that the contact surface area is a parameter which the MP can vary. This parameter is accessed by clicking on 2508. Finally, the MP may cause the compression element, or the compression device itself to move along the head-foot axis by clicking 2510 (once for headwards, and twice for footwards), after which the number of millimeters of desired motion is entered via the keyboard. Similarly, the MP may cause the compression element, or the compression device itself to move along the right-left axis by clicking 2512 (once for rightwards, and twice for leftwards), after which the number of millimeters of desired motion is entered via the keyboard.

The 12 boxes within the lower broken line control ventilation.

In cases where the victim is ventilated via a mask, the MP works with five parameters:
a) the oxygen fraction of inspired gas ($F_iO_2$) is set by clicking on 2518 and making a keyboard entry for the value;
b) the inspired gas temperature and humidity may be entered as keyboard values (or selected from a sub-menu [not shown]) by clicking on 2520 and 2522 respectively;
c) the gas flow rate (e.g. 4 liters per minute) may be entered as a keyboard value (or selected from a sub-menu [not shown]) by clicking on 2524; and
d) the compression-ventilation relationship may be entered or selected from a sub-menu (not shown) by clicking on 2526. Though the flow rate for a mask arrangement might, under some circumstances, be constant (in which case there is no relationship to enter), under other circumstances it may be desirable to try to augment ventilation by providing
  i) a high gas pressure during chest recoil (i.e. passive chest expansion after a compression), in order to promote the flow of gas into the lungs; and
  ii) a low gas pressure (or a negative pressure) during chest compression, in order to promote the flow of gas out of the lungs.

If so desired, such a relationship could be set by clicking on 2526, and then entering the high pressure and low pressure values.

In cases where the victim has been intubated (i.e. where an endotracheal tube has been inserted into the trachea), e.g. by EMTs (or where the MP is managing a hospital patient (discussed hereinbelow), the MP could set each of the aforementioned five parameters, as well as nine others which are accessed by clicking on boxes 2528-2540:
a) $F_iO_2$, and inspired gas temperature and humidity are set as previously indicated;
b) By clicking on 2526, the compression-ventilation relationship could simply be set as a ratio (e.g. 15:2), or further details could be entered relating to the exact timing of each breath with respect to each chest compression;
c) The respiratory rate is may be entered as a keyboard value (or selected from a sub-menu [not shown]) by clicking on 2528;
d) The tidal volume may be entered as a keyboard value (or selected from a sub-menu [not shown]) by clicking on 2530;
e) Each of the sigh rate and sigh volume (if so-called sigh breaths are desired) may be entered as a keyboard values (or selected from a sub-menu [not shown]) by clicking on 2532;
f) The maximum airway pressure may be entered as a keyboard value (or selected from a sub-menu [not shown]) by clicking on 2534. If the value is reached, options include one or more of:
  i) automatically decreasing the tidal volume;
  ii) automatically increasing the rate and decreasing the tidal volume;
  iii) automatically increasing inspiratory duration, if possible; and
  iv) notifying the MP.
g) the addition of positive end expiratory pressure or "PEEP," if desired, may be done by a keyboard entry of the desired value (or by selecting from a sub-menu [not shown]) by clicking on 2536;
h) the addition of so-called "dead space," aimed at increasing the carbon dioxide concentration of the blood, may be accomplished by clicking on 2538 (followed by keyboard entry or sub-menu (not shown) selection; and
i) the inspiratory duration and/or the flow rate, though not independent of each other, may be accessed and set by clicking on 2540 and 2524 respectively (each followed by a keyboard entry or sub-menu [not shown] selection).

The top of the screen allows for the display, if available of two parameters of gas exchange: a) oxygen saturation 2542; and b) end-tidal carbon dioxide 2544. The electrocardiogram, if available, is displayed at 2546.

Figure 32:
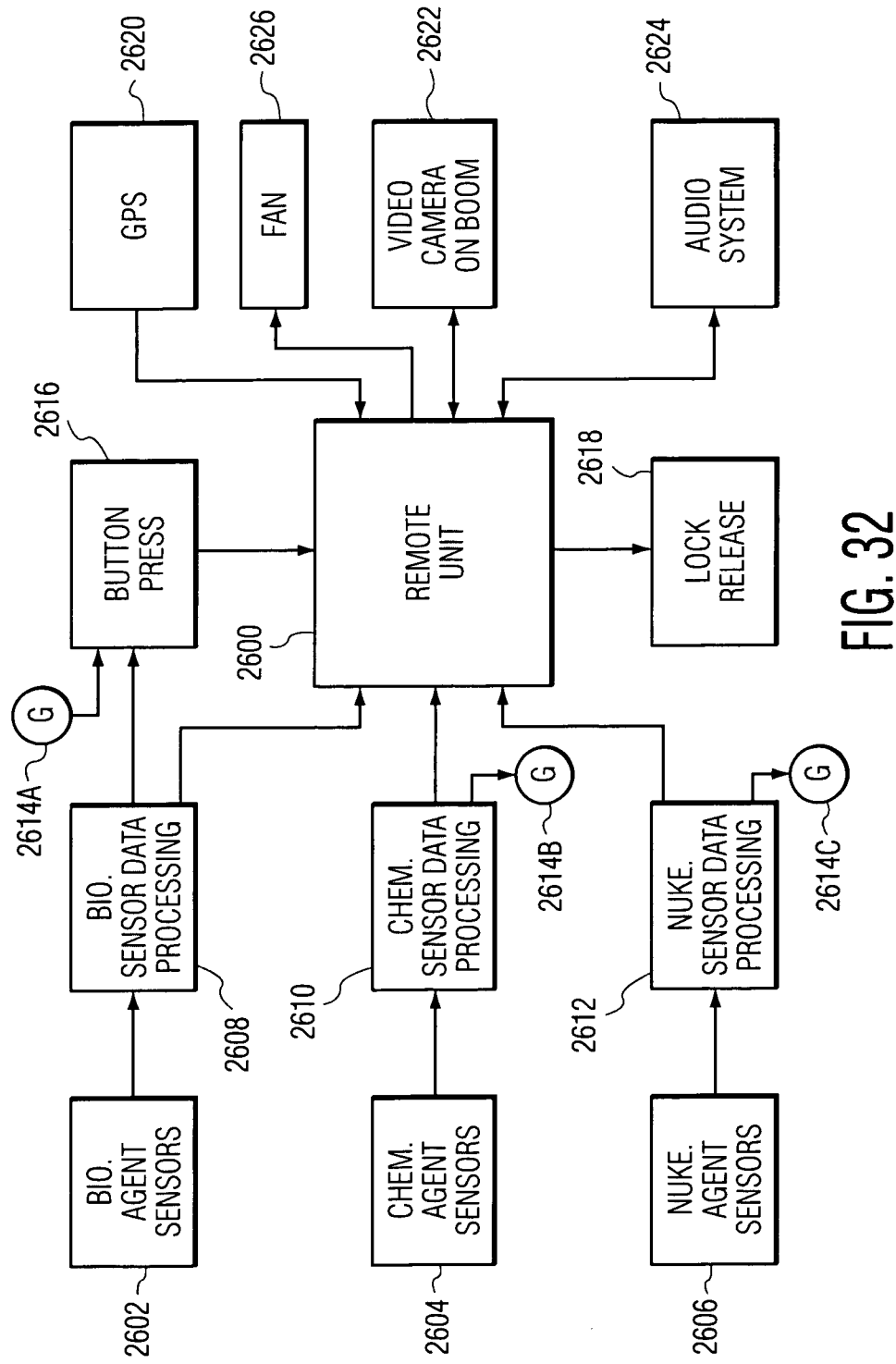
FIG. 32 shows a Remote Unit for Disaster Monitoring, hardware.
Figure 34:
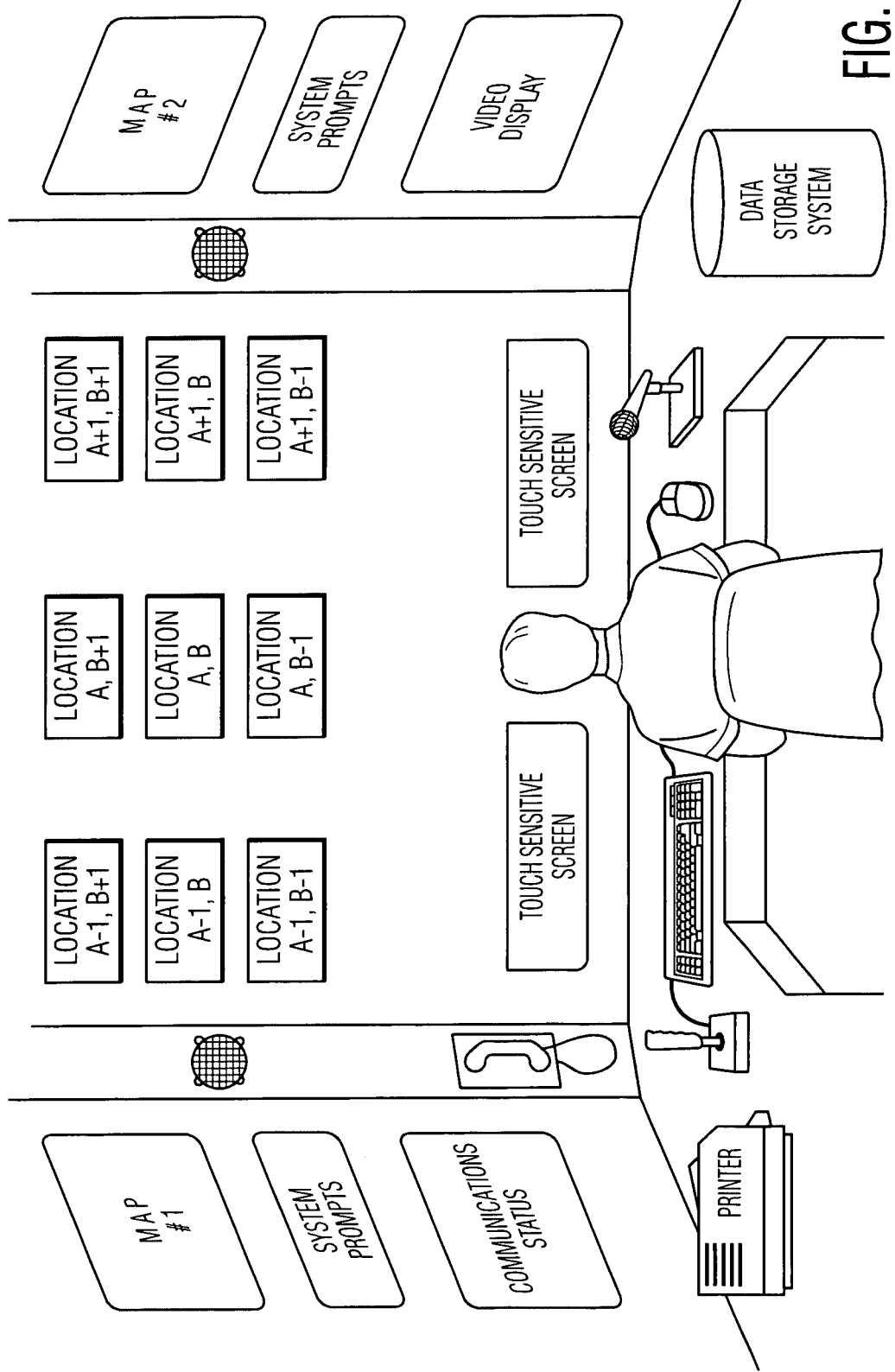
FIG. 34 shows a Central Station screen array, disaster management.

Overview of Invention 11 (FIGS. 32-34)

Suitably modified RCDs constitute a very good system for disaster monitoring, since they are devices which a) ideally are spread over a wide area; and b) are linked to a central station. The central station can thus simultaneously monitor conditions in a wide variety of locations. Such monitoring may involve:
a) surveillance for biological agents;
b) surveillance for chemical agents;

c) surveillance for nuclear agents; and
d) audio and video surveillance.

A disaster monitoring system could therefore consist of:
a) a network of modified RCDs
   i) fitted with biological, chemical and nuclear sensors;
   ii) fitted with a hardware/software package for processing the sensor outputs; and
   iii) able to communicate with a central station; and
b) a central station which is set up to display such data in various formats, and to act upon it.

Detailed Description of Invention 11 (FIGS. 32-34)

FIG. 32 shows a RCD 2600 which has been modified to accomplish the aforementioned sensing and notification tasks. Biological agent sensors 2602 input a biological sensor data processing unit 2608. If a biological agent is detected block 2616 is activated (this is the "pseudo-button press" discussed in U.S. Ser. No. 10/460,458; it is the electronic/data version of a manual button press; it may be viewed as the system pressing its own activation button). This causes the remote unit 2600 to transmit a message to the central station, alerting it to the detection of a biologic agent. Following an initial handshake with the CS, the details of the detection, block 2608 to block 2600 are transmitted. Other information which may be transmitted includes:
a) GPS data from block 2620;
b) audio and video data, from blocks 2624 and 2622; and
c) the input from other sensors, even if that input is below the threshold which would ordinarily trigger a button press.

The scenario for chemical agent detection is parallel to the aforementioned. Upon detection by 2610 of information suggesting a chemical threat based on information from one or more of sensors 2604, 2616 is activated. This causes the remote unit 2600 to transmit a message to the central station, alerting it to the detection of a chemical agent. Following an initial handshake with the CS, the details of the detection are transmitted: block 2610 to G2614B to G2614A to block 2600. The same optional information that could have been transmitted at the time of biologic threat detection may be transmitted at the time of chemical threat detection.

The scenario for nuclear agent detection is parallel to the aforementioned. Upon detection by 2612 of information suggesting a nuclear threat based on information from one or more of sensors 2606, 2616 is activated. This causes the remote unit 2600 to transmit a message to the central station, alerting it to the detection of a nuclear agent. Following an initial handshake with the CS, the details of the detection are transmitted: block 2612 to G2614C to G2614A to block 2600. The same optional information that could have been transmitted at the time of biologic threat detection may be transmitted at the time of nuclear threat detection.

Among the possible MP/NA/security agent actions upon a detection include:
a) manipulation of the video camera (i.e. its orientation/field of view, zoom, parameters related to image clarity and frame rate, etc., as described in U.S. Ser. No. 10/460,458);
b) actions related to the audio system including:
   i) manipulating gain, filtering and directionality to "listen" to events at the site of the remote unit; and
   ii) make an announcement over remote unit's speaker system (shown in U.S. Ser. No. 10/460,458) to guide/alert/advise people within earshot of the remote unit;
c) causing the fan 2626 to turn on, and thereby to provide a large air sample to the sensors, thereby to increase the unit's detection capability; and
d) if appropriate, cause the release (i.e. unlocking) of either:
   i) the remote unit from its locked-to-the-wall (or other stationary structure) state (by mechanisms described in U.S. Ser. No. 10/460,458) for use by an appropriately qualified professional on the scene; or
   ii) the door to a toolkit (see U.S. Ser. No. 10/460,458) within the remote unit, which may be outfitted to contain disaster management equipment, instructions or both.

FIG. 33 shows the disaster monitor/manager screen 2700 for use with the bio/chem/nuke-sensor outfitted remote units. Screen-in-screen 2702 displays a map of remote units spread over a densely packed metropolitan area (Manhattan, in this example). Units 2704 whose corresponding small squares are filled in, indicate definite (or high concentration) detection of an agent (biological, chemical or nuclear). Units 2706 noted by small circles, indicate possible (or low concentration) detection of an agent; while units 2708 which are unfilled, indicate no detection of an agent. The map, for example, is consistent with the release of an agent which is spreading from the midtown Manhattan area, with the pattern suggesting spread in the south by southwest direction. If the user chooses to, he can zoom in using 2703B or zoom out using 2703A. In one embodiment of the invention, the user can also zoom in on a particular sensor by clicking on its location on the map within 2702, or on a group of sensors by clicking and dragging to form a rectangle around the desired group.

The user can display the data from all sensors by clicking on 2710. Color coding may facilitate this, as would zooming in, simply to allow the screen to accommodate the additional data.

Another approach to zooming in is discussed hereinbelow.) Alternatively, the user can choose to click on:
a) 2712 to show only the data from biological sensors;
b) 2714 to show only the data from chemical sensors;
c) 2716 to show only the data from nuclear sensors; or
d) 2718 to show the data from a specific category of sensors (e.g. gamma rays of a certain energy), using the keyboard (or a sub-menu, not shown) to indicate the category.

The user can examine the evolution of the data over time by clicking on:
a) 2720 to display the state of the sensors at some previous time, 't' (to be entered via keyboard); or
b) 2722 to show a 'movie' of sensor data evolution over a time interval indicated by two keyboard entries.

By clicking on 2724, the user can cause the remote unit to obtain a so-called "hyper-sample," by causing a fan in the remote unit to pass large volumes of ambient air to its detectors, thereby sampling a larger volume of air per unit time than would be the case without the fan.

Besides display 2702, the user may display data on an array of screens shown in FIG. 34 and discussed hereinbelow. Options include clicking on:
a) 2726 to show a detailed 3×3 display (including one remote unit of particular interest in the center, and a nearest neighbor in each of eight directions);
b) 2728 to show a detailed 6×6 display (including one remote unit of particular interest in the center, and five nearest neighbors in each of eight directions (accomplished by splitting each screen in the central display area in FIG. 34 into a 2×2 array); and c) 2730, followed by a keyboard entry, to select a particular display format for the large overhead array.

The user may, by clicking on 2732 show the locations of various types of emergency services, superimposed on the display within 2702.

Communication with one or more remote units is formatted as follows: The user may:
a) speak to one or more remote units by clicking on 2734.
   i) If he chooses to speak to only one unit, he clicks on 2740 and then enters the unit ID# via keyboard, or clicks on it, on the map shown in 2702;
   ii) If he chooses to speak to a cluster of units, he clicks on 2742 and then enters the unit ID#s via keyboard, or clicks on each of them (or clicks and drags over the region), on the map shown in 2702;
   iii) If he chooses to speak to all units, he clicks on 2744;
b) listen to one or more remote units by clicking on 2736.
   i) If he chooses to listen to only one unit, he clicks on 2740 and then enters the unit ID# via keyboard, or clicks on it, on the map shown in 2702;
   ii) If he chooses to listen to a cluster of units, he clicks on 2742 and then enters the unit ID#s via keyboard, or clicks on each of them (or clicks and drags over the region), on the map shown in 2702;
   iii) If he chooses to listen to all units, he clicks on 2744;
c) speak and listen to one or more remote units by clicking on 2738. He takes the same actions as indicated immediately above, using boxes 2740, 2742 and 2744, depending on the scope of his intended action. Interaction with individual passers-by would also be possible using 2738, then 2740 and then entering the unit ID# or clicking on it in box 2702.

Additional audio management options are accessed through:
a) 2746, which controls the gain for both listening (single click, followed by keyboard entry or sub-menu [not shown]) and "speaking/broadcasting/announcing" (double click, followed by keyboard entry or sub-menu [not shown]); and
b) 2748, which helps with listening, and/or distinguishing one sound or set of sounds from others, by allowing the user to filter out/suppress certain frequencies (or types of sounds) and to emphasize others; Clicking on 2748 leads to a sub-menu [not shown] which allows these tasks.

Additional video management options are accessed through:
a) 2750, which allows the user to manipulate (both physically [i.e. orientation, optical zoom] and electronically/digitally [frame rate, pixels per frame, digital zoom]) the video camera at each location; and
b) 2752, which allows the user to control a video display on the remote unit (see U.S. Ser. No. 10/460,458), which may contain text or video updates for people near the remote unit, or disaster management instructions.

By clicking on 2754, the user can go to a map menu (e.g. other areas of New York City, of New York State, of other cities, etc.). By clicking on 2756, the user accesses a Main Menu containing a listing of, and access to, all other menus.

Disaster management screens are possible with:
a) a larger number of selectable options;
b) a smaller number of selectable options;
c) a larger number of screen-in-screen displays; and
d) different geometrical layouts of the boxes.

FIG. 34 shows the array of screens in a central station, for disaster management. The 11 screens in the central area directly facing the user consist of a) two lower touch sensitive screens such as 2700 (FIG. 33) and any of the sub-menus; and
b) a 3×3 array arranged to hyperfocus on one remote unit (arbitrarily assigned location coordinates [A, B]), shown in the center, and to display one nearest neighbor in each compass direction. Thus, for example, the nearest neighbor to the north is designated as [A, B+1], and the nearest neighbor to the southwest is designated [A−1, B−1]. This format is accessed by clicking on 2726 (FIG. 33). Each of the nine screens may display information including:
a) detailed data, over a period of time from each of a number of types of biological sensors;
b) detailed data, over a period of time from each of a number of types of chemical sensors;
c) detailed data, over a period of time from each of a number of types of nuclear sensors;
d) data derived from hypersampling;
e) live and prior video information from that unit's video camera; and
f) data concerning critical facilities (government, industry, military, hospitals, police, fire and other civil defense officials) located in the vicinity of that particular remote unit.

As indicated hereinabove, the 3×3 format may be changed to a 6×6 or other format, using 2700.

In addition to the central screens, side screens display:
a) additional maps which may be called up from a map menu (2754);
b) system prompts, which may include:
   i) newly occurring events that the system is aware of, but that the user has not yet become aware of;
   ii) pre-planned civil defense algorithms, which the system can guide the user through;
   iii) medical facts about specific toxins;
   iv) reports from other central stations;
   v) reports from a government broadcasting network, either local, or larger scale; and
   vi) weather reports;
c) a summary of communication issues including:
   i) an ongoing assessment of the ability of public and private communication systems to handle message traffic; and
   ii) the availability of other professionals like himself, either in large "master" central stations, or in one-person peripheral stations, to handle overflow traffic; and
d) video of:
   i) a selected remote unit outside of the grid located in front of the user;
   ii) of a public or cable television network; or
   iii) of a private communications network.

Figure 35:
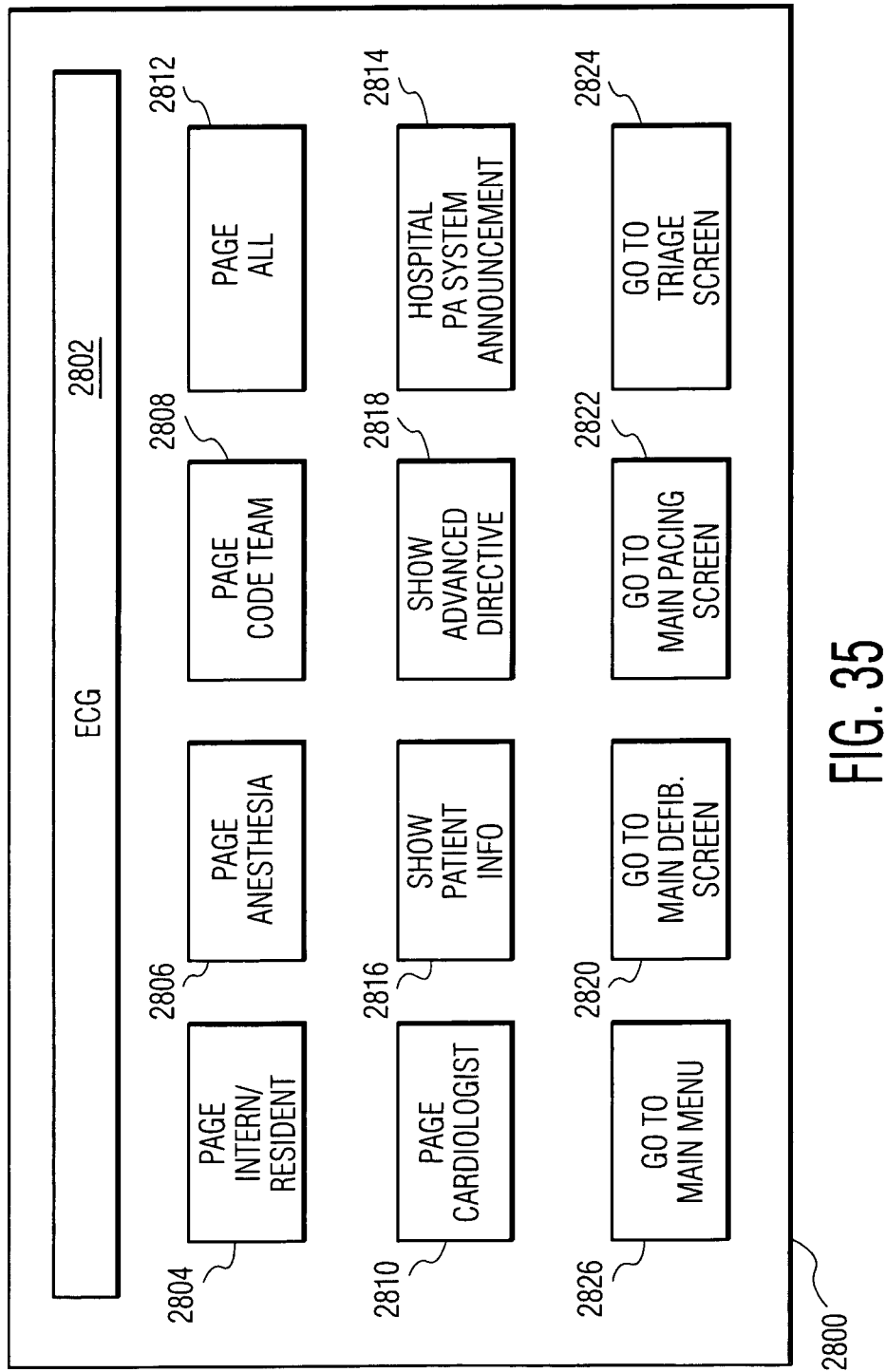
FIG. 35 shows a Hospital/Rehab patient monitoring/management screen.
Figure 36:
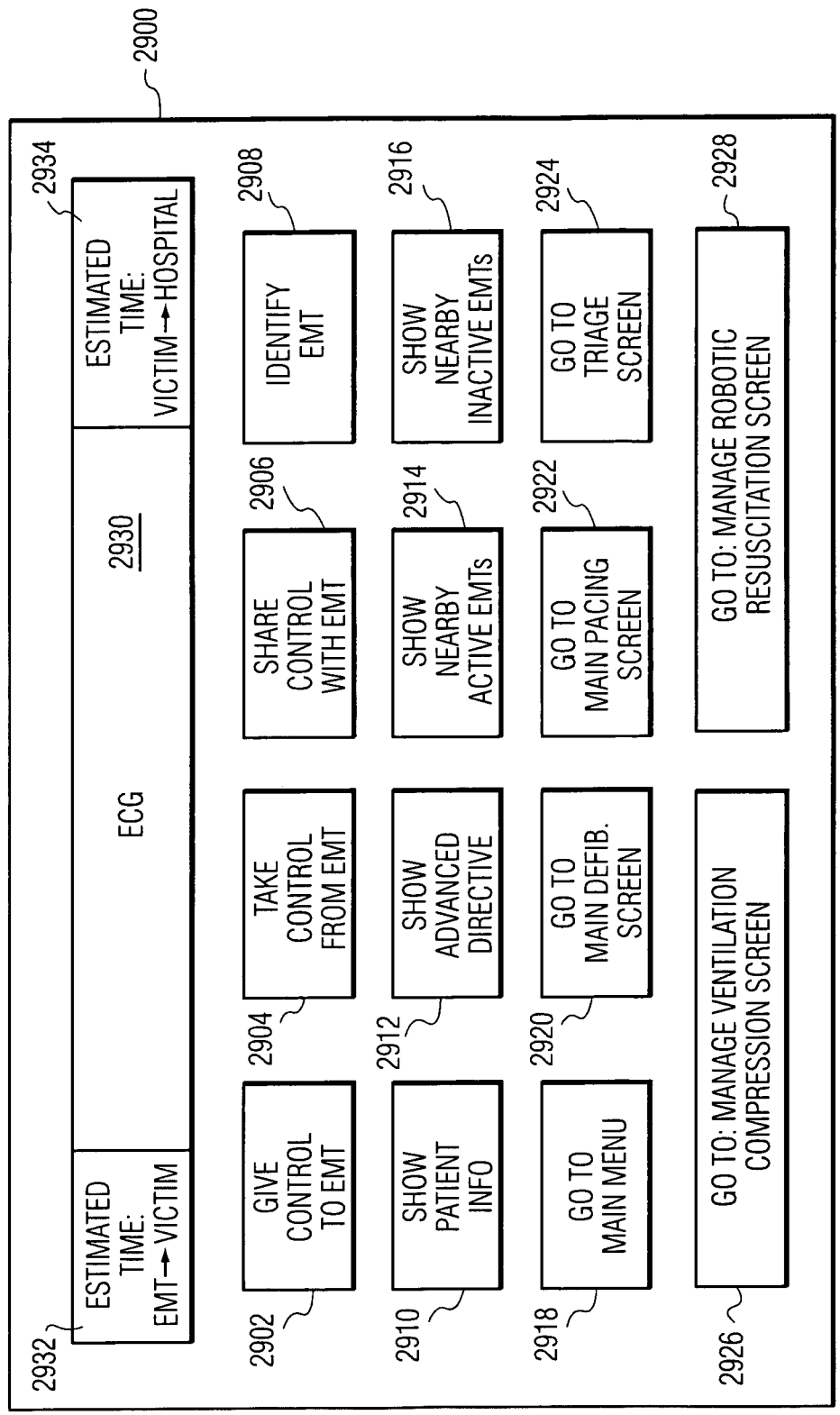
FIG. 36 shows an EMT monitoring/management screen.
Figure 37:
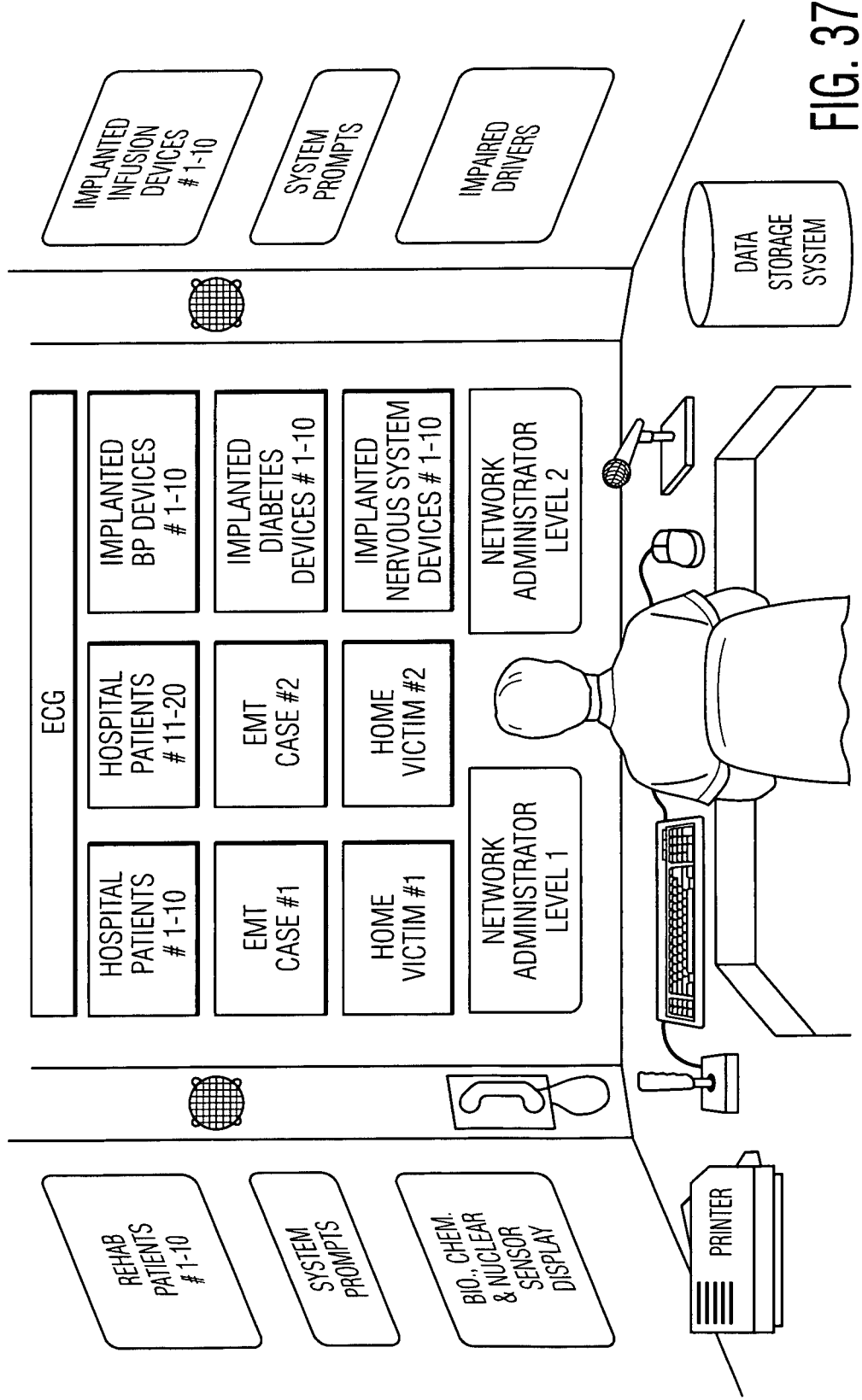
FIG. 37 shows a Master Central Station control panel for implanted blood pressure, diabetes, nervous system and infusion devices; hospital and rehab patients, EMT cases, solo and home victims; impaired drivers, disaster management and network administration.

Overview of Invention 12 (FIGS. 35-37)

The Medical Professional (MP) in a Central Station, as described in U.S. Ser. No. 10/460,458, is capable of managing a variety of medical events in which he reads the electrocardiogram (ECG), interprets it and makes and executes major decisions based upon the interpretation. This invention broadens the scope of the MP activities to include:
a) other ECG-based monitoring tasks such as:
   i) monitoring and treating hospital patients;
   ii) monitoring and treating patients in a rehabilitation facility (cardiac or otherwise); and
   iii) monitoring and treating patients under the care of an emergency medical technician or team; and b) other non-ECG based monitoring tasks such as:
  i) diabetes management (with and without implanted sensors/pumps);
  ii) blood pressure management (with or without implanted sensors and control devices)
  iii) monitoring and management of implanted pumps which may contain narcotics or chemotherapy;
  iv) monitoring and management of implanted central nervous system devices, for e.g. for control of seizures, obsessive compulsive disorder, etc. and
  v) monitoring and managing vehicles to detect impaired drivers.

Detailed Description of Invention 12 (FIGS. 35-37)

FIG. 35 shows a screen 2800 which allows a MP in a central station (which, in the preferred embodiment of the invention is outside of the hospital or rehabilitation facility) to manage hospital patients and patients in a rehabilitation facility. The MP observes the ECG in two ways:
  a) (see FIG. 37): on an array of screens, each of which may show multiple simultaneous ECGs. (This mass screening of ECGs may be augmented by a computer screening system which, preferentially has a very high sensitivity, even if its specificity (for detecting major arrhythmia) is low);
  b) on screen-in-screen 2802, which shows the ECG of a single "person of interest," who may have had a notable rhythm abnormality in the immediate few moments.

If the MP detects a serious rhythm problem, he pages one or more or of:
  a) 2804, the intern/resident;
  b) 2806, the anesthesia doctor or nurse;
  c) 2808, the "code" (i.e. cardiac arrest) team; and
  d) 2810, the attending or supervising cardiologist.

He can page all of the above simultaneously by clicking on 2812. If he is unsuccessful, in part or completely, with his paging, he can access the hospital overhead announcement system and page the appropriate staff. His page may consist of a text message or a voice message.

If the emergency is a cardiac arrest, the MP can, if authorized to do so, go ahead and treat the victim, if
  a) the victim is either already hooked up to a remote controlled defibrillation system (e.g. a high risk coronary care unit patient with electrode pads on his chest)
  b) the victim is in the vicinity of a bystander who can (as "an enabler") participate in the preliminaries of arrest management, while guided by the MP (as discussed in U.S. Ser. No. 10/460,458); or
  c) the victim is in the vicinity of a vehicular resuscitative robot system, of the type which can be controlled by the MP, as described hereinabove.

To treat the victim the MP has a variety of options. If electrode pads are already hooked up, the MP can diagnose ventricular tachycardia or fibrillation and, clicking on 2820, go to the main defibrillation screen (as in U.S. Ser. No. 10/460,458) and treat the victim. If electrode pads are already hooked up, the MP can diagnose a rhythm requiring cardiac pacing and, clicking on 2822, go to the main pacing screen (as in U.S. Ser. No. 10/460,458) and treat the victim. If electrode pads are not already hooked up, MP options include:
  a) working with an enabler (with appropriate management screens reached through Main Menu access 2826 (as in U.S. Ser. No. 10/460,458); and
  b) working with a resuscitative robot vehicle, via screen 2300 as described hereinabove.

Other MP management options include:
  a) displaying additional victim related information via 2816 and victim advanced directives (e.g. a living will, or a designation of who will make life and death decisions if the victim can not do so) via 2818; and
  b) triaging the case to another MP via 2824.

FIG. 36 shows a screen 2900 which allows a victim to work with an emergency medical team (EMT) outside of a hospital facility in a number of formats including:
  a) giving control to them (via 2902), when they arrive on the scene of an arrest (as described in U.S. Ser. No. 10/460,458), after confirming the identity of the EMT via 2908;
  b) taking control from them (via 2904), if either:
    i) they ask him to do so; or
    ii) they are incompetent, and he is authorized to do so;
  c) sharing control with them (via 2906), generally by mutual agreement; and
  d) helping them deal with time and manpower pressures by:
    i) showing nearby inactive EMTs (via 2916), who may be available to help in routine matters;
    ii) showing nearby active EMTs (via 2914), who may be available to help only in the event of dire emergency;
    iii) showing time estimates for their arrival at the arrest scene, and their estimated transport time (based on route and traffic patterns) to one or more nearby hospitals.

If the MP is to manage the victim:
  a) He monitors the victim's ECG on screen-in-screen 2930.
  b) If electrode pads are already hooked up, the MP can diagnose ventricular tachycardia or fibrillation and, clicking on 2920, go to the main defibrillation screen (as in U.S. Ser. No. 10/460,458) and treat the victim. If electrode pads are already hooked up, the MP can diagnose a rhythm requiring cardiac pacing and, clicking on 2922, go to the main pacing screen (as in U.S. Ser. No. 10/460,458) and treat the victim.
  c) If electrode pads are not already hooked up, the MP can ask the EMTs to do so.

Other MP treatment options are:
  a) maneuvering the resuscitative robot vehicle, via screen 2300, by clicking on 2928;
  b) managing chest compression and/or ventilation (by any of the automated CPR delivery devices discussed hereinabove) by clicking on 2926;
  c) displaying additional victim related information via 2910 and victim advanced directives (e.g. a living will, or a designation of who will make life and death decisions if the victim can not do so) via 2912;
  d) triaging the case to another MP via 2924; and
  e) performing other MP functions with appropriate management screens reached through Main Menu access 2918 (as in U.S. Ser. No. 10/460,458).

FIG. 37 shows an array of screens for managing:
  a) implanted devices including:
    i) blood pressure sensing/treating devices;
    ii) blood sugar sensing/treating devices for the management of diabetes;
    iii) implanted nervous system (both central and peripheral) devices, e.g. for the treatment of seizures, obsessive-compulsive disorder and pain management; and
    iv) implanted infusion devices for the delivery of chemotherapy, antibiotics and pain medications;
  b) hospital and rehabilitation patients;
  c) EMT cases;
  d) solo victims (i.e. those who live, work or travel alone) with internal or external arrest sensors;

e) impaired drivers;
f) disaster management; and
g) network administration.

Element numbers are omitted because the items in the figure are all labeled with self explanatory titles.

The management of victims with implanted defibrillators is discussed in U.S. Ser. No. 10/460,458. The use of information from implanted pacemakers and leadless devices is discussed hereinabove and is incorporated into the displays which show home victims.

These screens could be amalgamated with the central station setup for cardiac arrest management as described in FIG. 3 of U.S. Ser. No. 10/460,458.

The format for managing the above-mentioned implanted devices parallels that for managing ICDs (implantable cardioverter defibrillators) presented in U.S. Ser. No. 10/460,458. That is, there are two approaches:
 a) the device performs according to its algorithm, and the MP observes the data upon which it is acting, the devices decisions/actions, and the MP has the opportunity to—if he chooses to—override the device decisions;
 b) the MP—using the data collected by the device—primarily controls the implanted device.

Thus, for example, in the case of the implanted blood pressure device, the MP could view the blood pressure information, and determine that the extent of carotid stimulation that the device is currently supplying, or is expected to supply, is excessive. The MP therefore overrides the device, and causes less carotid stimulation to be delivered, resulting in better and safer blood pressure management.

To accomplish these tasks, the MP need not examine every decision of every device. He could have his own screening algorithms, which only bring a minority of cases to his attention. For example, the algorithm could show him anyone whose blood pressure is less than 90 systolic, or anyone who has had a fall in systolic pressure of more than 20 mm Hg over a certain period of time.

Impaired drivers constitute a hazard that is amenable to central station management since:
 a) sensors inputting data to a central station, with data analysis by an expert and the ability of the expert to take control, are critical features of many of the inventions disclosed herein; and
 b) among the inventions disclosed herein are motor vehicle-based systems.

Impaired driver management could consist of:
 a) sensors which chemically analyze the drivers breath;
 b) sensors which analyze vehicle velocity (during straight-line driving and on turns), acceleration (during straight line driving and on turns; in the direction of travel and perpendicular to the direction of travel), and vehicle tipping/tilting motion and the rate of deceleration;
 c) sensors which analyze victim level of consciousness/awareness including optical devices as are known in the art for detecting motion of the globe of the eye and the eyelid; EEG sensors which may be electrical or magnetic; and devices which ask the victim to respond to a prompt;
 d) devices which sense cardio-respiratory status including the ECG, the blood pressure and the respiratory rate;
 e) devices which sense an ICD shock; and
 f) devices which sense the adjacent vehicles and stationary objects, and the distance and relative velocity between the driver's vehicle and the adjacent vehicle/stationary object.

The aforementioned information (e.g. alcohol on the breath, sleeping victim, etc.) would be transmitted to the MP in the CS, via a modified RCD which has additional "pseudo-button press" inputs (as described in U.S. Ser. No. 10/460,458 and as described hereinabove, in conjunction with FIGS. 20 (solo patient sensor systems) and 32 (disaster sensing). The transmission could be directly from a suitably modified free-standing RCD (such that it had inputs for the aforementioned events), or from a vehicle based system (also suitably modified with appropriate sensors and data processing) analogous to that shown in FIG. 22.

MP responses to a pseudo-button press indicating an impaired driver may include:
 a) communicating with the driver and requesting that he stop driving;
 b) communicating with a member of the driver's family;
 c) communicating with the local police; and
 d) taking control of the vehicle (using techniques which are known in the art) and causing it to safely pull to the side of the road and to stop driving.

The MP could also supply evidence for long term remedies such as driver and family education and, if necessary, license suspension and revocation. If the person continued to drive with an invalid license, the MP could detect it, and, either report it or safely pull the vehicle to the side of the road.

Impairment is a relative concept. A driver who is capable of adequate performance during good weather and road conditions may be incapable of adequate performance during poor conditions. The system could be used to detect such people and to take remedial action.

There has thus been shown and described a novel emergency management system which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A cardiac monitoring and resuscitation system which allows a victim of a medical emergency, who is located at one of a plurality of remote sites, immediate access to a medical professional located at a central station who can remotely diagnose and treat said victim, said system comprising, in combination:
 (a) a central station comprising:
  (1) a display device for displaying representations of (A) medical alert information from at least one sensor concerning a likelihood of abnormality of a victim, and (B) victim electrocardiogram signal information from applied contact electrodes for evaluation by said medical professional;
  (2) an input device, responsive to said medical professional, for producing a defibrillation control signal for controlling the application of a defibrillation pulse to said victim; and
  (3) a first transmuting/receiving (T/R) device, coupled to said display device and said input device, for electronic communication with emergency cardiac monitoring and defibrillation apparatus disposed at each of a plurality of remote sites; and
 (b) emergency cardiac monitoring and external defibrillation apparatus disposed at each of said plurality of remote sites, each said apparatus comprising a portable unit including:

(1) a second transmitting/receiving (T/R) de vice for electronic communication with said first T/R device of said central station;

(2) a defibrillator circuit, having a control input coupled to said second T/R device for generating a defibrillation pulse at a defibrillator circuit output in response to said defibrillation control signal at said defibrillator circuit control input;

(3) an electrocardiogram (ECG) circuit, having an ECG circuit output, coupled to said second T/R device and having an ECG electrode input;

(4) a plurality of contact electrodes, adapted to be placed by an enabler upon a chest wall of said victim, said plurality of contact electrodes being adapted to be arranged at separate locations on said chest wall for the receipt of ECG signals from said victim and for application of said defibrillation pulse to said victim;

(5) a connecting cable having a plurality of electric wires for connecting each of said contact electrodes to at least cine of (i) said ECG electrode input and (ii) said defibrillator output;

(6) at least one sensor having a sensor output, for providing medical alert information relating to said victim for analysis by data analysis circuitry to determine whether to alert said medical professional; and (7) to analysis circuitry coupled to the output of said at least one sensor for receiving said medical alert information, said data analysis circuitry having circuit output, coupled to said second T/R device, for producing at least one medical alert signal representing different degrees of likelihood that the victim may be in need of treatment for a medical emergency;

wherein
(1) said data analysis circuitry analyzes the output of said at least one sensor to determine one of at least four states of the victim, including:
  (A) an apparently normal state A representing a first degree of likelihood of abnormality;
  (B) a state B representing a second degree of likelihood of abnormality, which is greater than the first degree of likelihood of abnormality, but less than a third degree of likelihood of abnormality;
  (C) a state C representing said third degree of likelihood of abnormality, which is greater than the second degree of likelihood of abnormality, but less than a fourth degree of likelihood of abnormality; and
  (D) a state D representing a fourth, highest degree likelihood of abnormality, which is greater than the third degree of likelihood of abnormality;
(2) said data analysis circuitry causes said second T/R device to transmit a medical alert signal to said central station upon determination of at least one of said states B, C and D; and
(3) in response to receipt said medical alert signal, said display device is caused to display an indication of the respective second, third and fourth degree of likelihood of abnormality of the victim whereby (1) based on said analysis of said at least one sensor output, said medical alert signal may be transmitted to said central station, indicating the degree likelihood that the victim may be in need of treatment for a medical emergency; (2) said ECG signals from said contact electrodes may be transmitted from selected ones of said contact electrodes via said ECG circuit to said central station for evaluation by said medical professional, and (3) said defibrillation control signal may be applied to the defibrillator circuit to generate said defibrillation pulse fair application to at least one of said contact electrodes for resuscitation of said victim.

2. The monitoring system defined claim 1, wherein said central station further comprises a database, including (a) a computer memory in which stored a first list of contact information of possibly available enablers and (b) a processor, coupled to said computer memory and to said display device, for providing the information of said first list to said medical professional;

wherein said first list is displayed by said display device in response to the inputting to said input device a first list command by said medical professional;

whereby
(1) said medical professional may contact at least one enabler and dispatch said at least one enabler to the victim, in the event of at least one of a) a medical alert signal indicating a possibility et cardiac arrest, and b) uncertainty about interpretation of said medical alert signal;
(2) the enabler, upon arrival at the victim, may:
  a) report additional information to the medical professional; and
  b) follow resuscitation commands from the medical professional.

3. The monitoring system defined in claim 1, wherein said central station further comprises a database, including (a) a computer memory in which are stored a second list of contact information of possibly available emergency medical personnel, and (b) a processor, coupled to said computer memory and to said display device, for providing the information of said second list to said medical professional;

wherein said second list is displayed by said display device in response to the inputting to said input device of a second list command by said medical professional;

whereby said medical professional may contact said personnel, in the event of at least one of a) a medical alert signal indicating a possibility of cardiac arrest b) uncertainty about interpretation of said medical alert signal.

4. The monitoring system defined in claim 1, wherein
(1) said emergency cardiac monitoring and external defibrillation apparatus comprises at least two sensors, each having a respective sensor output coupled to said data analysis circuitry, for providing said medical alert information;
(2) said input device is further operative to input at least one sensor control responsive to said medical professional, for controlling a selection of at least one sensor output for determination by said data analysis circuitry whether to alert said medical professional;
(3) said at least one sensor control signal is transmitted to the data analysis circuitry; and
(4) in response thereto, said data analysis circuitry operative to select at least one sensor output for said determination;

thereby
to allow the medical professional to alter the source of sensor data the generation of future medical alert signals.

5. The apparatus defined in claim 1, wherein said data analysis circuitry is coupled to a plurality of said contact electrodes for sensing cardiac electrical activity.

6. The apparatus defined in claim 1, wherein said data analysis circuitry is coupled to a plurality of said contact electrodes for sensing transthoracic chest wall impedance.

7. The apparatus defined in claim 1, wherein said at least one sensor comprises a sensor for sensing respiration.

8. The apparatus defined claim 1, wherein said at least one sensor comprises an accelerometer for sensing sudden deceleration.

9. The apparatus defined claim 1, wherein said at least one sensor comprises a first sound transducer for sensing audible cardiac activity.

10. The apparatus defined in claim 1, wherein said at least one sensor comprises a second sound transducer for sensing audible sounds of distress.

11. The apparatus defined in claim 1, wherein said at least one sensor comprises a video camera.

12. The apparatus defined in claim 1, wherein said at least one sensor comprises a first orientation sensor for sensing a change in body attitude of the victim.

13. The apparatus defined in claim 1, wherein said at least one sensor comprises a second orientation sensor for sensing that the victim is in a supine position.

14. The app define in claim 1, wherein said at least one sensor comprises a heart rate sensor for sensing heart rate.

15. The apparatus defined in claim 1, wherein at least one of said medical alert signals produced by said data analysis circuitry indicates a value of said sensor output.

16. The apparatus defined in claim 1, wherein at least one of said medical alert signals produced by said data analysis circuitry indicates said likelihood that the victim may be in need of treatment.

17. A cardiac monitoring and resuscitation system which allows a victim of a medical emergency, who is located at one of a plurality of remote sites, immediate access to a medical professional (MP) located at a central station who can remotely diagnose and treat said victim, said system comprising, in combination:
(a) a central station comprising:
(1) a display device for displaying medical information from a victim for evaluation by said MP;
(2) an input device, responsive we said MP, for producing (a) a defibrillation control signal for controlling the application of a defibrillation pulse to said victim, and (b) at least one sensor selection signal, for selecting at least one sensor for alerting said central station; and
(3) a first transmitting/receiving (T/R) device, coupled to said display device and said first input device, for electronic communication with emergency cardiac monitoring and defibrillation apparatus disposed at each of a plurality of remote sites; and
(b) emergency cardiac monitoring and external defibrillation apparatus disposed at each of a plurality of remote sites, each said apparatus comprising a portable unit including:
(1) a second transmitting/receiving (T/R) device, for electronic communication with said first T/R device of said central stations; for
transmitting (i) a medical alert signal, and (ii) ECG signals; and
receiving (i) said defibrillation control signal, and (ii) at least one sensor selection signal;
(2) a defibrillator circuit, having a control input coupled to second T/R device, for generating a defibrillation pulse at a defibrillator circuit output in response to said defibrillation control signal received at said defibrillator circuit control input;
(3) an electrocardiogram (ECG) circuit having as EC circuit output, coupled to sa said second T/R device and having an ECG-electrode input;
(4) a plurality of contact electrodes, adapted to be placed by an enabler upon a chest wall of said victim under guidance of said MP, said plurality of contact electrodes being adapted to be arranged at separate locations on said chest wall for the receipt of ECG signals from said victim and for application of said defibrillation pulse to said victim;
(5) a connecting cable having a plurality of electric wires for connecting each of said contact electrodes to at least one of (i) said ECG electrode input and (ii) said defibrillator output;
(6) a plurality of sensors each having a respective sensor output, for providing medical alert information relating to said victim for analysis by data analysis circuitry to determine whether to alert said MP; and
(7) data analysis circuitry, coupled to each sensor output for receiving said medical alert information, said data analysis circuitry having a circuit output coupled to said second T/R device, for (a) receiving said at least one sensor selection signal, and (b) causing the transmission of a medical alert signal to said first T/R device;
wherein said data analysis circuitry is responsive to said at least one sensor selection signal to select at least one sensor output for determination by said data analysis circuitry whether to alert said MP;
wherein said data analysis circuitry analyzes the output of at least one sensor as selected by said at least one sensor selection signal, to determine whether to alert said MP that an abnormal state of the victim exists; and
wherein upon the detection of said abnormal state, said data analysis circuitry causes the second T/R device to initiate communication with the central station by transmitting said medical alert signal to the central station;
whereby said sensor selection signal represents a choice by said MP of at least one particular sensor output for analysis by said data analysis circuitry for determining whether to alert said MP;
and whereby
(1) said MP selects at least one sensor from among said plurality of sensors for said analysis for initiating future communication with said central station (2) at times after said selection said data analysis circuitry analyzes the sensor output of the at least one selected sensor to determine whether to notify said MP; (3) following said selection, in response to said analysis, said data analysis circuitry may produce said medical alert signal at said data analysis circuitry output to notify said MP of said abnormal state; (4) following transmission of said medical alert signal, said ECG signals may be transmitted from selected ones of said contact electrodes via said ECG circuit to said central station for evaluation by said MP, and (5) said defibrillation control signal may be applied to the defibrillator circuit which may generate said defibrillation pulse for application to at least one of a said contact electrodes for resuscitation of said victim.

18. The apparatus defined in claim 17, wherein said data analysis circuitry is coupled to a plurality of said contact electrodes for sensing cardiac electrical activity.

19. The apparatus defined in claim 17, wherein at least one of said plurality of sensors comprises contact electrodes for sensing transthoracic chest wall impedance.

20. The apparatus defined in claim 17, wherein at least one of said plurality of sensors comprises a sensor for sensing respiration.

21. The apparatus defined in claim 17, wherein at least one of said plurality of sensors comprises an accelerometer for sensing sudden deceleration.

22. The apparatus defined in claim 17, wherein at least one of said plurality of sensors comprises a first sound transducer for sensing audible cardiac activity.

23. The apparatus defined in claim 17, wherein at least one of said plurality of sensors comprises a second sound transducer for sensing audible sounds of distress.

24. The apparatus defined in claim 17, wherein at least one of said plurality of sensors comprises a video camera.

25. The apparatus defined claim 17, wherein at least one of said plurality of sensors comprises a first orientation sensor for sensing a change in body attitude of the victim.

26. The apparatus defined in claim 17, wherein at least one of said plurality of sensors comprises a second orientation sensor for sensing that the victim is in a supine position.

27. The apparatus defined in claim 17, wherein at least one of said plurality of sensors comprises a heart rate sensor for sensing heart rate.

28. The cardiac monitoring and resuscitation system of claim 17, wherein
    (1) said data analysis circuitry is further operative to produce an additional medical alert signal representing a likelihood that the victim may be in need of treatment for a medical emergency;
    (2) said data analysis circuitry analyzes said at least one sensor output and causes said second T/R device to transmit said additional medical alert signal to said medical professional in the even of an analysis indicative of at least a possible medical emergency; and
    (3) in response thereto, said display device displays a representation of the information contained in said additional medical alert signal;
    whereby said additional medical alert signal is automatically transmitted to said medical professional indicating that the victim may be in need of treatment for a medical emergency.

29. The apparatus defines in claim 28, wherein said data analysis circuitry is operative to determine whether the output of said at least one selected sensor represents a value of a parameter of the victim state selected from the group consisting of:
    (a) a definitely normal value;
    (b) a definitely abnormal value; and
    (c) a value which is not definitely normal and which is not definitely abnormal.

30. The apparatus defined in claim 29, wherein said data analysis circuitry produces said medical alert signal when the output of said at least one selected sensor represents a value of said parameter of the victim state indicating a possible medical emergency whenever said parameter is a definitely abnormal value.

31. The apparatus defined in claim 29, wherein said data analysis circuitry produces said medical alert signal when the output of said at least one selected sensor represents a value of said parameter of the victim state indicating a possible emergency whenever said parameter is neither a definitely normal nor a definitely abnormal value.

32. The apparatus defined in claim 28, wherein said medical alert signal produced by said data analysis circuitry indicates said likelihood that the victim may be in need of treatment.

33. The apparatus defined in claim 28, wherein said medical alert signal produced by said data analysis circuitry indicates one of a plurality of degrees of said likelihood that the victim may be in need of treatment.

34. The apparatus defined in claim 17, wherein said data analysis circuitry is further operative to cause said second T/R device to transmit said alert information to said first T/R device; and wherein said display device is further operative to display said alert information.

35. A person monitoring system which allows a monitoring medical professional to remotely monitor a medical problem of the person at one of a plurality of remote sites, said system comprising, in combination:
    (a) a central station comprising:
        (1) a display device for displaying medical information from a person for evaluation by a monitoring medical professional; and
        (2) a first receiving device, coupled said display device, for electronic communication with medical monitoring apparatus disposed at each of a plurality of remote sites; and
    (b) medical monitoring apparatus disposed at each of a plurality of remote sites, each said apparatus comprising:
        (1) a second transmitting device for electronic communication with said first receiving device of said central station;
        (2) at least one sensor having a sensor output, for generating person information indicating that said person may be in need of medical treatment;
        (3) data analysis circuitry, coupled to each of (i) said sensor output for receiving said person information and (ii) said second transmitting device, for producing at least one medical alert signal represent a degree of likelihood that said person may be in need of medical treatment, said data analysis circuitry being operative to analyze the output of said at least one sensor to determine one of four states of the victim:
    (A) an apparently normal state A representing a first degree of likelihood of abnormality;
    (B) a state B representing at second degree of likelihood of abnormality, which is greater than the first degree of likelihood of abnormality, but less than a third degree of likelihood of abnormality;
    (C) a to C representing said third degree of likelihood of abnormality, which is greater than the second degree of likelihood of abnormality, but less than a fourth degree of likelihood of abnormality; and
    (D) a state D representing a fourth, highest degree of likelihood of abnormality, which is greater than the third degree of likelihood of abnormality;
    and wherein
    (1) said data analysis circuitry causes said second transmitting device to transmit a medical alert signal to said central station upon determination of at least one of said states B, C and D;
    (2) in response to receipt of said medical alert signal, said display device is caused to display an indication of the respective second, third and fourth degree of likelihood of abnormality of the victim;
    whereby said monitoring device may automatically produce a medical alert signal to notify said monitoring medical professional of a degree of likelihood that a victim is in need of medical attention.

36. The person monitoring system defined in claim 35, wherein said device for obtaining personal information is configured to be implanted in the person.

37. The person monitoring defined in claim 35, wherein
    (A) said central station further comprises:
        an input device, responsive to said monitoring medical professional; and
        a first transmitting device, coupled to said input device; and (B) said medical monitoring apparatus further comprises a second receiving device for communicating with said first transmitting device;

(C) said input device is further operative to generate an alarm signal in response to an alarm input from the monitoring medical professional;

(D) said first transmitting op operative to transmit said alarm signal to said second receiving device of said medical monitoring apparatus; and (E) said medical monitoring apparatus further comprises an alarm device, coupled to said second receiving device, responsive to said alarm signal for sounding an alarm.

38. The patient monitoring system defined in claim 37, wherein said input device is operative to input an audio message from the monitoring medical professional, for transmission to said medical monitoring apparatus at said remote station.

39. The apparatus defined in claim 35, wherein said data analysis circuitry is operative to determine a value of a parameter representing the victim state.

40. The apparatus defined in claim 39, wherein said medical alert signal produced by said data analysis circuitry indicated the value of said parameter.

41. The monitoring system defined in claim 35, wherein at least one of said plurality of sensors comprises ECG electrodes for sensing cardiac electrical activity.

42. The monitoring system defined in claim 35, wherein at least one of said plurality of sensors comprises contact electrodes for sensing transthoracic impedance.

43. The monitoring system defined in claim 35, wherein at least one of said plurality of sensors comprises a sensor for sensing respiration.

44. The monitoring system defined in claim 35, wherein at least one of said plurality of sensors comprises an accelerometer for sensing sudden deceleration.

45. The monitoring system defined in claim 35, wherein at least one of said plurality of sensors comprises a first sound transducer for sensing audible cardiac activity.

46. The monitoring system defined in claim 35, wherein at least one of said plurality of sensors comprises a second sound transducer for sensing audible sounds of distress.

47. The monitoring system defined in claim 35, wherein at least one of said plurality of sensors comprises a video camera.

48. The monitoring system defined in claim 35, wherein at least one of said plurality of sensors comprises a first orientation sensor for sensing a change in body attitude of the victim.

49. The monitoring system defined in claim 35, wherein at least one of said plurality of sensors comprises a second sound transducer for sensing that the victim is in a supine position.

50. The monitoring system defined in claim 35, wherein at least one of said plurality of sensors comprises a heart rate sensor for sensing heart rate.

51. The monitoring system defined in claim 35, wherein said device for obtaining person information is configured to be situated external to said person.

52. The monitoring system defined in claim 35, wherein
(a) said central station further comprises:
    (3) an input device, responsive to said monitoring medical professional, for producing a defibrillation control signal for controlling the application of a defibrillation pulse to said victim; and
    (4) a first transmitting device, coupled to said input device for electronic communication with said medical monitoring apparatus at least one of said remote sites;
(b) said medical monitoring apparatus situated at at least one of said remote sites further comprises:
    (4) a second receiving device for communicating with said first transmitting device, for receiving said defibrillation control signal;
    (5) a defibrillator circuit, having a control input coupled to said second receiving device, for generating a defibrillation pulse at a defibrillator circuit output in response to said defibrillation control signal received at said defibrillator circuit control input;
    (6) an electrocardiogram (ECG) circuit, having an ECG circuit output, coupled to said second transmitting device for transmitting ECG signals to said monitoring medical professional, and having an ECG electrode input;
    (7) a plurality of contact electrodes, adapted to be placed by upon a chest wall of said person, said plurality of contact electrodes being adapted to be arranged at separate locations on said chest wall for the receipt of signals from said person and for application of said defibrillation pulse to said person;
    (8) a connecting cable having a plurality of electric wires for connecting each of said contact electrodes least one of (i) said ECG electrode input and (ii) said defibrillator output;
wherein
(a) said second transmitting device is further operative to generate a signal representing said ECG circuit output, and to transmit said signal to said first receiving device; and
(b) said display device is further operative display information represented by said signal representing said ECG output;
    whereby said monitoring medical professional (a) is notified of a situation which may require application of a defibrillation pulse to said person; and (b) can cause the input device to produce a defibrillation control signal which results in the application of said defibrillation pulse to said person.

* * * * *